(12) United States Patent
Kelly et al.

(10) Patent No.: US 6,355,664 B1
(45) Date of Patent: Mar. 12, 2002

(54) PHENYLPYRROLIDINES, PHENYLIMIDAZOLIDINES, 3-PHENYL-1,3-OXIZOLIDINES AND 3-PHENYL-1,3-THIAZOLIDINES AND THEIR USE IN THE TREATMENT OF INFLAMMATORY DISEASE

(75) Inventors: Terence A. Kelly, Ridgefield; Barbara Jean Bormann, Old Lyme, both of CT (US); Leah Lynn Frye, Patterson, NY (US); Jiang-Ping Wu, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/375,010

(22) Filed: Aug. 16, 1999

Related U.S. Application Data

(63) Continuation-in-part of application No. PCT/US98/04254, filed on Mar. 3, 1998, which is a continuation-in-part of application No. 09/033,148, filed on Mar. 2, 1998, now abandoned.
(60) Provisional application No. 60/040,011, filed on Mar. 3, 1997.

(51) Int. Cl.$^7$ ................ A61K 31/4439; A61K 31/4166; C07D 401/10; C07D 233/40

(52) U.S. Cl. ................... 514/389; 514/398; 546/274.4; 548/319.5; 548/321.1

(58) Field of Search ........................... 548/321.1, 319.5; 546/274.4; 514/389, 398

(56) References Cited

U.S. PATENT DOCUMENTS

| | | | |
|---|---|---|---|
| 3,668,217 A | 6/1972 | Fujinami | 548/320.5 X |
| 3,741,981 A | 6/1973 | Fujinami | 548/321.1 X |
| 3,846,441 A | * 11/1974 | Mine et al. | 548/321.1 |
| 4,911,748 A | * 3/1990 | Prisbylla | 548/321.1 X |
| 4,944,791 A | 7/1990 | Schroeder | 548/321.1 X |
| 4,977,270 A | * 12/1990 | Wee | 548/321.1 |
| 5,208,250 A | 5/1993 | Cetenko | 548/321.1 X |
| 5,306,822 A | 4/1994 | Cetenko | 548/321.1 X |
| 5,334,606 A | 8/1994 | McLeod | 548/321.1 X |
| 5,464,856 A | 11/1995 | Cetenko | 548/321.1 X |
| 5,750,553 A | 5/1998 | Claussner | 548/321.1 X |

FOREIGN PATENT DOCUMENTS

| | | |
|---|---|---|
| DE | 19 40 032 A1 | 3/1970 |
| DE | 19 58 183 A1 | 6/1970 |
| DE | 21 00 800 A1 | 7/1971 |
| EP | 0 091 596 A1 | 10/1983 |
| EP | 0 343 643 A1 | 11/1989 |
| EP | 0 545 478 A1 | 6/1993 |
| WO | WO 95 18794 A1 | 7/1995 |

OTHER PUBLICATIONS

Agric. Biol. Chem. 1982, 46, 2755–8 Takayama et al.
J. Pharm. Sci. 1984, 73, 553–8 Halim et al.
Monatshefte für Chemie, 1994, 125, 1437–1442 Li et al.

* cited by examiner

*Primary Examiner*—Floyd D. Higel
(74) *Attorney, Agent, or Firm*—Robert P. Raymond; Alan R. Stempel; Mary-Ellen M. Devlin

(57) ABSTRACT

A method treating or preventing inflammatory and immune cell-mediated diseases by the administration of certain novel and known small molecules. Exemplary of the novel compounds are those of the following structural formulas:

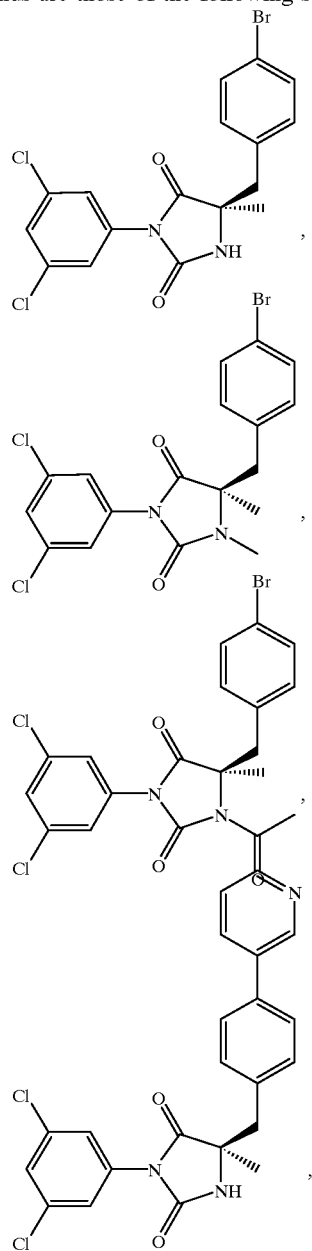

-continued
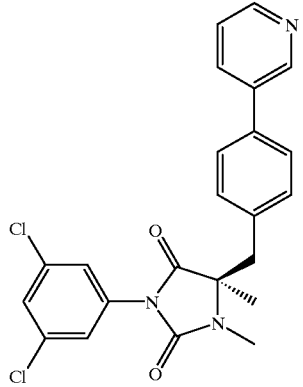
and
-continued
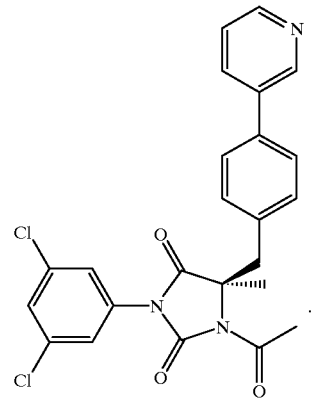
12 Claims, No Drawings

PHENYLPYRROLIDINES, PHENYLIMIDAZOLIDINES, 3-PHENYL-1,3-OXIZOLIDINES AND 3-PHENYL-1,3-THIAZOLIDINES AND THEIR USE IN THE TREATMENT OF INFLAMMATORY DISEASE

RELATED APPLICATIONS

This application is a continuation-in-part of International Application No. PCT/US98/04254, filed Mar. 3, 1998, and U.S. application Ser. No. 09/033,148, filed Mar. 2, 1998 now abandoned. The benefit of prior provisional application Serial Number 60/040,011, filed on Mar. 3, 1997, is hereby claimed.

FIELD OF THE INVENTION

The present invention relates generally to a series of novel small molecules, their synthesis and their use in the treatment of inflammatory disease. The invention further relates to the use of similar, but known, compounds in the treatment of inflammatory disease.

BACKGROUND OF THE INVENTION

Research spanning the last decade has helped to elucidate the molecular events attending cell-cell interactions in the body, especially those events involved in the movement and activation of cells in the immune system. See generally, Springer, T. Nature, 1990, 346, 425–434. Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. Adv. Pharmacol. 1994,25:117–138 and Diamond, M.; Springer, T. Current Biology, 1994, 4, 506–532.

A group of individuals has been identified which lack the appropriate expression of Leukointegrins, a condition termed "Leukocyte Adhesion Deficiency" (Anderson, D. C.; et al., Fed. Proc. 1985, 44, 2671–2677 and Anderson, D. C.; et al., J. Infect. Dis. 1985, 152, 668–689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11 /ICAM-1 interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; Immunology Today, 1994, 15,251–255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: Adhesion Molecules; Wegner, C. D., Ed.; 1994, 1–38, Cosimi, C. B.; et al., J. Immunol. 1990, 144, 4604–4612 and Kavanaugh, A.; et al., Arthritis Rheum. 1994, 37, 992–1004) and antibodies directed against LFA-1 have demonstrated immunosuppressive effects in bone marrow transplantation and in the prevention of early rejection of renal allografts (Fischer, A.; et al., Lancet, 1989, 2, 1058–1060 and Le Mauff, B.; et al., Transplantation, 1991, 52, 291–295).

It has also been demonstrated that a recombinant soluble form of ICAM-1 can act as an inhibitor of the ICAM-1 interaction with LFA-1. Soluble ICAM-1 acts as a direct antagonist of CD18, CD11 /ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., J. Immunol. 1993, 151, 7224 and Roep, B. O.; et al., Lancet, 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to antagonize the binding of the CAMs to the Leukointegrins would make preferable therapeutic agents. To date, however, no small molecules acting as direct antagonists have been reported.

Several small molecules have been described in the literature which affect the interaction of CAMs and Leukointegrins. A natural product isolated from the root of Trichilia rubra was found to be inhibitory in an in vitro cell binding assay (Musza, L. L.; et al., Tetrahedron, 1994, 50, 11369–11378). One series of molecules (Boschelli, D. H.; et al., J. Med. Chem. 1994, 37, 717 and Boschelli, D. H.; et al., J. Med. Chem. 1995, 38, 4597–4614) was found to be orally active in a reverse passive Arthus reaction, an induced model of inflammation that is characterized by neutrophil accumulation (Chang, Y. H.; et al., Eur. J. Pharmacol. 1992, 69, 155–164). Another series of molecules was also found to be orally active in a delayed type hypersensitivity reaction in rats (Sanfilippo, P. J.; et al., *J. Med. Chem.* 1995, 38, 1057–1059). All of these molecules appear to act nonspecifically, either by inhibiting the transcription of ICAM-1 along with other proteins or act intracellularly to inhibit the activation of the Leukointegrins by an unknown mechanism. None of the molecules directly antagonize the interaction of the CAMs with the Leukointegrins. Due to lack of potency, lack of selectivity and lack of a specific mechanism of action, the described small molecules are not likely to be satisfactory for therapeutic use.

Based on the status of the prior art, there remains a clear need for therapeutically useful small molecules having the ability to antagonize the interaction of CAMs and Leukointegrins.

SUMMARY OF THE INVENTION

A first aspect of the invention comprises a method for treating or preventing inflammatory and immune cell-mediated disease(s) by the administration of certain novel and known small molecules. These compounds act by inhibiting the interaction of cellular adhesion molecules, specifically by antagonizing the binding of human intercellular adhesion molecules (including, for example, ICAM-1, ICAM-2 and ICAM-3) to the Leukointegrins (including, for example, CD18/CD11a and CD18/CD11b). A second aspect of the invention comprises novel small molecules having the above-noted therapeutic activities. A third aspect of the invention comprises methods for making these novel compounds. A final aspect of the invention comprises pharmaceutical compositions comprising the above-mentioned compounds suitable for the prevention or treatment of inflammatory and immune cell-mediated condition(s).

DETAILED DESCRIPTION OF THE INVENTION

In its first aspect, the invention comprises a method for treating or preventing inflammatory and immune cell-mediated diseases by the administration of certain novel and known small molecules of the formula I

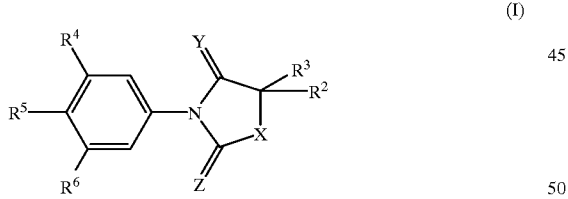

(I)

wherein:
  Y is an oxygen or sulfur atom;
  Z is an oxygen or sulfur atom;
  X is a divalent group of the formula >CHR$^1$, >NR$^1$, >CHSO$_2$R$^1$, or >NSO$_2$R$^1$, or an oxygen or sulfur atom, wherein R$^1$ is:
    (A) a hydrogen atom,
    (B) branched or unbranched alkyl of 1 to 6 carbon atoms or cycloalkyl of 3 to 6 carbon atoms, which alkyl or cycloakyl group may be mono- or polysubstituted with:
      (i) halogen,
      (ii) oxo,
      (iii) aryl, which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:
      (a) alkyl of 1 to 3 carbon atoms,
      (b) —COOH,
      (c) —SO$_2$OH,
      (d) —PO(OH)$_2$,
      (e) a group of the formula —COOR$^7$, wherein R$^7$ is straight or branched alkyl of 1 to 5 carbon atoms or cycloalkyl of 3 to 5 carbon atoms,
      (f) a group of the formula —NR$^8$R$^9$, wherein R$^8$ and R$^9$ are each independently a hydrogen atom, alkyl of 1 to 6 carbon atoms, cycloalkyl of 3 to 6 carbon atoms or acyl of 1 to 7 carbon atoms, or wherein R$^8$ and R$^9$ constitute a saturated hydrocarbon bridge of 3 to 5 carbon atoms which together with the nitrogen atom between them form a heterocyclic ring,
      (g) a group of the formula —CONR$^{10}$R$^{11}$, wherein R$^{10}$ and R$^{11}$ are each independently a hydrogen atom, alkyl of 1 to 6 carbon atoms or cycloalkyl of 3 to 6 carbon atoms, or wherein R$^{10}$ and R$^{11}$ constitute a saturated hydrocarbon bridge of 3 to 5 carbon atoms which together with the nitrogen atom between them form a heterocyclic ring,
      (h) a group of the formula —OR$^{12a}$, wherein R$^{12a}$ is a hydrogen atom, or an alkyl or acyl group of 1 to 7 carbon atoms,
      (i) a group of the formula —SR$^{12b}$, wherein R$^{12b}$is a hydrogen atom, or an alkyl or acyl group of 1 to 7 carbon atoms,
      (j) cyano, or
      (k) an amidino group of the formula

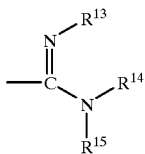

wherein R$^{13}$, R$^{14}$ and R$^{15}$ are each, independently, a hydrogen atom or alkyl of 1 to 3 carbon atoms and wherein two of R$^{13}$, R$^{14}$ and R$^{15}$ may additionally constitute a saturated hydrocarbon bridge of 3 to 5 carbon atoms which together with the nitrogen atom(s) between them form a heterocyclic ring,
      (iv) a group of the formula —COOR$^{16}$, wherein R$^{16}$ is straight or branched alkyl of 1 to 7 carbon atoms or cycloalkyl of 3 to 6 carbon atoms,
      (v) cyano,
      (vi) a group of the formula —CONR$^{17}$R$^{18}$, wherein R$^{17}$ and R$^{18}$ are each, independently, a hydrogen atom, alkyl of 1 to 6 carbon atoms or cycloalkyl of 3 to 6 carbon atoms, or wherein $R^{17}$ and $R^{18}$ constitute a saturated hydrocarbon bridge of 3 to 5 carbon atoms which together with the nitrogen atom between them form a heterocyclic ring, (vii) a group of the formula —$OR^{19}$, wherein $R^{19}$ is a hydrogen atom, or an alkyl or acyl group of 1 to 7 carbon atoms, (viii) a group of the formula —$SR^{20}$, wherein $R^{20}$ is a hydrogen atom, or an allyl or acyl group of 1 to 7 carbon atoms, (ix) a group of the formula —$NR^{21}R^{22}$, wherein $R^{21}$ and $R^{22}$ are each, independently, (a) a hydrogen atom, (b) alkyl or acyl of 1 to 7 carbon atoms or cycloalkyl of 3 to 7 carbon atoms, (c) a group of the formula —$CH_2)_m COOH$, wherein m is 0, 1 or 2, or (d) a group of the formula —$CH_2)_n COOR^{23}$, wherein n is 0, 1 or 2, wherein $R^{23}$ is straight or branched alkyl of 1 to 6 carbon atoms, or wherein $R^{21}$ and $R^{22}$ constitute a saturated hydrocarbon bridge of 3 to 5 carbon atoms which together with the nitrogen atom between them form a heterocyclic ring, or (x) a quaternary group of the formula

wherein $R^{24}$, $R^{25}$ and $R^{26}$ are each, independently, a branched or unbranched alkyl group of 1 to 7 carbon atoms and $Q^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an anilino group of the formula

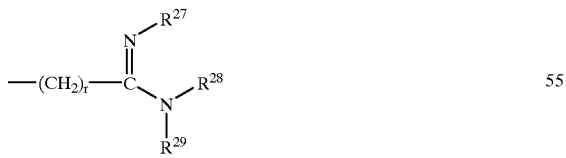

wherein r is 2, 3, 4, 5 or 6, and $R^{27}$, $R^{28}$ and $R^{29}$ are each, independently, a hydrogen atom or alkyl of I to 3 carbon atoms, and wherein two of $R^{27}$, $R^{28}$ and $R^{29}$ may additionally constitute a saturated hydrocarbon bridge of 3 to 5 carbon atoms which together with the nitrogen atom(s) between them form a heterocyclic ring, (G) an guanidino group of the formula

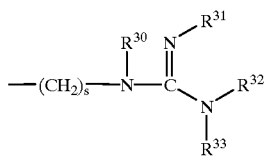

wherein s is 2, 3, 4, 5 or 6, and $R^{30}$, $R^{31}$, $R^{32}$ and $R^{33}$ are each, independently, a hydrogen atom or alkyl of 1 to 3 carbon atoms, and wherein two of $R^{30}$, $R^{31}$, $R^{32}$ and $R^{33}$ may additionally constitute a saturated hydrocarbon bridge of 3 to 5 carbon atoms which together with the nitrogen atom(s) between them form a heterocyclic ring, (H) piperidyl, wherein the nitrogen atom of said group is optionally substituted with:

(i) alkyl of 1 to 3 carbon atoms, (ii) a carboxylic ester group of 2 to 7 carbon atoms, (iii) a carboxylic acid group of 2 to 5 carbon atoms, (iv) a phosphonic acid group of 1 to 6 carbon atoms, or (v) a sulfonic acid groups of 1 to 6 carbon atoms, or (I) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:

(i) alkyl of 1 to 3 carbon atoms, (ii) —COOH, (iii) —$SO_2OH$, (iv) —$PO(OH)_2$, (v) a group of the formula —$COOR^7$, wherein $R^7$ is straight or branched alkyl of 1 to 5 carbon atoms or cycloalkyl of 3 to 5 carbon atoms, (vi) a group of the formula —$NR^8R^9$, wherein $R^8$ and $R^9$ are each, independently, a hydrogen atom, alkyl of 1 to 6 carbon atoms, cycloalkyl of 3 to 6 carbon atoms or acyl of 1 to 7 carbon atoms, or wherein $R^8$ and $R^9$ constitute a saturated hydrocarbon bridge of 3 to 5 carbon atoms which together with the nitrogen atom between them form a heterocyclic ring, (vii) a group of the formula —$CONR^{10}R^{11}$, wherein $R^{10}$ and $R^{11}$ are each, independently, a hydrogen atom, alkyl of 1 to 6 carbon atoms or cycloalkyl of 3 to 6 carbon atoms, or wherein $R^{10}$ and $R^{11}$ constitute a saturated hydrocarbon bridge of 3 to 5 carbon atoms which together with the nitrogen atom between them form a heterocyclic ring, (viii) a group of the formula —$OR^{12a}$, wherein $R^{12a}$ is a hydrogen atom, or an alkyl or acyl group of 1 to 7 carbon atoms, (ix) a group of the formula —SR$^{12b}$, wherein R$^{12b}$ is a hydrogen atom, or an alkyl or acyl group of 1 to 7 carbon atoms,
(x) cyano, or
(xi) an amidino group of the formula

wherein R$^{13}$, R$^{14}$ and R$^{15}$ are each, independently, a hydrogen atom or alkyl of 1 to 3 carbon atoms, and wherein two of R$^{13}$, R$^{14}$ and R$^{15}$ may additionally constitute a saturated hydrocarbon bridge of 3 to 5 carbon atoms which together with the nitrogen atom(s) between them form a heterocyclic ring;

R$^2$ is:
(A) a hydrogen atom, or
(B) branched or unbranched alkyl of 1 to 3 carbon atoms or cycloalkyl of 3 to 5 carbon atoms wherein said alkyl or cycloalkyl group may optionally be substituted with:
  (i) a group of the formula —OR$^{34}$, wherein R$^{34}$ is a hydrogen atom, or an alkyl or acyl group of 1 to 7 carbon atoms, or
  (ii) a group of the formula —NR$^{35}$R$^{36}$, wherein R$^{35}$ and R$^{36}$ are each, independently, a hydrogen atom, alkyl of 1 to 2 carbon atoms, or acyl of 1 to 2 carbon atoms;

R$^3$ is a group of the formula —(CR$^{357l}$ $^{R38}$)$_x$(CR$^{39}$R$^{40}$)$_y$R$^{41}$, wherein;
x and y are each independently 0 or 1,
R$^{37}$, R$^{38}$ and R$^{39}$ are each, independently:
(A) a hydrogen atom,
(B) a group of the formula —OR$^{42}$, wherein R$^{42}$ is a hydrogen atom, or an alkyl or acyl group of 1 to 7 carbon atoms, or
(C) branched or unbranched alkyl of 1 to 3 carbon atoms or cycloalkyl of 3 to 5 carbon atoms, R$^{40}$ is:
(A) a hydrogen atom,
(B) a group of the formula —OR$^{42}$, wherein R$^{42}$ is a hydrogen atom, or an alkyl or acyl group of 1 to 7 carbon atoms,
(C) branched or unbranched alkyl of 1 to 3 carbon atoms or cycloalkyl of 3 to 5 carbon atoms, or
(D) aryl which is selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3,6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:
(i) R$^{43}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-midazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:
(a) branched or unbranched alkyl of 1 to 6 carbon atoms or cycloalkyl of 3 to 6 carbon atoms, which alkyl or cycloakyl group may be mono- or polysubstituted with halogen or oxo,
(b) —COOH,
(c) —SO$_2$OH,
(d) —PO(OH)$_2$,
(e) a group of the formula —COOR$^{44}$, wherein R$^{44}$ is straight or branched alkyl of 1 to 5 carbon atoms or cycloalkyl of 3 to 5 carbon atoms,
(f) a group of the formula —NR$^{45}$R$^{46}$, wherein R$^{45}$ and R$^{46}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{45}$ and R$^{46}$ constitute a saturated hydrocarbon bridge of 3 to 5 carbon atoms which together with the nitrogen atom between them form a heterocyclic ring,
(g) a group of the formula —CONR$^{47}$R$^{48}$, wherein R$^{47}$ and R$^{48}$ are each independently a hydrogen atom, alkyl or fluoroalkyl of 1 to 6 carbon atoms or cycloalkyl of 3 to 6 carbon atoms, or wherein R$^{47}$ and R$^{48}$ constitute a saturated hydrocarbon bridge of 3 to 5 carbon atoms which together with the nitrogen atom between them form a heterocyclic ring,
(h) a group of the formula —OR$^{49}$, wherein R$^{49}$ is a hydrogen atom, or an alkyl, fluoroalkyl or acyl group of 1 to 7 carbon atoms,
(i) a group of the formula —SR$^{50}$, wherein R$^{50}$ is a hydrogen atom, or an alkyl, fluoroalkyl or acyl group of 1 to 7 carbon atoms,
(j) cyano,
(k) nitro, (l) an amidino group of the formula

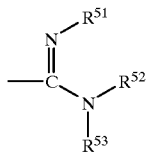

wherein $R^{51}$, $R^{52}$ and $R^{53}$ are each, independently, a hydrogen atom or alkyl of 1 to 3 carbon atoms, and wherein two of $R^{51}$, $R^{52}$ and $R^{53}$ may additionally constitute a saturated hydrocarbon bridge of 3 to 5 carbon atoms which together with the nitrogen atom(s) between them form a heterocyclic ring, or
(m) halogen,
(ii) methyl, which may be mono- or polysubstituted with fluorine atoms and additionally may be monosubstituted with $R^{43}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$COOR^{54}$, wherein $R^{54}$ is straight or branched alkyl of 1 to 5 carbon atoms or cycloalkyl of 3 to 5 carbon atoms,
(v) a group of the formula —$NR^{55}R^{56}$, wherein $R^{55}$ and $R^{56}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{55}$ and $R^{56}$ constitute a saturated hydrocarbon bridge of 3 to 5 carbon atoms which together with the nitrogen atom between them form a heterocyclic ring, and wherein one of $R^{55}$ and $R^{56}$ may additionally be the group $R^{43}$,
(vi) a group of the formula —$CONR^{57}R^{58}$, wherein $R^{57}$ and $R^{58}$ are each, independently, a hydrogen atom, alkyl or fluoroalkyl of 1 to 6 carbon atoms or cycloalkyl of 3 to 6 carbon atoms, or wherein $R^{57}$ and $R^{58}$ constitute a saturated hydrocarbon bridge of 3 to 5 carbon atoms which together with the nitrogen atom between them form a heterocyclic ring, and wherein one of $R^{57}$ and $R^{58}$ may additionally be the group $R^{43}$,
(vii) a group of the formula —$COR^{59}$, wherein $R^{59}$ is a hydrogen atom, straight or branched alkyl of 1 to 5 carbon atoms, cycloalkyl of 3 to 5 carbon atoms or $R^{43}$,
(viii) a group of the formula —$OR^{60}$, wherein $R^{60}$ is a hydrogen atom, an alkyl, fluoroalkyl or acyl group of 1 to 7 carbon atoms, or $R^{43}$,
(ix) a group of the formula —$SR^{61}$, wherein $R^{61}$ is a hydrogen atom, an alkyl, fluoroalkyl or acyl group of 1 to 7 carbon atoms, or $R^{43}$,
(x) cyano,
(xi) nitro, or
(xii) halogen,
$R^{41}$ is:
aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]faranyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said aryl group may be optionally and independently replaced with:
(A) $R^{62}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said aryl group may be optionally and independently replaced with:
(i) branched or unbranched alkyl of 1 to 6 carbon atoms or cycloalkyl of 3 to 6 carbon atoms, which alkyl or cycloakyl group may be mono- or polysubstituted with halogen or oxo,
(ii) —COOH,
(iii) —$SO_2OH$,
(iv) —$PO(OH)_2$,
(v) a group of the formula —$COOR^{63}$, wherein $R^{63}$ is straight or branched alkyl of 1 to 5 carbon atoms or cycloalkyl of 3 to 5 carbon atoms,
(vi) a group of the formula —$NR^{64}R^{65}$, wherein $R^{64}$ and $R^{65}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring,
(vii) a group of the formula —$CONR^{66}R^{67}$, wherein $R^{66}$ and $R^{67}$ are each, independently, a hydrogen atom, alkyl or fluoroalkyl of 1 to 6 carbon atoms or cycloalkyl of 3 to 6 carbon atoms, or wherein $R^{66}$ and $R^{67}$ constitute a saturated hydrocarbon bridge of 3 to 5 carbon atoms which together with the nitrogen atom between them form a heterocyclic ring,
(viii) a group of the formula —$OR^{68}$, wherein $R^{68}$ is a hydrogen atom, or an alkyl, fluoroalkyl or acyl group of 1 to 7 carbon atoms, (ix) a group of the formula —SR⁶⁹, wherein R⁶⁹ is a hydrogen atom, or an alkyl, fluoroalkyl or acyl group of 1 to 7 carbon atoms,
(x) cyano,
(xi) nitro, or
(xii) an amidino group of the formula

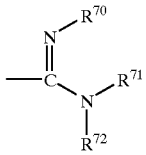

wherein $R^{70}$, $R^{71}$ and $R^{72}$ are each, independently, a hydrogen atom or alkyl or fluoroalkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring, or
(xiii) halogen,
(B) methyl, which may be mono- or polysubstituted with fluorine atoms and additionally may be monosubstituted with $R^{62}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —COOR⁷³, wherein $R^{73}$ is straight or branched alkyl of 1 to 5 carbon atoms or cycloalkyl of 3 to 5 carbon atoms,
(E) a group of the formula —NR⁷⁴R⁷⁵, wherein $R^{74}$ and $R^{75}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{74}$ and $R^{75}$ constitute a saturated hydrocarbon bridge of 3 to 5 carbon atoms which together with the nitrogen atom between them form a heterocyclic ring, and wherein one of $R^{74}$ and $R^{75}$ may additionally be the group $R^{62}$,
(F) a group of the formula —CONR⁷⁶R⁷⁷, wherein $R^{76}$ and $R^{77}$ are each, independently, a hydrogen atom, alkyl or fluoroallyl of 1 to 6 carbon atoms or cycloalkyl of 3 to 6 carbon atoms, or wherein $R^{76}$ and $R^{77}$ constitute a saturated hydrocarbon bridge of 3 to 5 carbon atoms which together with the nitrogen atom between them form a heterocyclic ring, and wherein one of $R^{76}$ and $R^{77}$ may additionally be the group $R^{62}$,
(G) a group of the formula —COR⁷⁸, wherein $R^{78}$ is a hydrogen atom, straight or branched alkyl of 1 to 5 carbon atoms, cycloalkyl of 3 to 5 carbon atoms or $R^{62}$,
(H) a group of the formula —OR⁷⁹, wherein $R^{79}$ is a hydrogen atom, an alkyl, fluoroalkyl or acyl group of 1 to 7 carbon atoms, or $R^{62}$,
(I) a group of the formula —SR⁸⁰, wherein $R^{80}$ is a hydrogen atom, an alkyl, fluoroalkyl or acyl group of 1 to 7 carbon atoms, or $R^{62}$,
(J) cyano,
(K) nitro, or
(L) halogen;
$R^4$ is Cl or trifluoromethyl; and, $R^5$ and $R^6$ are each, independently, a hydrogen, fluorine, chlorine, bromine or iodine atom, methyl or trifluoromethyl;
or a pharmaceutically acceptable salt thereof.

As mentioned before, some of the compounds embraced by the above-described genus are known and have been described in U.S. Pat. No. 3,668,217; U.S. Pat. No. 4,944,791; U.S. Pat. No. 3,741,981; Li, W.-Y; et al., *J. Pharm. Sci.* 1984, 73, 553–558 and, Abd El Halim, M. S.; et al., *Monatshefte für Chemie*, 1994, 125, 1437–1442.

In its second aspect, the invention comprises novel compounds of the formula I

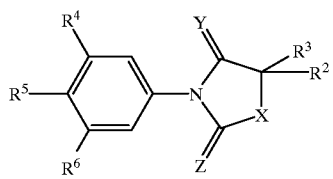

(I)

wherein X, Y, Z, $R^2$, $R^3$, $R^4$, $R^5$ and $R^6$ are defined as above except that, in the moiety $R^3$, at least one of the hydrogen atoms of the aryl group $R^{41}$ is necessarily, rather than optionally, replaced by:

(A) $R^{62}$, which is aryl selected from the class consisting of phenyl, 2-naphtyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl or 2-, 6- and 7-quinazolinyl,
wherein one or more of the hydrogen atoms of said aryl group may be optionally and independently replaced with:
(i) branched or unbranched alkyl of 1 to 6 carbon atoms or cycloalkyl of 3 to 6 carbon atoms, which alkyl or cycloakyl group may be mono- or polysubstituted with halogen or oxo,
(ii) —COOH,
(iii) —SO2OH,
(iv) —PO(OH)₂,
(v) a group of the formula COOR⁶³, wherein $R^{63}$ is straight or branched alkyl of 1 to 5 carbon atoms or cycloalkyl of 3 to 5 carbon atoms,
(vi) a group of the formula —NR⁶⁴R⁶⁵, wherein $R^{64}$ and $R^{65}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring,
(vii) a group of the formula —CONR⁶⁶R⁶⁷, wherein $R^{66}$ and $R^{67}$ are each, independently, a hydrogen atom, alkyl or fluoroalkyl of 1 to 6 carbon atoms or cycloalkyl of 3 to 6 carbon atoms, or wherein $R^{66}$ and $R^{67}$ constitute a saturated hydrocarbon bridge of 3 to 5 carbon atoms which together with the nitrogen atom between them form a heterocyclic ring, (viii) a group of the formula —$OR^{68}$, wherein $R^{68}$ is a hydrogen atom, or an alkyl, fluoroalkyl or acyl group of 1 to 7 carbon atoms, (ix) a group of the formula —$SR^{69}$, wherein $R^{69}$ is a hydrogen atom, or an alkyl, fluoroalkyl or acyl group of 1 to 7 carbon atoms, (x) cyano, (xi) nitro, (xii) an amidino group of the formula

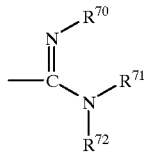

wherein $R^{70}$, $R^{71}$ and $R^{72}$ are each, independently, a hydrogen atom or alkyl or fluoroalkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring, or (xiii) halogen, (B) methyl, which may be mono- or polysubstituted with fluorine atoms and additionally may be monosubstituted with $R^{62}$, (C) branched or unbranched alkyl of 2 to 6 carbon atoms or cycloalkyl of 3 to 6 carbon atoms, which alkyl or cycloakyl group may be mono- or polysubstituted with halogen or oxo, (D) a group of the formula —$COOR^{73}$, wherein $R^{73}$ is straight or branched alkyl of 1 to 5 carbon atoms or cycloalkyl of 3 to 5 carbon atoms, (E) a group of the formula —$NR^{74}R^{75}$, wherein $R^{74}$ and $R^{75}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{74}$ and $R^{75}$ constitute a saturated hydrocarbon bridge of 3 to 5 carbon atoms which together with the nitrogen atom between them form a heterocyclic ring, and wherein one of $R^{74}$ and $R^{75}$ may additionally be the group $R^{62}$, (F) a group of the formula —$CONR^{76}R^{77}$, wherein $R^{76}$ and $R^{77}$ are each, independently, a hydrogen atom, alkyl or fluoroalkyl of 1 to 6 carbon atoms or cycloalkyl of 3 to 6 carbon atoms, or wherein $R^{76}$ and $R^{77}$ constitute a saturated hydrocarbon bridge of 3 to 5 carbon atoms which together with the nitrogen atom between them form a heterocyclic ring, and wherein one of $R^{76}$ and $R^{77}$ may additionally be the group $R^{62}$, (G) a group of the formula —$COR^{78}$, wherein $R^{78}$ is a hydrogen atom, straight or branched alkyl of 1 to 5 carbon atoms, cycloalkyl of 3 to 5 carbon atoms or $R^{62}$, (H) a group of the formula —$OR^{79}$, wherein $R^{79}$ is a hydrogen atom, an alkyl fluoroalkyl or acyl group of 1 to 7 carbon atoms, or $R^{62}$, (I) a group of the formula —$SR^{80}$, wherein $R^{80}$ is a hydrogen atom, an alkyl, fluoroalkyl or acyl group of 1 to 7 carbon atoms, or $R^{62}$, (J) cyano, (K) nitro, or (L) halogen;

or pharmaceutically acceptable salts thereof.

Preferred novel compounds of formula I are those wherein:

Y is an oxygen or sulfur atom;

Z is an oxygen or sulfur atom;

X is a divalent group of the formula >$CHR^1$, >$NR^1$, >$CHSO_2R^1$, or >$NSO_2R^1$, or an oxygen or sulfur atom, wherein $R^1$ is:

(A) a hydrogen atom, (B) branched or unbranched alkyl of 1 to 6 carbon atoms or cycloalkyl of 3 to 6 carbon atoms, which alkyl or cycloakyl group may be monosubstituted with:

(i) halogen, (ii) oxo, (iii) aryl selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:

(a) alkyl of 1 to 3 carbon atoms, (b) —COOH, (c) —$SO_2OH$, (d) —$PO(OH)_2$, (e) a group of the formula —$COOR^7$, wherein $R^7$ is straight or branched alkyl of 1 to 5 carbon atoms or cycloalkyl of 3 to 5 carbon atoms, (f) a group of the formula —$NR^8R^9$, wherein $R^8$ and $R^9$ are each, independently, a hydrogen atom, alkyl of 1 to 6 carbon atoms, cycloalkyl of 3 to 6 carbon atoms or acyl of 1 to 7 carbon atoms, or wherein $R^8$ and $R^9$ constitute a saturated hydrocarbon bridge of 3 to 5 carbon atoms which together with the nitrogen atom between them form a heterocyclic ring, (g) a group of the formula —$CONR^{10}R^{11}$, wherein $R^{10}$ and $R^{11}$ are each, independently, a hydrogen atom, alkyl of 1 to 6 carbon atoms or cycloalkyl of 3 to 6 carbon atoms, or wherein $R^{10}$ and $R^{11}$ constitute a saturated hydrocarbon bridge of 3 to 5 carbon atoms which together with the nitrogen atom between them form a heterocyclic ring, (h) a group of the formula —$OR^{12a}$, wherein $R^{12a}$ is a hydrogen atom, or an alkyl or acyl group of 1 to 7 carbon atoms, (i) a group of the formula —$SR^{12b}$, wherein $R^{12b}$ is a hydrogen atom, or an alkyl or acyl group of 1 to 7 carbon atoms, (j) cyano, or
(k) an amidino group of the formula

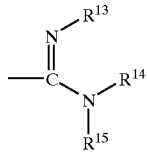

wherein $R^{13}$, $R^{14}$ and $R^{15}$ are each, independently, a hydrogen atom or alkyl of 1 to 3 carbon atoms and wherein two of $R^{13}$, $R^{14}$ and $R^{15}$ may additionally constitute a saturated hydrocarbon bridge of 3 to 5 carbon atoms which together with the nitrogen atom(s) between them form a heterocyclic ring, (iv) a group of the formula —COOR$^{16}$, wherein $R^{16}$ is straight or branched alkyl of 1 to 7 carbon atoms or cycloalkyl of 3 to 6 carbon atoms, (v) cyano, (vi) a group of the formula —CONR$^{17}$R$^{18}$, wherein $R^{17}$ and $R^{18}$ are each, independently, a hydrogen atom, alkyl of 1 to 6 carbon atoms or cycloalkyl of 3 to 6 carbon atoms, or wherein $R^{17}$ and $R^{18}$ constitute a saturated hydrocarbon bridge of 3 to 5 carbon atoms which together with the nitrogen atom between them form a heterocyclic ring, (vii) a group of the formula —OR$^{19}$, wherein $R^{19}$ is a hydrogen atom, or an alkyl or acyl group of 1 to 7 carbon atoms, (viii) a group of the formula —SR$^{20}$, wherein $R^{20}$ is a hydrogen atom, or an alkyl or acyl group of 1 to 7 carbon atoms, (ix) a group of the formula —NR$^{21}$R$^{22}$, wherein $R^{21}$ and $R^{22}$ are each, independently:
(a) a hydrogen atom,
(b) alkyl or acyl of 1 to 7 carbon atoms or cycloalkyl of 3 to 7 carbon atoms,
(c) a group of the formula {(CH$_2$)$_m$COOH, wherein m is 0, 1 or 2, or
(d) a group of the formula —(CH$_2$)$_n$COOR$^{23}$, wherein n is 0, 1 or 2, wherein $R^{23}$ is straight or branched alkyl of 1 to 6 carbon atoms, or wherein $R^{21}$ and $R^{22}$ constitute a saturated hydrocarbon bridge of 3 to 5 carbon atoms which together with the nitrogen atom between them form a heterocyclic ring, or (x) a quaternary group of the formula

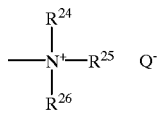

wherein $R^{24}$, $R^{25}$ and $R^{26}$ are each, independently, a branched or unbranched alkyl group of 1 to 7 carbon atoms and Q$^-$ is a chlorine, bromine or iodine counterion, (C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms, (F) an amidino group of the formula

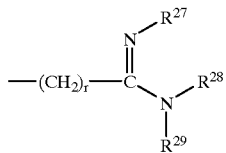

wherein r is 2, 3, 4, 5 or 6, and $R^{27}$, $R^{28}$ and $R^{29}$ are each, independently, a hydrogen atom or alkyl of 1 to 3 carbon atoms and wherein two of $R^{27}$, $R^{28}$ and $R^{29}$ may additionally constitute a saturated hydrocarbon bridge of 3 to 5 carbon atoms which together with the nitrogen atom(s) between them form a heterocyclic ring, (G) an guanidino group of the formula

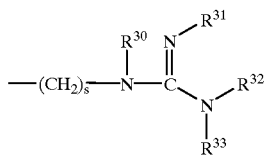

wherein s is 2, 3, 4, 5 or 6, and $R^{30}$, $R^{31}$, $R^{32}$ and $R^{33}$ are each independently a hydrogen atom or alkyl of 1 to 3 carbon atoms and wherein two of $R^{30}$, $R^{31}$, $R^{32}$ and $R^{33}$ may additionally constitute a saturated hydrocarbon bridge of 3 to 5 carbon atoms which together with the nitrogen atom(s) between them form a heterocyclic ring, or (H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid group of 1 to 6 carbon atoms;

$R^2$ is:
(A) a hydrogen atom, or
(B) methyl;

$R^3$ is a group of the formula —CH$_2$R$^{41}$, wherein:
$R^{41}$ is:
aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2,- 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group are necessarily and independently replaced with:
(A) $R^{62}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said aryl group may be optionally and independently replaced with:
(i) branched or unbranched alkyl of 1 to 6 carbon atoms or cycloalkyl of 3 to 6 carbon atoms, which alkyl or cycloakyl group may be mono- or polysubstituted with halogen or oxo,
(ii) —COOH,
(iii) —$SO_2OH$,
(iv) —$PO(OH)_2$,
(v) a group of the formula —$COOR^{63}$, wherein $R^{63}$ is straight or branched alkyl of 1 to 5 carbon atoms or cycloalkyl of 3 to 5 carbon atoms,
(vi) a group of the formula —$NR^{64}R^{65}$, wherein $R^{64}$ and $R^{65}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{64}$ and $R^{65}$ constitute a saturated hydrocarbon bridge of 3 to 5 carbon atoms which together with the nitrogen atom between them form a heterocyclic ring,
(vii) a group of the formula —$CONR^{66}R^{67}$, wherein $R^{66}$ and $R^{67}$ are each, independently, a hydrogen atom, alkyl or fluoroalkyl of 1 to 6 carbon atoms or cycloalkyl of 3 to 6 carbon atoms, or wherein $R^{66}$ and $R^{67}$ constitute a saturated hydrocarbon bridge of 3 to 5 carbon atoms which together with the nitrogen atom between them form a heterocyclic ring,
(viii) a group of the formula —$OR^{68}$, wherein $R^{68}$ is a hydrogen atom, or an alkyl, fluoroalkyl or acyl group of 1 to 7 carbon atoms,
(ix) a group of the formula —$SR^{69}$, wherein $R^{69}$ is a hydrogen atom, or an alkyl, fluoroalkyl or acyl group of 1 to 7 carbon atoms,
(x) cyano,
(xi) nitro, (xii) an amidino group of the formula

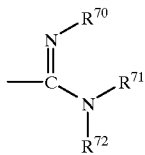

wherein $R^{70}$, $R^{71}$ and $R^{72}$ are each, independently, a hydrogen atom or alkyl or fluoroalkyl of 1 to 3 carbon atoms, and wherein two of $R^{70}$, $R^{71}$ and $R^{72}$ may additionally constitute a saturated hydrocarbon bridge of 3 to 5 carbon atoms which together with the nitrogen atom(s) between them form a heterocyclic ring, or
(xiii) halogen,
(B) methyl, which may be mono- or polysubstituted with fluorine atoms and additionally may be monosubstituted with $R^{62}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —$COOR^{73}$, wherein $R^{73}$ is straight or branched alkyl of 1 to 5 carbon atoms or cycloalkyl of 3 to 5 carbon atoms,
(E) a group of the formula —$NR^{74}R^{75}$, wherein $R^{74}$ and $R^{75}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{74}$ and $R^{75}$ constitute a saturated hydrocarbon bridge of 3 to 5 carbon atoms which together with the nitrogen atom between them form a heterocyclic ring, and wherein one of $R^{74}$ and $R^{75}$ may additionally be the group $R^{62}$,
(F) a group of the formula —$CONR^{76}R^{77}$, wherein $R^{76}$ and $R^{77}$ are each, independently, a hydrogen atom, alkyl or fluoroalkyl of 1 to 6 carbon atoms or cycloalkyl of 3 to 6 carbon atoms, or wherein $R^{76}$ and $R^{77}$ constitute a saturated hydrocarbon bridge of 3 to 5 carbon atoms which together with the nitrogen atom between them form a heterocyclic ring, and wherein one of $R^{76}$ and $R^{77}$ may additionally be the group $R^{62}$,
(G) a group of the formula —$COR^{78}$, wherein $R^{78}$ is a hydrogen atom, straight or branched alkyl of 1 to 5 carbon atoms, cycloalkyl of 3 to 5 carbon atoms or $R^{62}$,
(H) a group of the formula —$OR^{79}$, wherein $R^{79}$ is a hydrogen atom, an alkyl, fluoroalkyl or acyl group of 1 to 7 carbon atoms, or $R^{62}$,
(I) a group of the formula —$SR^{80}$, wherein $R^{80}$ is a hydrogen atom, an alkyl, fluoroalkyl or acyl group of 1 to 7 carbon atoms, or $R^{62}$,
(J) cyano,
(K) nitro, or
(L) halogen;
$R^4$ is Cl or trifluoromethyl; and,
$R^5$ and $R^6$ are each independently a hydrogen, fluorine, chlorine, bromine or iodine atom, methyl or trifluoromethyl;
or a pharmaceutically acceptable salt thereof.
More preferred are those novel compounds of formula I wherein:

Y is an oxygen atom;

Z is an oxygen atom;

X is a divalent group of the formula >CHR$^1$ or >NR$^1$, wherein R$^1$ is:
(A) a hydrogen atom,
(B) branched or unbranched alkyl of 1 to 6 carbon atoms or cycloalkyl of 3 to 6 carbon atoms, which alkyl or cycloakyl group may be monosubstituted with:
  (i) oxo,
  (ii) aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl,
  wherein one or more hydrogen atoms of said aryl group may be optionally and independently replaced with:
    (a) alkyl of 1 to 3 carbon atoms,
    (b) —COOH,
    (c) —SO$_2$OH,
    (d) —PO(OH)$_2$,
    (e) a group of the formula —COOR$^7$, wherein R$^7$ is straight or branched alkyl of 1 to 5 carbon atoms or cycloalkyl of 3 to 5 carbon atoms,
    (f) a group of the formula —NH$_2$,
    (g) a group of the formula —CONH$_2$,
    (h) a group of the formula —OR$^{12a}$, wherein R$^{12a}$ is a hydrogen atom or a methyl,
    (i) an amidino group of the formula

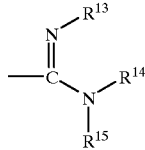

wherein R$^{13}$, R$^{14}$ and R$^{15}$ are each hydrogen atoms,
    (j) a group of the formula —COOR$^{16}$, wherein R$^{16}$ is straight or branched alkyl of 1 to 7 carbon atoms or cycloalkyl of 3 to 6 carbon atoms,
    (k) a group of the formula —OR$^{19}$, wherein R$^{19}$ is a hydrogen atom, or an alkyl or acyl group of 1 to 7 carbon atoms, or
    (l) a quaternary group of the formula

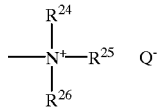

wherein R$^{24}$, R$^{25}$ and R$^{26}$ are each methyl and Q$^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

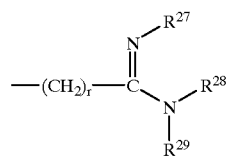

wherein r is 2, 3, 4, 5 or 6, and
  R$^{27}$, R$^{28}$ and R$^{29}$ are each hydrogen atoms,
(G) an guanidino group of the formula

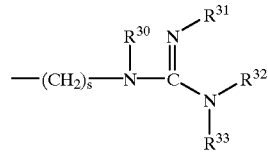

wherein s is 2, 3, 4, 5 or 6,
  R$^{30}$, R$^{31}$, R$^{32}$ and R$^{33}$ are each hydrogen atoms, or
(H) piperidyl, wherein the nitrogen atom of said group is optionally substituted with:
  (i) alkyl of 1 to 3 carbon atoms,
  (ii) a carboxylic ester group of 2 to 7 carbon atoms,
  (iii) a carboxylic acid group of 2 to 5 carbon atoms,
  (iv) a phosphonic acid group of 1 to 6 carbon atoms, or
  (v) a sulfonic acid group of 1 to 6 carbon atoms;

R$^2$ is:
(A) a hydrogen atom, or
(B) methyl;

R$^3$ is a group of the formula —CH$_2$R$^{41}$, wherein R$^{41}$ is
  aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl,
  wherein one or more of the hydrogen atoms of said aryl group are necessarily and independently replaced with:
  (A) R$^{62}$, which is aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl,
    wherein one or more of the hydrogen atoms of said aryl group may be optionally and independently replaced with:
    (i) methyl,
    (ii) —COOH,
    (iii) —SO$_2$OH,
    (iv) —PO(OH)$_2$,
    (v) a group of the formula —COOR$^{63}$, wherein R$^{63}$ is methyl,
    (vi) a group of the formula —NR$^{64}$R$^{65}$, wherein R$^{64}$ and R$^{65}$ are each, independently, a hydrogen atom or methyl,
    (vii) a group of the formula —CONR$^{66}$R$^{67}$, wherein R$^{66}$ and R$^{67}$ are each, independently, a hydrogen atom or methyl, (viii) a group of the formula —OR$^{68}$, wherein R$^{68}$ is a hydrogen atom or methyl,
(ix) a group of the formula —SR$^{69}$, wherein R$^{69}$ is a hydrogen atom or methyl,
(x) cyano,
(xi) nitro, or
(xii) halogen,
(B) methyl, which may be mono- or polysubstituted with fluorine atoms and which additionally may be monosubstituted with R$^{62}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —COOR$^{73}$, wherein R$^{73}$ is methyl,
(E) a group of the formula —NR$^{74}$R$^{75}$, wherein R$^{74}$ and R$^{75}$ are each, independently, a hydrogen atom or methyl, and wherein one of R$^{74}$ and R$^{75}$ may additionally be the group R$^{62}$,
(F) a group of the formula —CONR$^{76}$R$^{77}$, wherein R$^{76}$ and R$^{77}$ are each, independently, a hydrogen atom or methyl, and wherein one of R$^{76}$ and R$^{77}$ may additionally be the group R$^{62}$,
(G) a group of the formula —COR$^{78}$, wherein R$^{78}$ is a hydrogen atom, methyl or R$^{62}$,
(H) a group of the formula —OR$^{79}$, wherein R$^{79}$ is a hydrogen atom, methyl or R$^{62}$,
(I) a group of the formula —SR$^{80}$, wherein R$^{80}$ is a hydrogen atom, methyl or R$^{62}$,
(J) cyano,
(K) nitro, or
(L) halogen;
R$^4$ is Cl or trifluoromethyl;
R$^5$ is a hydrogen atom; and,
R$^6$ is Cl, or trifluoromethyl;
or a pharmaceutically acceptable salt thereof.

Even more preferred are those novel compounds of formula I wherein:
Y is an oxygen atom;
Z is an oxygen atom;
X is a divalent group of the formula >CHR$^1$ or >NR$^1$, wherein R$^1$ is:
(A) a hydrogen atom,
(B) branched or unbranched alkyl of 1 to 6 carbon atoms or cycloalkyl of 3 to 6 carbon atoms, which alkyl or cycloakyl group may be monosubstituted with:
(i) oxo,
(ii) aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl, wherein one or more hydrogen atoms of said aryl group may be optionally and independently replaced with:
(a) alkyl of 1 to 3 carbon atoms,
(b) —COOH,
(c) —SO$_2$OH,
(d) —PO(OH)$_2$,
(e) a group of the formula —COOR$^7$, wherein R$^7$ is straight or branched alkyl of 1 to 5 carbon atoms or cycloalkyl of 3 to 5 carbon atoms,
(f) a group of the formula —NH$_2$,
(g) a group of the formula —CONH$_2$,
(h) a group of the formula —OR$^{12a}$, wherein R$^{12a}$ is a hydrogen atom or a methyl,
(i) an amidino group of the formula

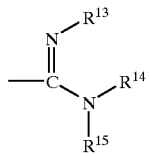

wherein R$^{13}$, R$^{14}$ and R$^{15}$ are each hydrogen atoms,
(j) a group of the formula —COOR$^{16}$, wherein R$^{16}$ is straight or branched alkyl of 1 to 7 carbon atoms or cycloalkyl of 3 to 6 carbon atoms,
(k) a group of the formula —OR$^{19}$, wherein R$^{19}$ is a hydrogen atom, or an alkyl or acyl group of 1 to 7 carbon atoms, or
(l) a quaternary group of the formula

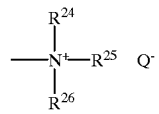

wherein R$^{24}$, R$^{25}$ and R$^{26}$ are each methyl and Q$^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

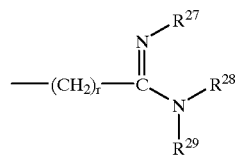

wherein r is 2, 3, 4, 5 or 6, and R$^{27}$, R$^{28}$ and R$^{29}$ are each hydrogen atoms,
(G) an guanidino group of the formula

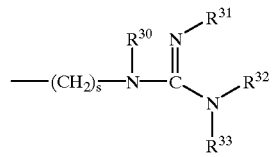

wherein s is 2, 3, 4, 5 or 6,
R$^{30}$, R$^{31}$, R$^{32}$ and R$^{33}$ are each hydrogen atoms, or
(H) piperidyl, wherein the nitrogen atom of said group is optionally substituted with:
(i) alkyl of 1 to 3 carbon atoms,
(ii) a carboxylic ester group of 2 to 7 carbon atoms,
(iii) a carboxylic acid group of 2 to 5 carbon atoms, (iv) a phosphonic acid group of 1 to 6 carbon atoms, or
(v) a sulfonic acid group of 1 to 6 carbon atoms;

$R^2$ is:
(A) a hydrogen atom, or
(B) methyl;

$R^3$ is a group of the formula —$CH_2R^{41}$, wherein $R^{41}$ is
aryl selected from the class consisting of phenyl, thiophenyl, pyridyl, pyrimidinyl, furyl, oxazolyl, thiazolyl, isoxazolyl, isothiazolyl, oxadiazolyl, thiadiazolyl, pyridazinyl, and pyrazinyl,
wherein one or more of the hydrogen atoms of said aryl group are necessarily and independently replaced with:
(A) $R^{62}$, which is aryl selected from the class consisting of phenyl, thiophenyl, pyridyl, pyrimidinyl, furyl, oxazolyl, thiazolyl, isoxazolyl, isothiazolyl, oxadiazolyl, thiadiazolyl, pyridazinyl, and pyrazinyl,
wherein one or more of the hydrogen atoms of said aryl group may be optionally and independently replaced with:
(i) methyl,
(ii) —COOH,
(iii) a group of the formula —$COOR^{63}$, wherein $R^{63}$ is methyl,
(iv) a group of the formula —$OR^{68}$, wherein $R^{68}$ is a hydrogen atom or methyl, or
(v) halogen,
(B) methyl, which may be mono- or polysubstituted with fluorine atoms or which may be monosubstituted with $R^{62}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —$COOR^{73}$, wherein $R^{73}$ is methyl,
(E) a group of the formula —$CONR^{76}R^{77}$, wherein $R^{76}$ and $R^{77}$ are each methyl, and wherein one of $R^{76}$ and $R^{77}$ is methyl and the other is the group $R^{62}$,
(F) a group of the formula —$COR^{78}$, wherein $R^{78}$ is a hydrogen atom, methyl or $R^{62}$,
(G) a group of the formula —$OR^{79}$, wherein $R^{79}$ is a hydrogen atom, methyl or $R^{62}$,
(H) cyano,
(I) nitro, or
(J) halogen;

$R^4$ is Cl or trifluoromethyl;
$R^5$ is a hydrogen atom; and,
$R^6$ is Cl, or trifluoromethyl;
or a pharmaceutically acceptable salt thereof.

Still more preferred are those novel compounds of formula I wherein:

Y is an oxygen atom;
Z is an oxygen atom;
X is a divalent group of the formula >$CHR^1$ or >$NR^1$, wherein $R^1$ is:
(A) a hydrogen atom,
(B) branched or unbranched alkyl of 1 to 6 carbon atoms or cycloalkyl of 3 to 6 carbon atoms, which alkyl or cycloakyl group may be monosubstituted with:

(i) oxo,
(ii) aryl selected from the class consisting of phenyl or pyridyl,
wherein one or more hydrogen atoms of said aryl group may be optionally and independently replaced with:
(a) alkyl of 1 to 3 carbon atoms,
—COOH,
(c) —$SO_2OH$,
(d) —$PO(OH)_2$,
(e) a group of the formula —$OR^{12a}$, wherein $R^{12a}$ is a hydrogen atom or a methyl,
(f) an amidino group of the formula

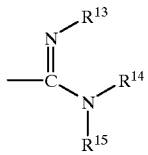

wherein $R^{13}$, $R^{14}$ and $R^{15}$ are each hydrogen atoms,
(iii) a group of the formula —$OR^{19}$, wherein $R^{19}$ is a hydrogen atom, or an alkyl or acyl group of 1 to 7 carbon atoms, or
(iv) a quaternary group of the formula

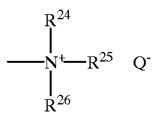

wherein $R^{24}$, $R^{25}$ and $R^{26}$ are each methyl and $Q^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group o f the formula

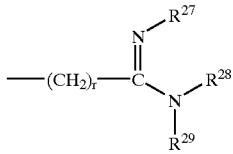

wherein r is 2, 3, 4, 5 or 6, and
$R^{27}$, $R^{28}$ and $R^{29}$ are each hydrogen atoms,
(G) an guanidino group of the formula

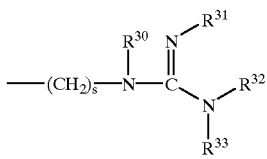

wherein s is 2, 3, 4, 5 or 6,
$R^{30}$, $R^{31}$, $R^{32}$ and $R^{33}$ are each hydrogen atoms, or
(H) piperidyl, wherein the nitrogen atom of said group is optionally substituted with:

(i) alkyl of 1 to 3 carbon atoms,
(ii) a carboxylic ester group of 2 to 7 carbon atoms,
(iii) a carboxylic acid group of 2 to 5 carbon atoms,
(iv) a phosphonic acid group of 1 to 6 carbon atoms, or
(v) a sulfonic acid group of 1 to 6 carbon atoms;

$R^2$ is:
(A) a hydrogen atom, or
(B) methyl;

$R^3$ is a group of the formula —$CH_2R^{41}$, wherein $R^{41}$ is
aryl selected from the class consisting of phenyl or pyridyl,
wherein one or more of the hydrogen atoms of said aryl group are necessarily and independently replaced with:
(A) $R^{62}$, which is aryl selected from the class consisting of phenyl, or pyridyl,
wherein one or more of the hydrogen atoms of said aryl group may be optionally and independently replaced with:
(i) methyl,
(ii) —COOH
(iii) a group of the formula —$COOR^{63}$, wherein $R^{63}$ is methyl,
(iv) a group of the formula —$OR^{68}$, wherein $R^{68}$ is a hydrogen atom or methyl, or
(v) halogen,
(B) methyl, which may be mono- or polysubstituted with fluorine atoms or which may be monosubstituted with $R^{62}$,
(C) branched or unbranched alkyl of 2 to 6 carbon atoms or cycloalkyl of 3 to 6 carbon atoms, which alkyl or cycloakyl group may be mono- or polysubstituted with fluorine or oxo,
(D) a group of the formula —$COOR^{73}$, wherein $R^{73}$ is methyl,
(E) a group of the formula —$CONR^{76}R^{77}$, wherein $R^{76}$ and $R^{77}$ are each methyl, and wherein one of $R^{76}$ and $R^{77}$ is methyl and the other is the group $R^{62}$,
(F) a group of the formula —$COR^{78}$, wherein $R^{78}$ is a hydrogen atom, methyl or $R^{62}$,
(G) a group of the formula —$OR^{79}$, wherein $R^{79}$ is a hydrogen atom, methyl or $R^{62}$,
(H) cyano,
(I) nitro, or
(J) halogen;

$R^4$ is a chlorine atom or trifluoromethyl;
$R^5$ is a hydrogen atom; and,
$R^6$ is a chlorine atom, or trifluoromethyl;
or a pharmaceutically acceptable salt thereof.

Especially preferred novel compounds of formula I are those wherein:
Y is an oxygen atom;
Z is an oxygen atom;
X is a divalent group of the formula >$CHR^1$ or >$NR^1$, wherein $R^1$ is:
(A) a hydrogen atom,
(B) alkyl of 1 to 2 carbon atoms which may be monosubstituted with:
(i) oxo,
(ii) aryl selected from the class consisting of phenyl or pyridyl, wherein one hydrogen atom of said aryl group may be optionally replaced with:

(a) alkyl of 1 to 3 carbon atoms,
(b) —COOH,
(c) —$SO_2OH$,
(d) —$PO(OH)_2$,
(e) a group of the formula —$OR^{12a}$, wherein $R^{12a}$ is a hydrogen atom or a methyl, or
(f) an amidino group of the formula

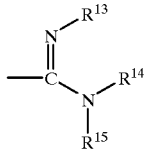

wherein $R^{13}$, $R^{14}$ and $R^{15}$ are each hydrogen atoms, or
(iii) a group of the formula —$OR^{19}$, wherein $R^{19}$ is a hydrogen atom or methyl,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula

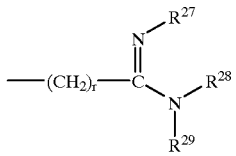

wherein r is 2, 3, 4, 5 or 6, and
$R^{27}$, $R^{28}$ and $R^{29}$ are each hydrogen atoms, or
(G) an guanidino group of the formula

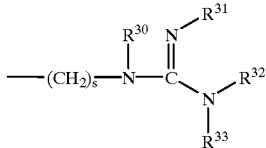

wherein s is 2, 3, 4, 5 or 6,
$R^{30}$, $R^{31}$, $R^{32}$ and $R^{33}$ are each hydrogen atoms, $R^2$ is:
(A) a hydrogen atom, or
(B) methyl;

$R^3$ is a group of the formula —$CH_2R^{41}$, wherein $R^{41}$ is
phenyl
wherein one or more of the hydrogen atoms of said phenyl group are necessarily and independently replaced with:
(A) $R^{62}$, which is aryl selected from the class consisting of phenyl, or pyridyl,
wherein one or more of the hydrogen atoms of said aryl group may be optionally and independently replaced with:
(i) methyl,
(ii) a group of the formula —$COOR^{63}$, wherein $R^{63}$ is methyl, (iv) a group of the formula —OR$^{68}$, wherein R$^{68}$ is a hydrogen atom or methyl, or
(v) halogen,
(B) methyl, which may be mono- or polysubstituted with fluorine atoms or which may be monosubstituted with R$^{62}$,
(C) a group of the formula —COOR$^{73}$, wherein R$^{73}$ is methyl,
(D) a group of the formula —COR$^{78}$, wherein R$^{78}$ is methyl or R$^{62}$,
(E) a group of the formula —OR$^{79}$, wherein R$^{79}$ is a hydrogen atom, methyl or R$^{62}$,
(F) cyano,
(G) nitro, or
(H) halogen;
R$^4$ is a chlorine atom or trifluoromethyl;
R$^5$ is a hydrogen atom; and,
R$^6$ is a chlorine atom, or trifluoromethyl;
or a pharmaceutically acceptable salt thereof.

Even more especially preferred novel compounds of formula I are those wherein:
Y is an oxygen atom;
Z is a n oxygen atom;
X is a divalent group of the formula >NR$^1$, wherein R$^1$ is:
(A) a hydrogen atom,
(B) methyl or ethyl, or
(C) —COCH$_3$
R$^2$ is:
(A) a hydrogen atom, or
(B) methyl;
R$^3$ is a group of the formula —CH$_2$R$^{41}$, wherein R$^{41}$ is:
phenyl,
wherein one or more of the hydrogen atoms of said phenyl group are necessarily and independently replaced with:
(A) R$^{62}$, which is aryl selected from the class consisting of phenyl, or pyridyl,
wherein one or more of the hydrogen atoms of said aryl group may be optionally and independently replaced with:
(i) methyl,
(ii) a group of the formula —COOR$^{63}$, wherein R$^{63}$ is methyl,
(iii) a group of the formula —OR$^{68}$, wherein R$^{68}$ is a hydrogen atom or methyl, or
(iv) halogen,
(B) methyl, which may be mono- or polysubstituted with fluorine atoms or which may be monosubstituted with R$^{62}$,
(C) a group of the formula —COOR$^{73}$, wherein R$^{73}$ is methyl,
(D) a group of the formula —COR$^{78}$, wherein R$^{78}$ is methyl or R$^{62}$,
(E) a group of the formula —OR$^{79}$, wherein R$^{79}$ is a hydrogen atom, methyl or R$^{62}$,
(F) cyano,
(G) nitro, or
(H) halogen;
R$^4$ is a chlorine atom or trifluoromethyl;
R$^5$ is a hydrogen atom; and,
R$^6$ is a chlorine atom, or trifluoromethyl;
or a pharmaceutically acceptable salt thereof.

Penultimately preferred novel compounds of formula I are those wherein:

Y is an oxygen atom;
Z is an oxygen atom;
X is a divalent group of the formula >NR$^1$, wherein R$^1$ is:
(A) a hydrogen atom,
(B) methyl or ethyl, or
(C) —COCH$_3$
R$^2$ is:
(A) a hydrogen atom, or
(B) methyl;
R$^3$ is a group of the formula —CH$_2$R$^{41}$, wherein R$^{41}$ is
phenyl
wherein one or more of the hydrogen atoms of said phenyl group are necessarily and independently replaced with:
(A) R$^{62}$, which is aryl selected from the class consisting of phenyl, or pyridyl,
wherein one or more of the hydrogen atoms of said aryl group may be optionally and independently replaced with:
(i) methyl, or
(ii) halogen,
(B) methyl, which may be mono- or polysubstituted with fluorine atoms,
(C) a group of the formula —COR$^{78}$, wherein R$^{78}$ is methyl or R$^{62}$,
(D) halogen;
R$^4$ is a chlorine atom;
R$^5$ is a hydrogen atom; and,
R$^6$ is a chlorine atom;

or a pharmaceutically acceptable salt thereof.

Ultimately preferred novel compounds of formula I are those specific compounds having the following structures:

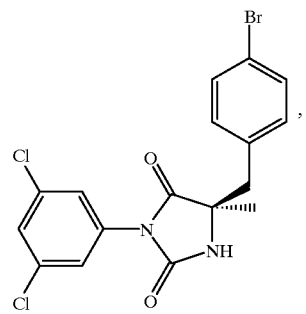

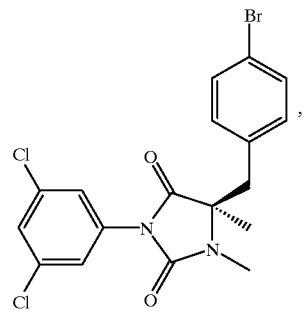

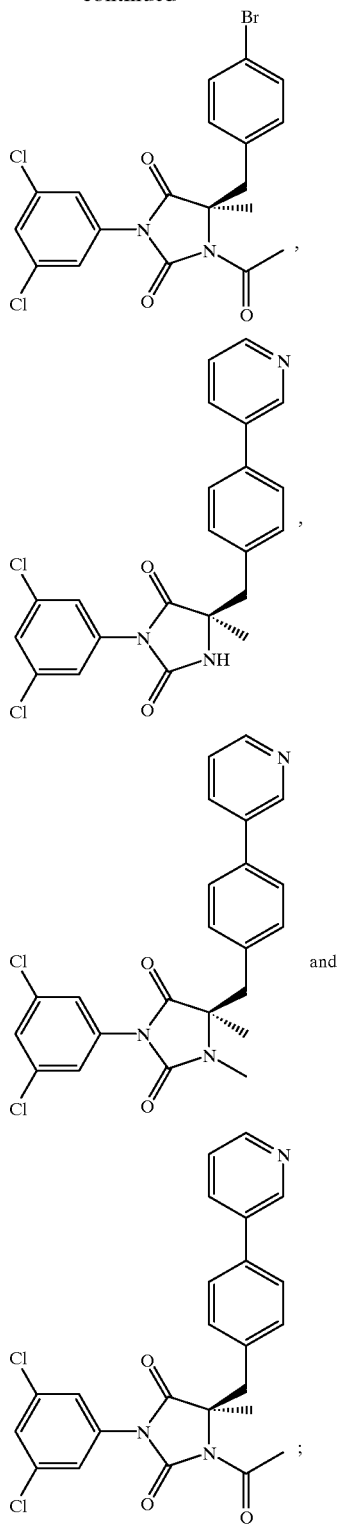

or a pharmaceutically acceptable salt thereof.

Synthesis of the Compounds of the Invention

The synthesis of similar compounds to those of the invention are well known in the prior art. Depending on one's purpose, some routes may be better for providing small amounts of a variety of compounds while other routes may be more amenable to the large scale synthesis of a specific compound. Below are illustrated several routes to these compounds and examples of compounds that have been synthesized by the respective routes.

The starting amino acids and their derivatives necessary for the synthesis of the hydantoin and thio-hydantoin structures are either commercially available or are produced by obvious modifications of known literature procedures (see e.g.: Williams, R. W. *Synthesis of Optically Active α-Amino Acids*; Pergamon: Oxford, 1989, α-*Amino Acid Synthesis*; O'Donnell, M. J., Ed.; Tetrahedron Symposium in Print; Pergamon: London, 1988: Vol. 44, Issue 17, Jung, M. J. *Chemistry and Biochemistry of the Amino Acids*; Barrett, G. C., Ed.; Chapman and Hall: New York, 1985; p.227, and Spero, D. M.; Kapadia, S. R. *J. Org. Chem.* 1996, 61: 7398–7401). The synthesis and resolution of ethyl 2-amino-2-(4-bromobenzyl)-propanoate (the starting material for example 39) is given by way of example.

A solution of alanine ethyl ester hydrochloride (15.3 g, 99.3 mmol) in 60 mL of water was treated with triethylamine (14.6 mL, 104.8 mmol) at room temperature for 30 min. The mixture was then extracted twice with 100 mL of methylene chloride. The organic layers were combined, dried over sodium sulfate, and concentrated in vacuo to afford 10.0 g of the free base of the amino ester (86% yield). The residue was re-dissolved in methylene chloride and cooled in an ice bath. Magnesium sulfate (11.3 g, 93.9 mmol) was added, followed by trimethyl acetaldehyde (9.3 mL, 85.6 mmol). The ice bath was removed, and the mixture was stirred overnight. The magnesium sulfate was removed by filtration, and the filtrate was concentrated in vacuo to afford 11.8 g of the imine intermediate (74.6% yield).

The imine from above (11.8 g, 63.7 mmol) was dissolved in toluene (90 mL). 4-bromobenzyl bromide (17.5 g, 70.1 mmol) was added, and the reaction was cooled to about -10° C. Potassium tert-butoxide (8.6 g, 76.5 mmol) was added at such a rate that the temperature did not exceed 0° C. The reaction stirred in the cold bath for two hours, then was diluted with ether and washed with water (150 mL). The organic layer was dried (sodium sulfate), filtered, and concentrated in vacuo to afford a clear yellow oil. This was treated with 1 N HCl (100 ml, 100 mmol) and stirred overnight. The reaction was extracted with ethyl acetate (100 mL), and the aqueous layer was to afford 14.1 g of the racemic amino ester hydrochloride (68.7% yield).

The racemic compounds can be resolved into their component enantiomers via a number of known techniques. Ethyl 2-(R)-amino-2-(4-bromobenzyl)-propanoate (the starting material for example 29) was produced from racemic ethyl 2-amino-2-(4-bromobenzyl)-propanoate by the following procedure: To 1.3 L of a buffer made from 13.69 g KH$_2$PO$_4$ and 2 L of water was added 20 g of the commercially available enzyme Lipase L10 (Amino Enzyme USA Co., Ltd, Lombardi, Ill.) followed by 12 g of the HCl salt of the racemic amino ester. The pH was monitored and 1 N KOH was added as needed to keep the pH of the mixture at 6.4. The course of the reaction was monitored with reverse phase HPLC and after 2 days, the HPLC analysis indicated that 50.4% of the starting material had been hydrolyzed. At this point enough solid NaHCO$_3$ was added to adjust the pH to 8.1 and the mixture was extracted twice with toluene, ether and EtOAc. The combined organic layers was dried and concentrated and the crude product purified by silica gel chromatography (EtOAC: Hexanes) to yield 5.21 g (87%) of ethyl 2-(R)-amino-2-(4-bromobenzyl)-propanoate.

Method A. Starting with an Amino Acid and a Phenylisocyanate. Cyclization with Acid.

An appropriate amino acid is dissolved in aqueous base (such as, for example, NaOH, KOH, $Na_2CO_3$, $NaHCO_3$, $K_2CO_3$ or $KHCO_3$) and warmed to between about 20 and 90° C. An appropriate isocyanate is added to this mixture and the resulting solution was stirred until the reaction essentially reaches completion. Upon cooling, the mixture is acidified and the resulting ureidoacetic acid is isolated by filtration or by extraction into organic solvent. Removal of solvent produces the intermediate ureidoacetic acid. In the manner reported by Sauli (U.S. Pat. No. 4,099,008), the intermediate ureidoacetic acid is cyclized by heating in the presence of a catalytic amount of acid (such as, for example, sulfuric acid, methanesulfonic acid, benzenesulfonic acid or hydrochloric acid) in an organic or aqueous solvent, to produce the desired hydantoin. Workup consists of collection of the hydantoin by filtration and purification by, for example, silica gel chromatography or recrystallization.

Compounds listed in Table 1 were produced via this general method.

TABLE 1

Examples of Compounds Synthesized by Method A.

| EX. | STRUCTURE | STARTING AMINO ACID | STARTING ISOCYANATE | M.P. (° C.) |
|---|---|---|---|---|
| 1 | 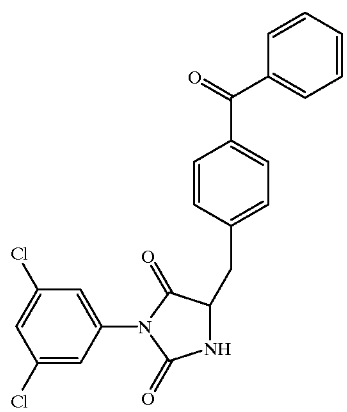 | | | 165–6 |
| 2 | 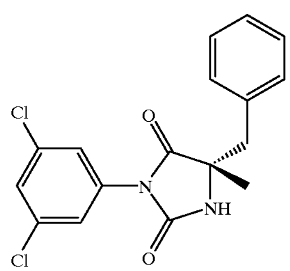 | | | 145–6 |
| 3 | 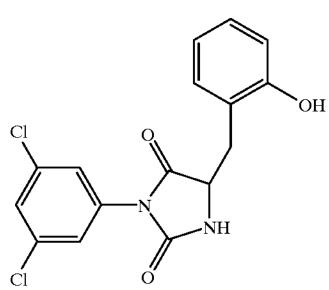 | | | 165–7 |

TABLE 1-continued

Examples of Compounds Synthesized by Method A.

| EX. | STRUCTURE | STARTING AMINO ACID | STARTING ISOCYANATE | M.P. (° C.) |
|---|---|---|---|---|
| 4 | 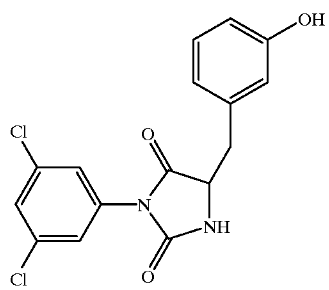 | | | 201–2 |
| 5 | 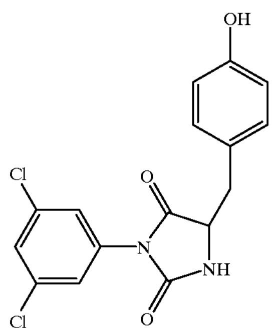 | | | 206–8 |
| 6 | 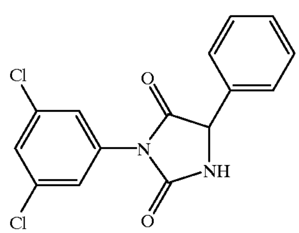 | | | 197–8 |
| 7 | 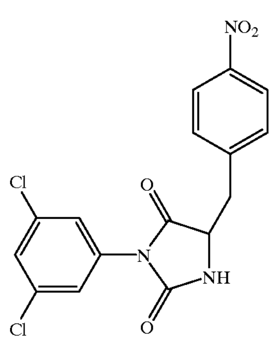 | | | 195–6 |

TABLE 1-continued

Examples of Compounds Synthesized by Method A.

| EX. | STRUCTURE | STARTING AMINO ACID | STARTING ISOCYANATE | M.P. (° C.) |
| --- | --- | --- | --- | --- |
| 8 | 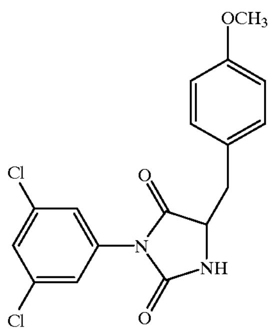 | | | 146–8 |
| 9 | 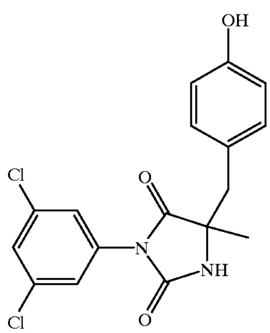 | | | 225–6 |
| 10 | 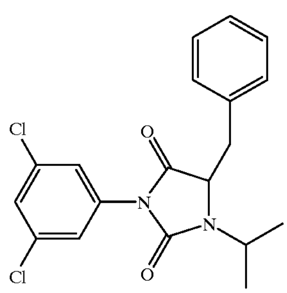 | | | 122–3 |
| 11 | 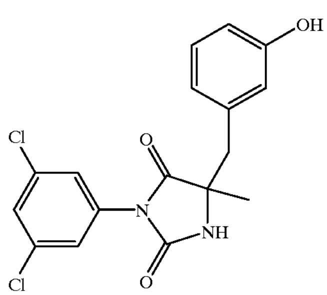 | | | 197–8 |

TABLE 1-continued

Examples of Compounds Synthesized by Method A.

| EX. | STRUCTURE | STARTING AMINO ACID | STARTING ISOCYANATE | M.P. (° C.) |
|---|---|---|---|---|
| 12 | 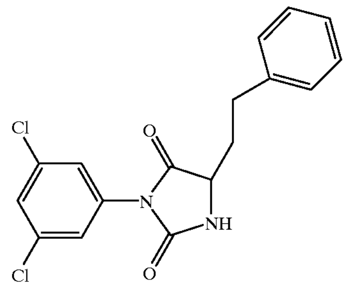 | | | 145–6 |
| 13 | 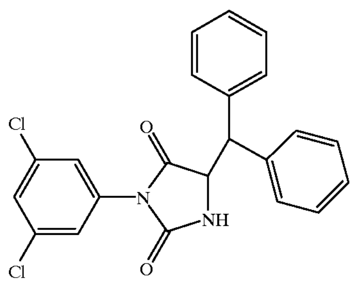 | | | 64–6 |

Method A is exemplified by the synthesis of the compound of Example 12 (see Table 1), which was carried out as follows. Homophenylalanine (1.00 g, 5.58 mmol) was dissolved in a solution of NaOH (0.28 g, 6.69 mmol) in $H_2O$ (10.0 mL) and heated at 45° C. When the solution became homogeneous, 3,5-dichlorophenyl isocyanate (1.05 g, 5.58 mmol) was added, and the mixture was heated at 45° C. for 2 h more. The cooled reaction mixture was then acidified with concentrated HCl to pH=2–3. The precipitate was collected by filtration, washed with water, and dried in vacuo at 50° C. to afford 0.85 g of the intermediate ureidoacetic acid (42%, crude yield). The intermediate was then taken up in a solution of concentrated HCl (5.0 mL) and water (5.0 mL) and heated under reflux for 5 h. The reaction mixture was then cooled to room temperature and the white solid was collected by suction filtration, washed with water, and dried in vacuo at 50° C. to afford 0.52 g of the crude hydantoin. This material was purified by recrystallization from EtOH to afford 0.37 g (45%) of the compound from Example 12.

Method B. Starting with an amino acid and a phenylisocyanate. Cyclization with EDC.

An appropriate amino acid is dissolved in aqueous base (such as, for example, NaOH, KOH, $Na_2CO_3$, $NaHCO_3$, $K_2CO_3$ or $KHCO_3$) and warmed to between about 20 and 90° C. An appropriate isocyanate is added to this mixture and the resulting solution is stirred until the reaction essentially reaches completion. Upon cooling, the mixture is acidified and the resulting ureidoacetic acid is isolated by filtration or extraction into organic solvent. Removal of solvent produces the intermediate ureidoacetic acid. The intermediate ureidoacetic acid is then cyclized to the desired hydantoin in organic solvent (such as, for example, DMF, NMP, or THF) using any of a number of dehydrating agents (such as, for example, dicyclohexylcarbodiimide (DCC) or 1-(3-dimethylaminopropyl)-3-ethylcarbodiimide HCl (EDC)) in the presence of an ester activating agent (such as 1-hydroxybenzotriazole hydrate (HOBT)) and a non-nucleophilic base (such as, for example, triethylamine or N,N-diisopropylethylamine). Work-up consists of extraction into an organic solvent followed by purification via, for example, silica gel chromatography or recrystallization.

Compounds listed in Table 2 were produced via this general method.

TABLE 2

Examples of Compounds Synthesized by Method B.

| EX. | STRUCTURE | STARTING AMINO ACID | STARTING ISOYANATE | M.P. (° C.) |
|---|---|---|---|---|
| 14 | 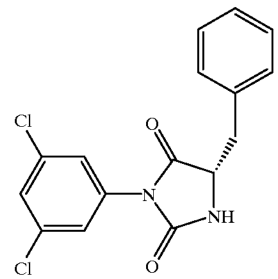 | | | 113–4 |
| 15 | 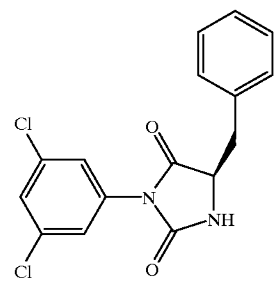 | | | 114–5 |
| 16 | 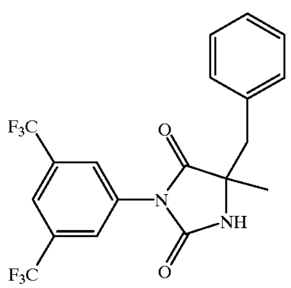 | | | 96–7 |
| 17 | 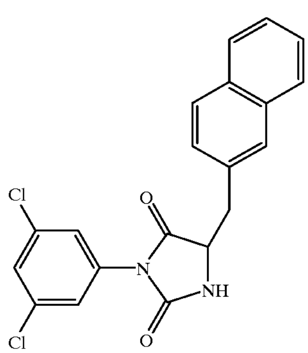 | | | 195–7 |
| 18 | 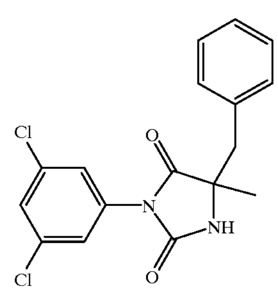 | | | 145–6 |

TABLE 2-continued

Examples of Compounds Synthesized by Method B.

| EX. | STRUCTURE | STARTING AMINO ACID | STARTING ISOYANATE | M.P. (° C.) |
|---|---|---|---|---|
| 19 | (3,5-dichlorophenyl hydantoin with 4-bromobenzyl) | 4-bromo-phenylalanine | 3,5-dichlorophenyl isocyanate | 190–1 |
| 20 | (3,5-bis(trifluoromethyl)phenyl hydantoin with benzyl) | phenylalanine | 3,5-bis(trifluoromethyl)phenyl isocyanate | 128–30 |
| 21 | (3,5-dichlorophenyl hydantoin with α-methylbenzyl, Racemic) | β-methyl-phenylalanine (Racemic) | 3,5-dichlorophenyl isocyanate | 158–9 |
| 22 | (3,5-dichlorophenyl hydantoin with α-methylbenzyl, Racemic) | β-methyl-phenylalanine (Racemic) | 3,5-dichlorophenyl isocyanate | 116–26 |

TABLE 2-continued

Examples of Compounds Synthesized by Method B.

| EX. | STRUCTURE | STARTING AMINO ACID | STARTING ISOYANATE | M.P. (° C.) |
|---|---|---|---|---|
| 23 | 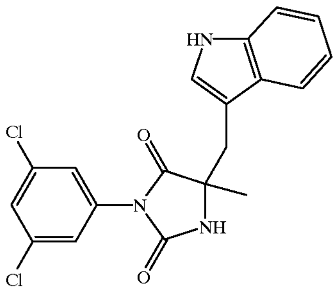 | | | 278–9 |
| 24 | 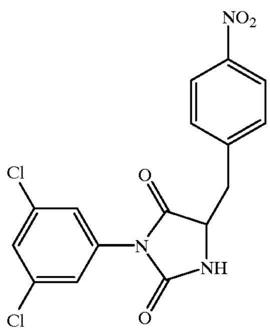 | | | 181–3 |
| 25 | 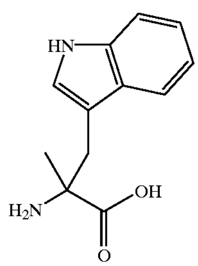 | | | 153–4 |
| 26 | 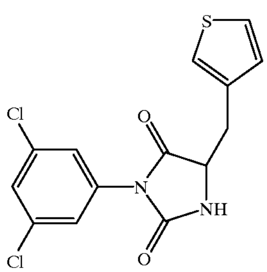 | | | 167–8 |
| 27 | 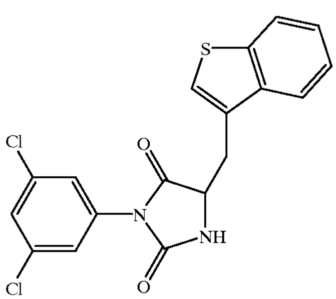 | | | 173–5 |

Method B is exemplified by the synthesis of the compound of Example 15 (see Table 2), which was carried out as follows: To a solution of (R)-phenylalanine (0.33 g, 2 mmol) in 1 mL of 2 N NaOH and 10 mL of water at 50° C. was added 3,5-dichlorophenyl isocyanate (0.38 g, 2 mmol). The resulting mixture was then stirred for 1 h. The solution was cooled and treated with concentrated HCl until a precipitate formed and the solution remained acidic. The precipitate was collected by filtration and dried in vacuo to produce the desired ureidoacetic acid (0.60 g, 85%). The ureidoacetic acid (0.35 g, 1 mmol) was dissolved in 20 mL of DMF and treated with EDC (0.19 g, 1 mmol) and HOBT (0.14 g, 1 mmol) for 1 h at room temperature. After this period N,N-diisopropylethylamine (0.35 mL, 2 mmol) was added and the mixture stirred overnight. Workup consisted of trituration with water, collection of the hydantoin by filtration, and purification by silica gel chromatography. The yield in this example was 0.20 g (60%).

Method C. Starting with an Amino Ester or a Hydroxy Ester and a Phenylisocyanate. Cyclization with Base or Acid.

An appropriate amino ester or hydroxy ester and an appropriate isocyanate are dissolved in an organic solvent (such as, for example, DMF, TBF or DMSO) in the presence of a base (such as, for example, NaOH, KOH, $Na_2CO_3$, $NaHCO_3$, $K_2CO_3$ or $KHCO_3$) and warmed to between about room temperature and 60° C. After approximately 1 h, the temperature of the reaction mixture is raised to between about 50 and 100° C. until the reaction appears complete. The solution is then cooled and diluted with an organic solvent (such as, for example, EtOAc or $CH_2Cl_2$). The organic phase is washed sequentially with dilute aqueous acid (e.g. 1 N HCl) and water, dried (e.g. over $MgSO_4$) and concentrated. The desired hydantoin is purified, for example by silica gel chromatography or by recrystallization. (Alternatively the ureidoacetic ester can be cyclized to the hydantoin by heating to between about 50 and 100° C. in the presence of an acid such as, for example, aqueous HCl until the reaction appears complete).

Compounds listed in Table 3 were produced via this general method.

TABLE 3

Examples of Compounds Synthesized by Method C.

| EX. | STRUCTURE | STARTING AMINO ESTER | STARTING ISOCYANATE | M.P. (° C.) |
| --- | --- | --- | --- | --- |
| 28 | 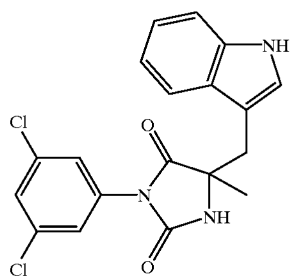 | | | 200–2 |
| 29 | 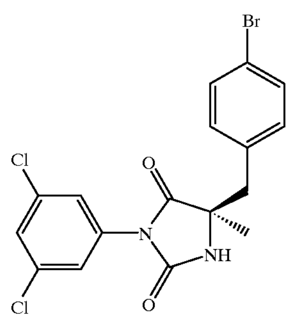 | | | 63–5 |
| 30 | 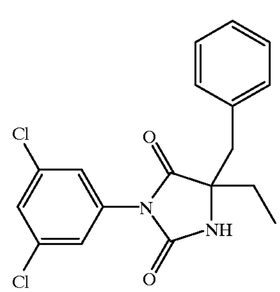 | | | 162–4 |

TABLE 3-continued

Examples of Compounds Synthesized by Method C.

| EX. | STRUCTURE | STARTING AMINO ESTER | STARTING ISOCYANATE | M.P. (° C.) |
|---|---|---|---|---|
| 31 | 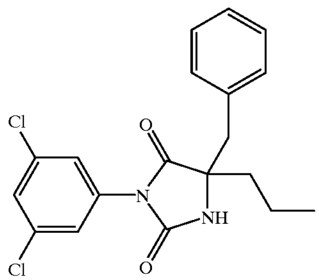 | | | 157–8 |
| 32 | 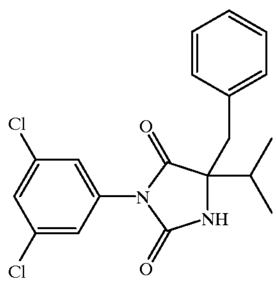 | | | 203–5 |
| 33 | 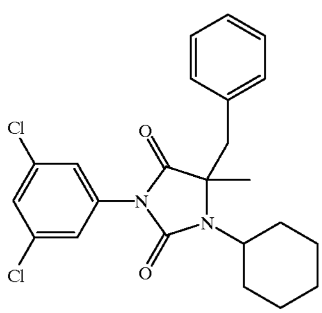 | | | oil |
| 34 | 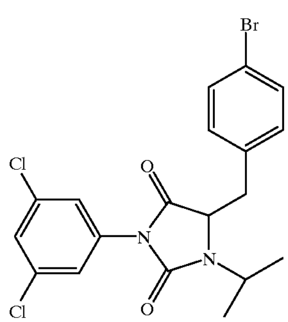 | | | 108–9 |

TABLE 3-continued

Examples of Compounds Synthesized by Method C.

| EX. | STRUCTURE | STARTING AMINO ESTER | STARTING ISOCYANATE | M.P. (° C.) |
|---|---|---|---|---|
| 35 | 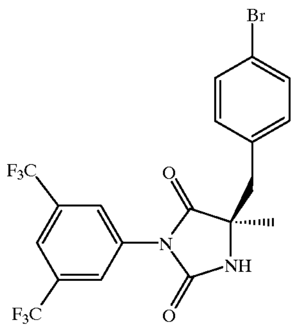 | | | 105–6 |
| 36 | 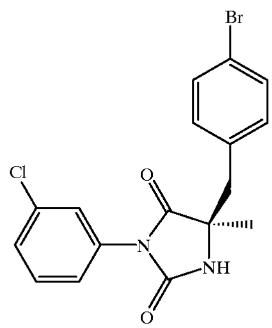 | | | 58–60 |
| 37 | 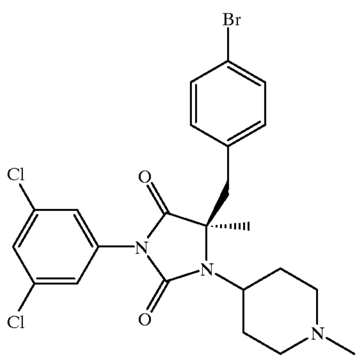 | | | 92–3 |
| 38 | 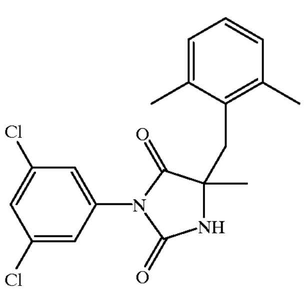 | | | 194–5 |

TABLE 3-continued

Examples of Compounds Synthesized by Method C.

| EX. | STRUCTURE | STARTING AMINO ESTER | STARTING ISOCYANATE | M.P. (° C.) |
|---|---|---|---|---|
| 39 | 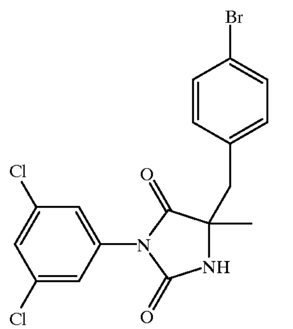 | | | 135–6 |
| 40 | 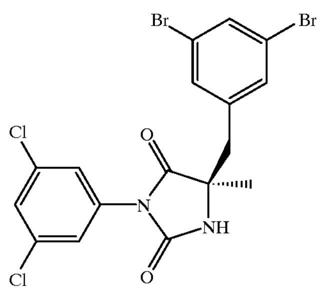 | | | 157–8 |
| 41 | 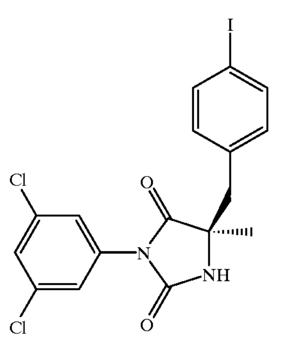 | | | 72–4 |
| 42 | 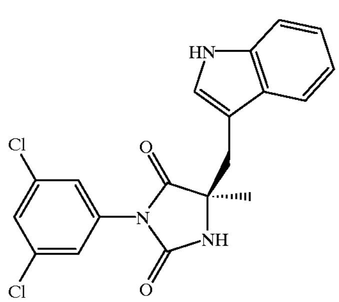 | | | 143–4 |

TABLE 3-continued

Examples of Compounds Synthesized by Method C.

| EX. | STRUCTURE | STARTING AMINO ESTER | STARTING ISOCYANATE | M.P. (° C.) |
|---|---|---|---|---|
| 43 | [structure: 1-(3,4,5-trichlorophenyl)-5-(4-bromobenzyl)-5-methylhydantoin] | [structure: methyl 2-amino-2-(4-bromobenzyl)propanoate ethyl ester, H$_2$N, OEt] | [structure: 3,4,5-trichlorophenyl isocyanate] | 73–4 |
| 44 | [structure: 1-(3,5-dichlorophenyl)-5-(4-nitrobenzyl)-5-methylhydantoin] | [structure: 2-amino-2-(4-nitrobenzyl)propanoic acid ethyl ester] | [structure: 3,5-dichlorophenyl isocyanate] | oil |
| 45 | [structure: 3-(3,5-dichlorophenyl)-5-methyloxazolidine-2,4-dione] | [structure: ethyl lactate, HO—CH(CH$_3$)—C(O)—OEt] | [structure: 3,5-dichlorophenyl isocyanate] | not determ. |

Method C is exemplified by the synthesis of the compound of Example 30 of Table 3, which is as follows: Methyl 2-amino-2-benzylbutyric acid (0.21 g, 1 mmol) and 3,5-dichlorophenyl isocyanate (0.19 g, 1 mmol) were dissolved in DMSO (5 mL) in the presence of approximately 0.2 g of Na$_2$CO$_3$ and allowed to stir at 50° C. for 1 h. After this period the solution was heated to 90° C. for 2 hr. The solution was then cooled, diluted with EtOAc and washed with 0.1 N HCl and water. The organic layer was dried over MgSO$_4$ and concentrated to produce a crude product which was further purified by silica gel chromatography to yield 0.12 g (33%) of the compound of example 30.

Method D. Solid Phase Synthesis.

There are several examples in the literature which demonstrate that the synthesis of hydantoins and their precursor amino acid derivatives can be performed in the solid phase which may make the synthesis of large varieties of these compounds amenable to an automated approach. Examples for the synthesis of the precursor amino acid derivatives are shown in the following citations: *J. American Chemical Society*, 1996, 118, 6070–1, *Tetrahedron Letters*, 1997, 38, 7163–7166, *Tetrahedron Letters*, 1997, 38, 8821. An literature citation which demonstrates the conversion of these amino acid derivatives to hydantoins is *J. Organic Chemistry* 1997, 62, 6060–2.

An amino acid attached to a solid phase resin through its carboxylic acid via an appropriate linker (for example the Wang resin: 4-benzyloxy-benzyl polystyrene) is protected on its nitrogen with a reagent that will allow for the alkylation of the alpha-carbon (for example, a benzaldehyde derivative that forms an imine with the nitrogen of the amino acid). The protected compound is then treated with a base and an alkylating agent to generate the new protected amino acid derivative. The protecting group is removed using standard conditions (in the case of an imine this is accomplished, for example, with aqueous HCl) and the free amino group is reacted with an isocyanate to generate the intermediate urea. This intermediate is treated with a reagent to catalyze the cyclization of the urea portion onto the carboxylate end of the molecule which forms the desired hydantoin and cleaves the product from the resin. Purification is via silica gel chromatography, reverse phase HPLC of recrystallization.

Compounds listed in Table 4 were produced via this general method.

TABLE 4

Examples of Compounds Synthesized by Method D.

| EX. | STRUCTURE | ALKYLATING AGENT | STARTING ISOCYANATE | M.P. (° C.) |
|---|---|---|---|---|
| 46 | 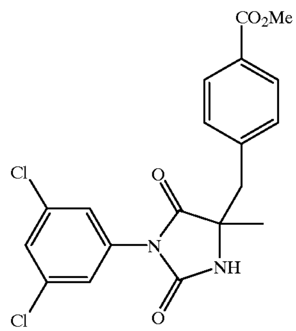 | | | Not determ. |
| 47 | 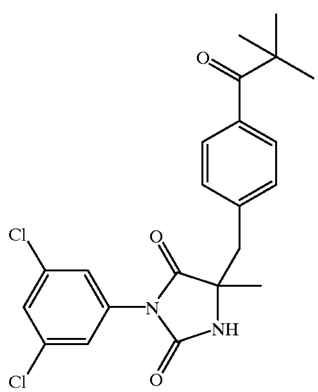 | | | Not determ. |
| 48 | 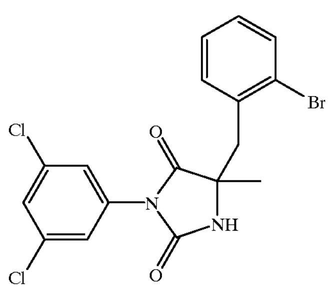 | | | Not determ. |
| 49 | 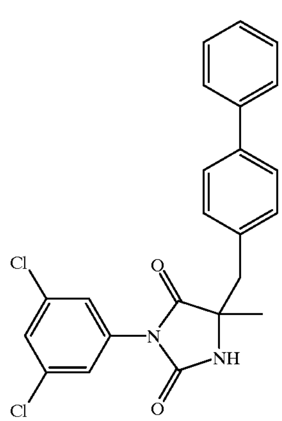 | | | 61–3 |

TABLE 4-continued

Examples of Compounds Synthesized by Method D.

| EX. | STRUCTURE | ALKYLATING AGENT | STARTING ISOCYANATE | M.P. (° C.) |
|---|---|---|---|---|
| 50 | 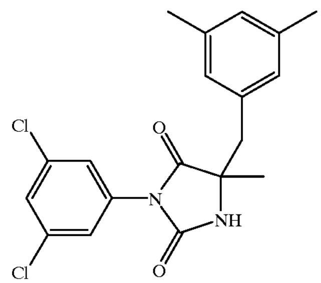 | | | >240 |
| 51 | 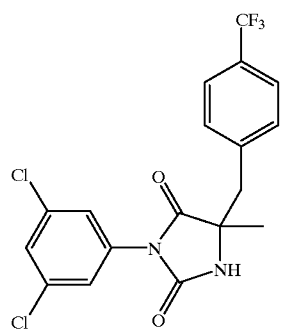 | | | Not determ |
| 52 | 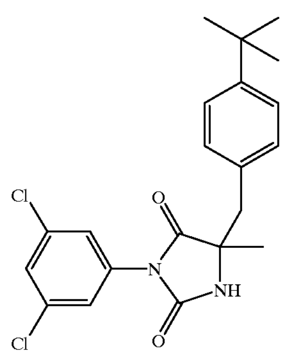 | | | Not determ |
| 53 | 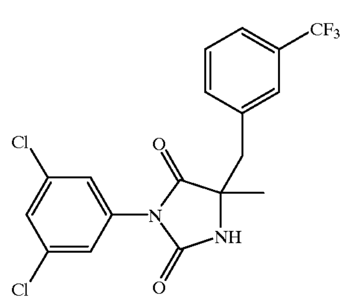 | | | Not determ |

TABLE 4-continued

Examples of Compounds Synthesized by Method D.

| EX. | STRUCTURE | ALKYLATING AGENT | STARTING ISOCYANATE | M.P. (° C.) |
|---|---|---|---|---|
| 54 | 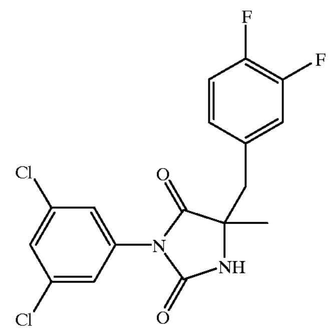 | | | 117–8 |
| 55 | 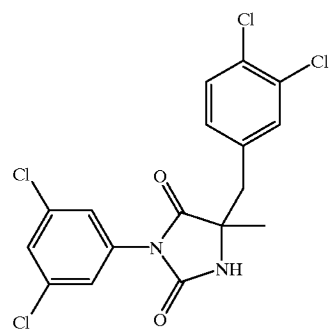 | | | 150–1 |
| 56 | 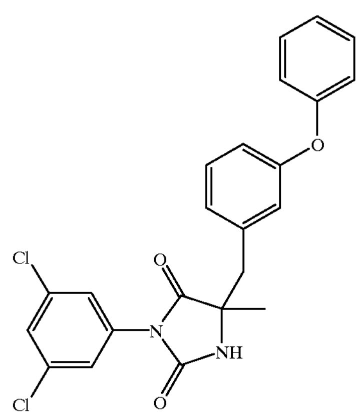 | | | Not determ |
| 57 | 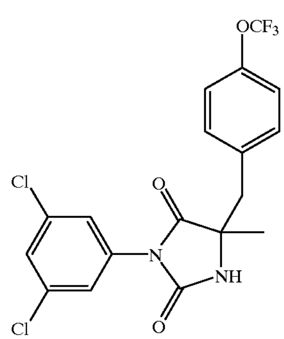 | | | Not determ |

TABLE 4-continued

Examples of Compounds Synthesized by Method D.

| EX. | STRUCTURE | ALKYLATING AGENT | STARTING ISOCYANATE | M.P. (° C.) |
|---|---|---|---|---|
| 58 | 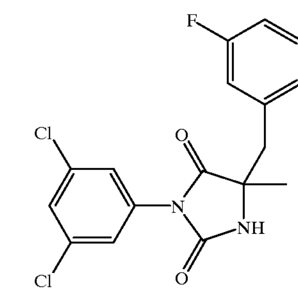 | | | Not determ |
| 59 | 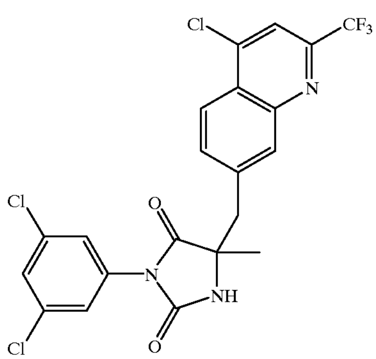 | | | 173–4 |
| 60 | 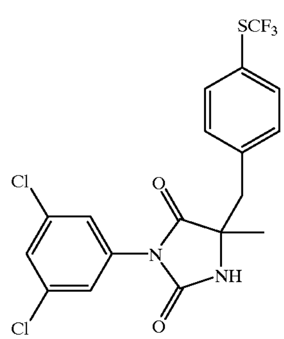 | | | 133–4 |
| 61 | 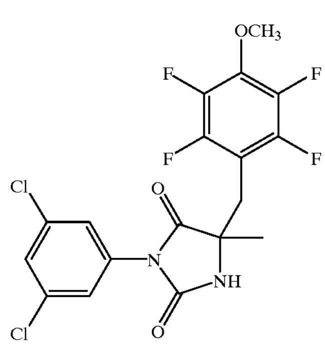 | | | 122–3 |

TABLE 4-continued

Examples of Compounds Synthesized by Method D.

| EX. | STRUCTURE | ALKYLATING AGENT | STARTING ISOCYANATE | M.P. (° C.) |
|---|---|---|---|---|
| 62 | 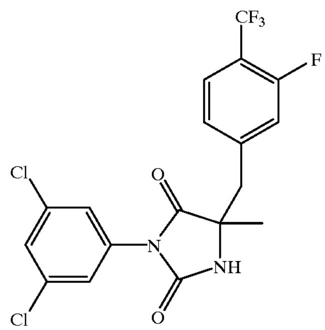 | | | 67–9 |
| 63 | 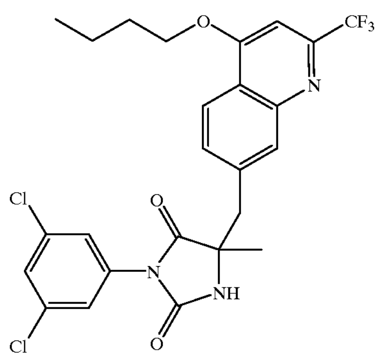 | | | Not determ. |
| 64 | 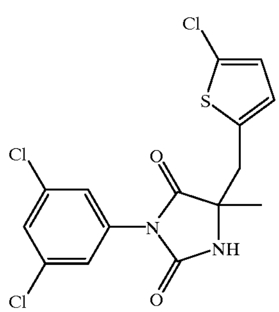 | | | 55–6 |
| 65 | 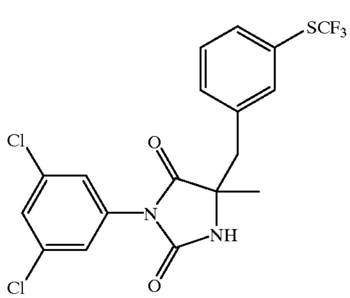 | | | 170–1 |

TABLE 4-continued

Examples of Compounds Synthesized by Method D.

| EX. | STRUCTURE | ALKYLATING AGENT | STARTING ISOCYANATE | M.P. (° C.) |
|---|---|---|---|---|
| 66 | 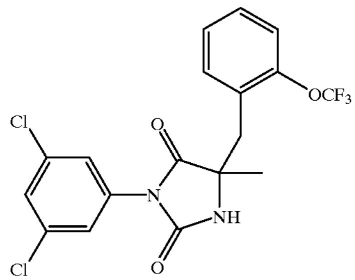 | | | 153–5 |
| 67 | 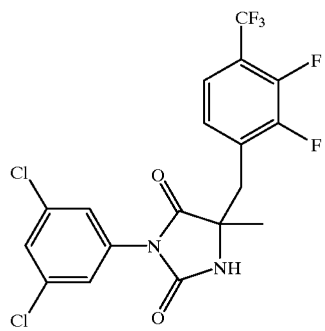 | | | 163–4 |
| 68 | 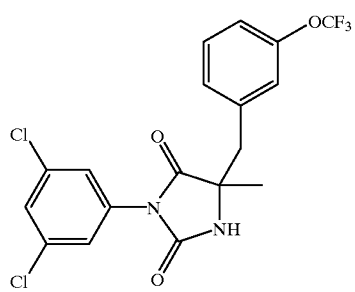 | | | Not determ |
| 69 | 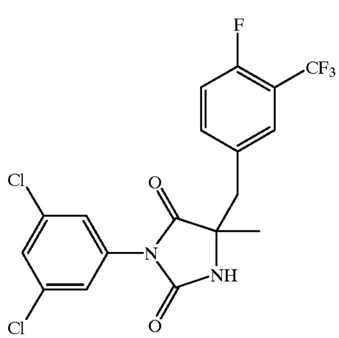 | | | 168–70 |

Method D is exemplified by the synthesis of the compound of Example 67, which was carried out as follows: A reaction vessel was charged with the commercially available Fmoc-Ala-Wang (300 mg, 0.150 mmol) and 3 mL of a 20% solution of piperidine in N-methyl pyrollidinone (NMP). The reaction vessel was agitated at room temperature on an orbital shaker for 45 minutes. The resin was filtered and washed with NMP (3×1 mL). The reaction vessel containing resin was equipped with a rubber septum, placed under argon, charged with 3,4-dichlorobenzaldehyde (394 mg, 2.25 mmol), trimethyl orthoformate (3.5 mL), and NMP (1.5 mL). The resulting mixture was agitated at room temperature for 15 h. The solid resin was isolated by filtration and washed sequentially with NMP (3×3 mL), tetrahydrofuran (3×mL), and CH$_2$Cl$_2$ (3×mL). The resin was then dried under vacuum for approximately one hour to produce the imine-resin intermediate.

The imine-resin intermediate was alkylated with 2,3-difluoro-4-trifluormethylbenzyl bromide (123.8 mg, 0.45 mmol) by mixing these two reagents, 2-tert-butylimino-2-diethylamino-1,3-dimethylperhydro-1,3,2-diazaphosphorine (BEMP, 0.217 mL, 0.75 mmol), and NMP (3.5 mL) and agitating the mixture at room temperature on an orbital shaker for 15 h. The solid was isolated by filtration and washed sequentially with NMP (3×mL), THF (3×mL), and CH$_2$Cl$_2$ (3×3 mL) yielding the alkylated-imine-resin intermediate upon drying.

The imine was cleaved from the preceding intermediate by treatment with aqueous 1 N HCl (1.8 mL) and THF (3.6 mL) and agitating at room temperature for about 15 h. The resin bound amino ester was isolated by filtration and washed sequentially with NMP (3×3 mL), THF (3×3 mL), and CH$_2$Cl$_2$ (3×3 mL) and dried under vacuum.

The resin bound amino ester was converted to the hydantoin using a procedure that cleaves the final product from the resin. The intermediate amino-ester was placed in a reaction vessel and treated with 3 mL of a 20% solution of N,N-diisopropylethylamine in NMP. After agitation at room temperature under argon for 1 h, the resin was filtered, washed with NMP (3×3 mL) and methanol (3×3 mL), and placed under vacuum. Subsequently, the vessel was opened under argon and charged with 2.5 mL of a 1.75 M solution of 3,5-dichlorphenylisocyanate in dimethylformamide (DMF, 0.45 mmol). The mixture was agitated at room temperature under argon overnight and the product removed from the resin by filtration. After the resin was washed ethyl acetate (6×2 mL), the combined organic solutions were diluted with water and then washed with water (3×3 mL) and saturated aqueous NaCl (2×3 mL), dried over sodium sulfate, filtered, and concentrated under a stream of nitrogen. Final purification was accomplished using reverse phase HPLC (acetonitrile-water gradient).

Method E. Starting with an Isocyanateester and an Aniline. Cyclization with base or Acid.

To an appropriate isocyanate ester, dissolved in an organic solvent (such as for, example, methylene chloride) is added an appropriate aniline, and the mixture is stirred for between about 1 and 24 h, at about room temperature, under an inert atmosphere, such as argon. The organic solvent is is then removed in vacua. Excess aniline is removed (as by boiling the crude solid in hexanes and decanting off the liquid, or by flash chromatography over silica gel) leaving the solid ureidoacetic ester. The ureidoacetic ester is cyclized to the desired hydantoin by treatment with base (such as, for example, NaH, NaHMDS, Na$_2$CO$_3$, NaHCO$_3$, K$_2$CO$_3$ or KHCO$_3$) in an organic solvent (such as, for example, THF or DMF), followed by warming to approximately 60–90° C. The solution is next cooled and diluted with an organic solvent (such as, for example, EtOAc). The organic solution is washed sequentially with dilute aqueous acid (such as 1 N HCl) and then water, dried (as with MgSO$_4$) and concentrated. The desired hydantoin is purified, as by silica gel chromatography or recrystallization. (Alternatively the intermediate ureidoacetic ester can be cyclized to the hydantoin by heating to about 90° C. in the presence of an acid, such as aqueous HCl, as mentioned in method C).

The compounds listed in Table 5 were produced via this method.

TABLE 5

Example of Compound Synthesized by Method E.

| EX. | STRUCTURE | STARTING ISOCYANATE ESTER | STARTING ANILINE | M.P. (° C.) |
|---|---|---|---|---|
| 70 | 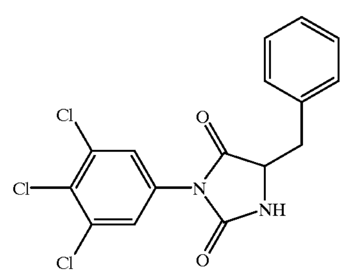 | | | 178–9 |
| 71 | 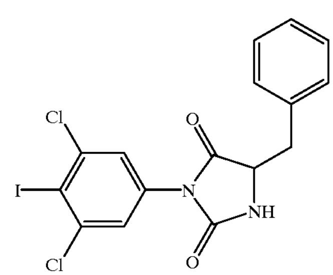 | | | 145–6 |

Method E is exemplified by the synthesis of the compound from example 70, shown in Table 5, which was carried out as follows: To a solution of ethyl 2-isocyanato-3-phenylpropionate (99.0 mL, 0.110 g, 0.501 mmol) in dry CH$_2$Cl$_2$ (5.0 mL) was added 3,4,5-trichloroaniline (0.1952 g, 0.994 mmol) as a solid. The mixture was stirred at room temperature under an argon atmosphere for 20 h. The solution was then concentrated in vacuo and the residue was recrystallized two times from ethyl acetate/hexanes to give 0.14 g (65%) of the pure intermediate urea as a white solid.

A suspension of sodium hydride (0.06 g 60% dispersion in mineral oil, 1.52 mmol) in dry THF (4.0 mL) was treated with a solution of the above urea (0.108 g, 0.260 mmol) in dry THF (4.0 mL). The mixture was stirred at room temperature under an argon atmosphere for 1 h. The mixture was next poured into 100 mL 1 N aqueous HCl. The THF was removed under reduced pressure and the mixture was filtered. The solid was purified by preparative thin layer chromatography ($SiO_2$, 1:1 hexanes/ethyl acetate) to give a white solid which was further purified by recrystallization from absolute EtOH to give 0.027 g of pure compound (28%).

Method F. Synthesis of Succinimides.

Equimolar amounts of the an appropriate starting diacid or anhydride and an appropriate starting aniline are refluxed in a solvent (such as xylene) in the presence of a catalytic amount of base (such as triethylamine) for between about 2 and 24 h. The solvent is removed in vacuo and the residue is dissolved in an organic solvent (such as EtOAc), washed sequentially with aqueous dilute base (such as $NaHCO_3$) and aqueous dilute acid (such as HCl), dried (for example over $MgSO_4$), and concentrated. Purification is performed via, for example, recrystallization or chromatography over silica gel.

The starting diacids and anhydrides are available either commercially or via a number of known literature methods. By way of example, a procedure for the synthesis of 2-benzyl-3-carboxy-2-methylbutanoic acid (the starting material for example 74) is given.

A solution of 2.0 g of 2-methyl-3-phenylpropanoic acid (12.2 mmol), 2.2 g of carbonyl-diimidazole (CDI, 13.56 mmol) in 20 mL of THF was refluxed under nitrogen for 1 h. The temperature was reduced to 50° C. and 1.2 mL of crotyl alcohol (14.1 mmol) was added followed by 20 mg of 4-(N,N-dimethylamino)-pyridine (DMAP). The mixture was heated at 50° C. for 3 h, concentrated and purified by silica gel chromatography to give 1.7 g of the intermediate ester: trans-2-butenyl 2-benzyl-3-carboxy-2-methylbutanoate (64%).

The ester was subjected to a [3,3] sigmatropic rearrangement to produce the next intermediate. Under argon, at −78° C., a solution of 560 mg of the intermediate ester (2.57 mmol) in THF (1 mL) was added to a THF solution of lithium di-isopropylamide (LDA, 3.25 mmol, generated from 1.3 mL of 2.5 M n-BuLi and 0.54 mL of $iPr_2NH$ in 3 mL of THF, −10° C., 15 min) containing 500 microliter of DMPU. The mixture was stirred for 30 min before a solution of 480 mg of TBSCl (3.1 mmol) in 1 mL of THF was added. The mixture was stirred at −78° C. for 30 min, at room temperature for 20 min and then heated at 60° C. for 10 h. The mixture was cooled to 0° C., quenched with 2 N HCl (5 mL) and stirred at room temperature for 10 h. The mixture was made basic with 2 N NaOH to pH 10, extracted with ether (5 mL). The aqueous layer was separated, acidifed to pH 1 with concentrated HCl, extracted with EtOAc and concentrated to give 500 mg (89%) of the intermediate: 2-benzyl-2,3-dimethyl-4-pentenoic acid.

The mono-acid was converted to the desired diacid by oxidation of the terminal alkene with ozone and the resulting intermediate further oxidation with a chromium reagent. Through a solution of 500 mg of 2-benzyl-2,3-dimethyl-4-pentenoic acid (2.29 mmol) in MeOH (20 mL) and methylene chloride (10 mL) containing 120 microliter of pyridine was passed rapidly enough of a stream of $O_3$ at −78° C., such that the solution turned slightly blue. The mixture was treated with 1 mL of methyl sulfide and stirred at −78° C. for 5 min. The mixture was then warmed to room temperature, concentrated and passed through a silica gel column (with 10 % MeOH in $CH_2Cl_2$ as eluting solvent) and concentrated. The crude material was dissolved in 5 mL of acetone and treated with Jones reagent (16 g $CrO_3$ 16 g con. $H_2SO_4$ in 100 mL of $H_2O$) at room temperature until the orange color persisted. After addition of water (10 mL), the mixture was stirred for 1 h, washed with EtOAc and concentrated. The mixture was purified by silica gel chromatography with 3% AcOH-EtOAc to give 300 mg of the desired diacid (55%).

Compounds listed in Table 6 were produced via this method.

TABLE 6

Examples of Compounds Synthesized by Method F.

| EX. | STRUCTURE | STARTING MATERIAL | MELTING POINT (° C.) |
|---|---|---|---|
| 72 | (Racemic) | (Racemic - 3:1 mixture of diastereomers) | oil |

TABLE 6-continued

Examples of Compounds Synthesized by Method F.

| EX. | STRUCTURE | STARTING MATERIAL | MELTING POINT (° C.) |
|---|---|---|---|
| 73 | (Racemic) | (Racemic - 3:1 mixture of diastereomers) | 139–40 |
| 74 | (Racemic) | (Racemic) | 111–2 |
| 75 | 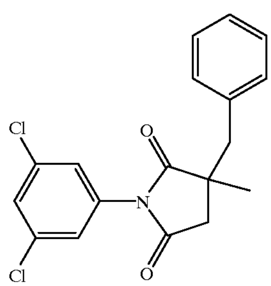 | | 104–5 |
| 76 | 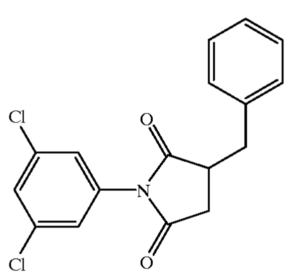 | | 112–3 |

TABLE 6-continued

Examples of Compounds Synthesized by Method F.

| EX. | STRUCTURE | STARTING MATERIAL | MELTING POINT (° C.) |
|---|---|---|---|
| 77 | [structure: 1-(3,5-dichlorophenyl)-3-(4-bromobenzyl)-3-methyl pyrrolidine-2,5-dione] | [structure: 2-methyl-2-(4-bromobenzyl)succinic acid] | not determined |

Method F is exemplified by the synthesis of the compounds of Examples 92 and 93 (see Table 6) which was carried out as follows: A mixture of isomers of the starting diacid of example 92 (0.58 g, 1.8 mmol, 3:1 mixture of isomers), 3,5-dichloroaniline (0.35 g, 2.2 mmol), Et$_3$N (10 mL, 0.07 mmol) in xylene (5 mL) was refluxed under argon in a flask fitted with Dean-Stark trap for 24 h. The mixture was cooled, concentrated and purified by silica gel chromatography (with 10% then with 15% ethyl acetate in hexanes as the eluting solvent) to give 0.45 g (52%)of trans-methyl isomer (example 73, mp 139–140° C.) and 15 mg (2%) of the cis-methyl isomer (example 72, mp=oil).

Method G. Conversion of Carbonyls to Thio-carbonyls

Several reagents are known in the literature which will convert carbonyls to thio carbonyls. A typical sequence involves heating the substrate with a reagent such as P$_2$S$_3$ in a high boiling solvent such as tetralin for between 1 and 48 h. Isolation of the product follows relatively standard conditions such as the dilution of the mixture into an organic solvent such as EtOAc and washing this mixture with water and saturated aqueous NaCl followed by drying and concentration. Purification is accomplished by silica gel chromatography or recrystallization, to afford the desired product.

Compounds listed in Table 7 were produced via this general method.

TABLE 7

Examples of Compounds Synthesized by Method G.

| EXAMPLE | STRUCTURE | STARTING MATERIAL | MELTING POINT (° C.) |
|---|---|---|---|
| 78 | [structure: 1-(3,5-dichlorophenyl)-5-(4-bromobenzyl)-5-methyl-imidazolidine-2,4-dithione] | [structure: 1-(3,5-dichlorophenyl)-5-(4-bromobenzyl)-5-methyl-hydantoin] | 197–8 |

TABLE 7-continued

Examples of Compounds Synthesized by Method G.

| EXAMPLE | STRUCTURE | STARTING MATERIAL | MELTING POINT (° C.) |
|---|---|---|---|
| 79 | (structure) | (structure) | 153–4 |

Method G is exemplified by the synthesis of the compound of Example 78, which was carried out as follows: The starting substrate (1.5 g, 3.5 mmol) was dissolved in 5 mL of tetralin, treated with $P_2S_3$ (0.9 g, 5.7 mmol) and heated to 225° C. for 2 h. Upon cooling, the mixture was diluted with water and the product was extracted into EtOAc. The organic layer was washed with saturated aqueous NaCl, dried and concentrated. The residual oil was triturated with hexanes to produce a yellow solid which was isolated by filtration. This material was further purified by flash chromatography (1:4 EtOAc:Hexanes) to afford 1.13 g (70%%) of the desired compound.

Method H. Selective Hydrolysis of Thio-carbonyls to Carbonyls

The dithio-carbonyl containing compounds produced via Method G can be selectively hydrolyzed to each of the two monothio-carbonyl compounds depending on the choice of conditions. In general the thio-carbonyl at the 4-position of the ring is more susceptible to nucleophilic conditions. As shown in Example 81, it can be converted to the 4-oxo-species by treatment with aqueous ethanolamine followed by acid hydrolysis. The thio-carbonyl at the 2-position of the ring is more nucleophilic at sulfur and can be alkylated with methyl sulfate. This intermediate can then be hydrolyzed with mild acid. This affords the compound of Example 80. Purification of either class of compound is easily performed by silica gel chromatography or recrystallization.

Compounds listed in Table 8 were produced via this general method.

TABLE 8

Examples of Compounds Synthesized by Method H.

| EX. | STRUCTURE | STARTING MATERIAL | REACTION CONDITIONS | MP (° C.) |
|---|---|---|---|---|
| 80 | (structure) | (structure) | 1. $H_2N(CH_2)_2OH$, THF, 100° C.<br>2. 6 N HCl, 100° C. | 153–4 |

TABLE 8-continued

Examples of Compounds Synthesized by Method H.

| EX. | STRUCTURE | STARTING MATERIAL | REACTION CONDITIONS | MP (° C.) |
|---|---|---|---|---|
| 81 | [structure: 1-(3,5-dichlorophenyl)-5-(4-bromobenzyl)-5-methyl-2-oxo-4-thiohydantoin] | [structure: 1-(3,5-dichlorophenyl)-5-(4-bromobenzyl)-5-methyl-2,4-dithiohydantoin] | 1. NaOH, Me$_2$SO$_4$, 0° C.<br>2. 6 N HCl, 100° C. | 174–5 |

Example 80 was prepared by treating a solution of the starting material (0.23 g, 0.49 mmol) in 3 mL of THF with aqueous with 10 mL of 50% aqueous ethanolamine and heating under reflux for 2 h. Upon cooling, the mixture was extracted with EtOAc and the organic layer was washed with water and saturated aqueous NaCl, dried and concentrated to give a brown solid. This solid was then treated with 20 mL of 6 N HCl and heated under reflux for 72 h. Upon cooling, the mixture was extracted with EtOAc and the organic layer was washed with saturated aqueous NaCl, dried and concentrated. The product was purified by preparative TLC over silica gel using 1:1 EtOAc:Hexanes as the solvent to produce the product in 34% yield.

Example 81 was prepared by treating a solution of the starting material (0.5 g, 1.09 mmol) in 1.6 mL of 2 N NaOH. As the compound did not initially dissolve, 1 mL of water and 1 mL of THF were added to aid solubility. This mixture was then cooled in an ice bath and Me$_2$SO$_4$ (0.12 mL, 1.3 mmol) was added dropwise over 5 min. The mixture was stirred another 3 h at 0° C. and then for 45 min at room temperature. The reaction was quenched by the addition of enough 1 N HCl needed to lower the pH of the solution to 2. The mixture was extracted with EtOAc and the organic layer was washed with saturated aqueous NaCl, dried and concentrated to give a yellow oil. This oil was then treated with 10 mL of 6 N HCl and heated under reflux for 3 h. Upon cooling, the mixture was extracted with EtOAc and the organic layer was washed with saturated aqueous NaCl, dried and concentrated. The product was purified by column chromatography over silica gel using 1:1 EtOAc: Hexanes as the solvent to produce the product in 5% yield.

Method I. N-Alkylation of a Hydantoin.

An appropriate hydantoin is dissolved in an aprotic solvent (such as, for example, DMF, THF or DMSO) and treated with one equivalent of a base (such as, for example, NaH, LDA, LiHMDS, KHMDS, KH or NaHMDS). After about 10 min to 1 h an appropriate alkylating agent is added and the mixture stirred at between about room temperature and 90° C. for up to about 24 h. (Progress of the reaction can be monitored using TLC). The solution is then cooled and diluted with an organic solvent (such as, for example, EtOAc or CH$_2$Cl$_2$). The organic phase is washed sequentially with a dilute acid (such as 1 N HCl) and water, dried (for example over MgSO$_4$) and concentrated. The desired hydantoin is purified, as by silica gel chromatography or by recrystallization.

Compounds listed in Table 9 were produced via this general method.

TABLE 9

Examples of Compounds Synthesized by Method I

| EX. | STRUCTURE | STARTING HYDANTOIN | STARTING ALKYLATING AGENT | M.P. (° C.) |
|---|---|---|---|---|
| 82 | [structure: 1-(3,5-dichlorophenyl)-3-methyl-5-benzylhydantoin] | [structure: 1-(3,5-dichlorophenyl)-5-benzylhydantoin] | CH$_3$I | 118–20 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 83 | 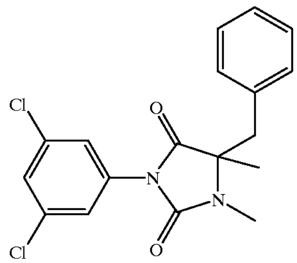 | | CH₃I | 113–4 |
| 84 | 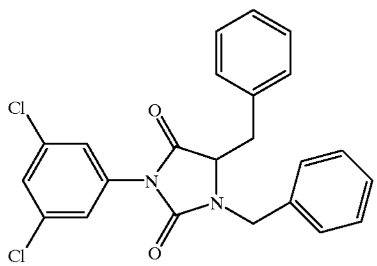 | | PhCH₂Br | 38–40 |
| 85 | 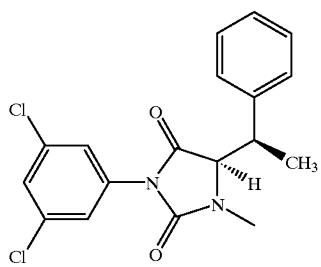 | | CH₃I | oil |
| 86 | 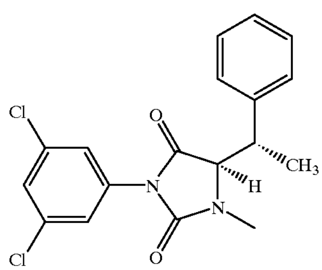 | | CH₃I | oil |
| 87 | 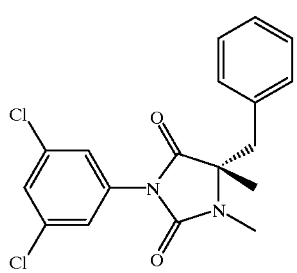 | | CH₃I | 114–5 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 88 | 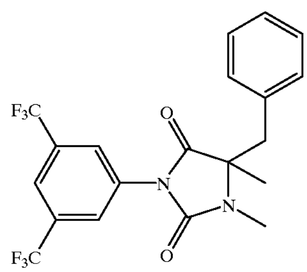 | | CH$_3$I | 112–4 |
| 89 | 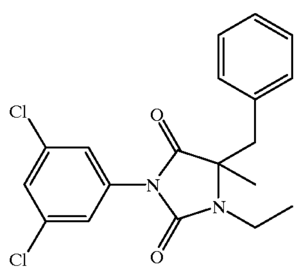 | | CH$_3$CH$_2$I | 107–11 |
| 90 | 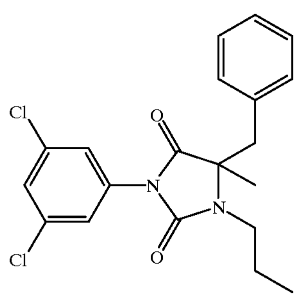 | | CH$_3$CH$_2$CH$_2$I | oil |
| 91 | 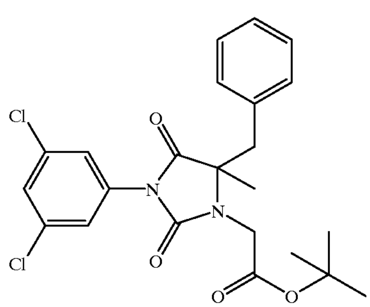 | | BrCH$_2$CO$_2$tBu | 121–3 |
| 92 | 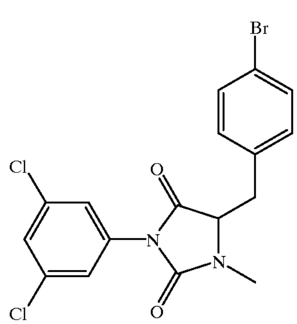 | | CH$_3$I | 143–5 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 93 | 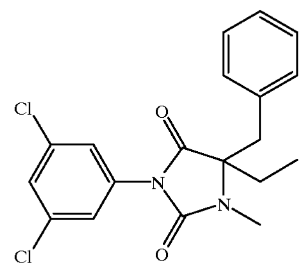 | | $CH_3I$ | 112–3 |
| 94 | 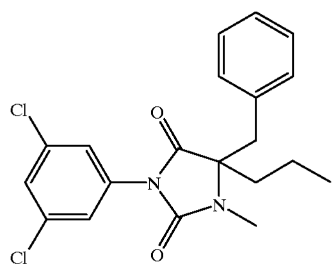 | | $CH_3I$ | 102–4 |
| 95 | 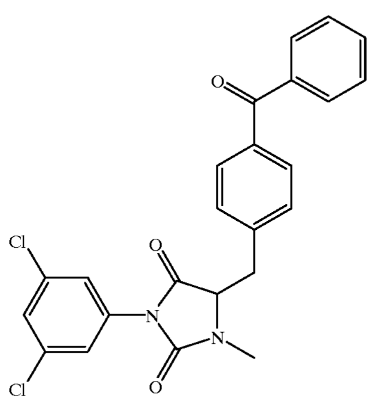 | | $CH_3I$ | 65–7 |
| 96 | 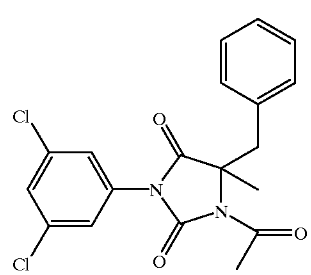 | | $CH_3COCl$ | 110–1 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 97 | 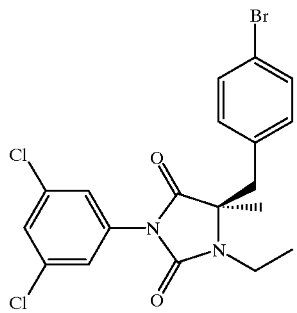 | | CH₃CH₂I | 57–9 |
| 98 | 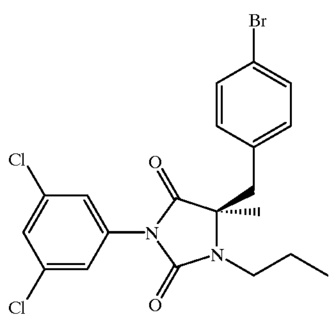 | | CH₃CH₂CH₂Br | 51–3 |
| 99 | 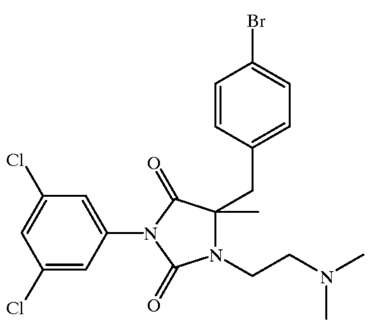 | | Cl(CH₂)₂NMe₂ | oil |
| 100 | 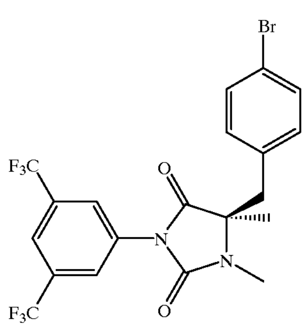 | | CH₃I | 58–60 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 101 | 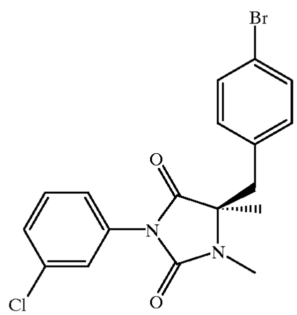 | | CH₃I | 60–2 |
| 102 | 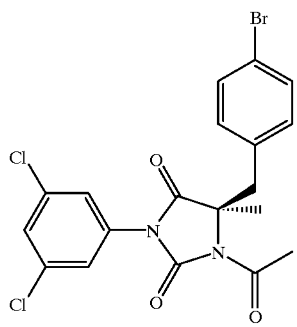 | | CH₃COCl | 111–3 |
| 103 | 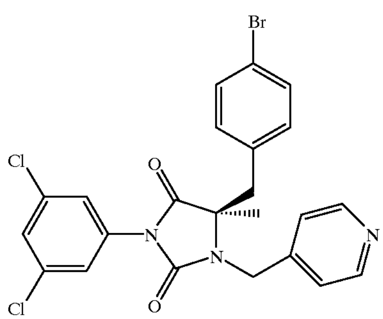 | | | 78–9 |
| 104 | 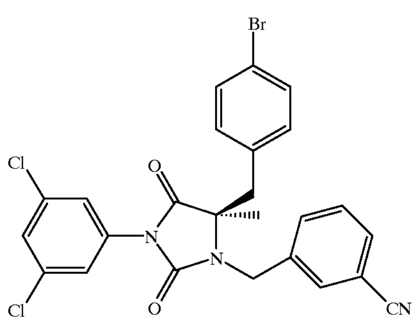 | | | 148–50 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 105 | 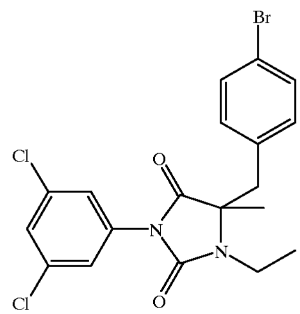 | | CH$_3$CH$_2$I | 135–6 |
| 106 | 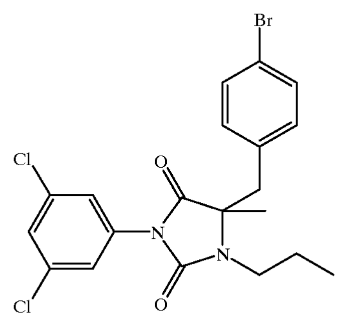 | | CH$_3$CH$_2$CH$_2$Br | 104–6 |
| 107 | 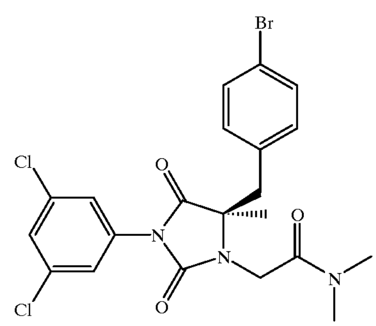 | | | 78–80 |
| 108 | 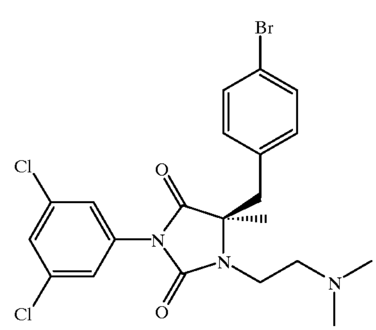 | | Cl(CH$_2$)$_2$NMe$_2$ | 236–7 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 109 | 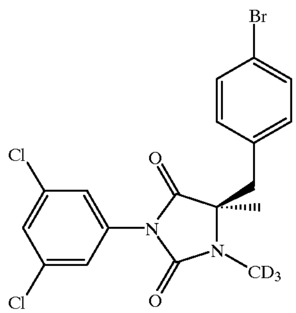 | | CD₃I | 136–8 |
| 110 | 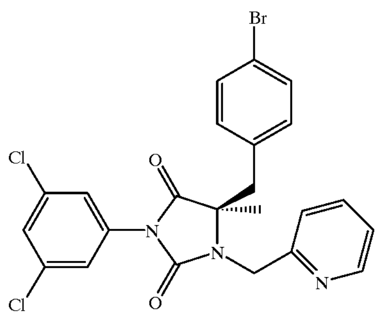 | | | 129–30 |
| 111 | 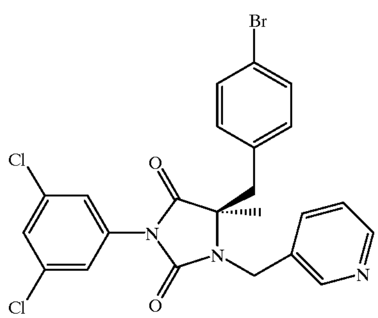 | | | 69–70 |
| 112 | 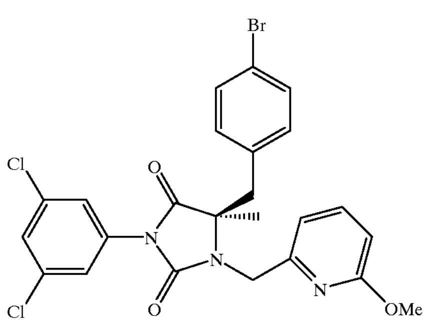 | | | 66–67 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 113 | 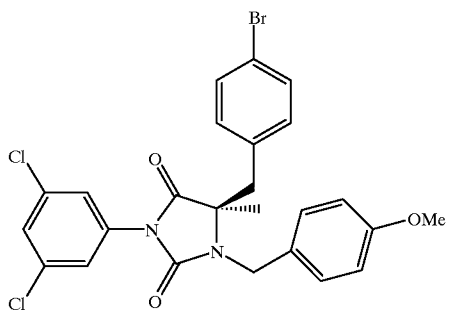 | | | 104–6 |
| 114 | 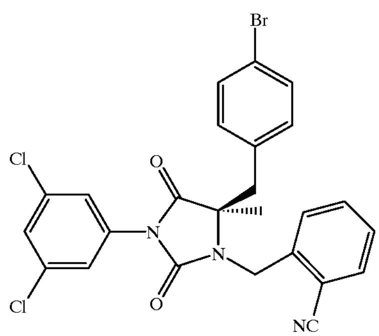 | | | 84–5 |
| 115 | 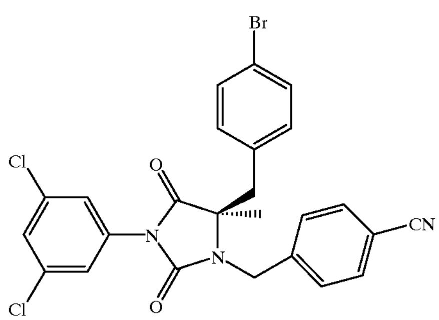 | | | 128–9 |
| 116 | 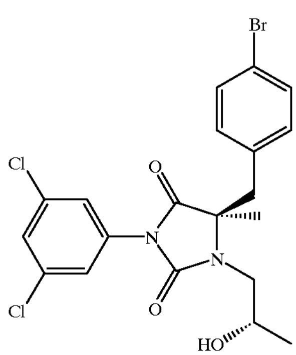 | | | 52–4 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 117 | 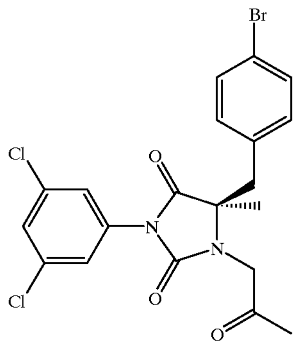 | | ClCH₂C(O)CH₃ | 63–4 |
| 118 | 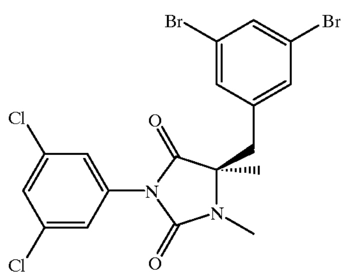 | | CH₃I | 94–5 |
| 119 | 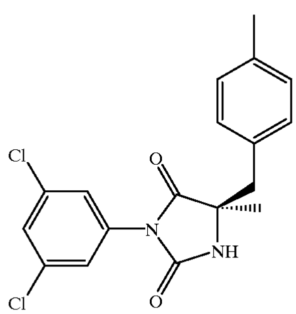 | | CH₃I | 135–6 |
| 120 | 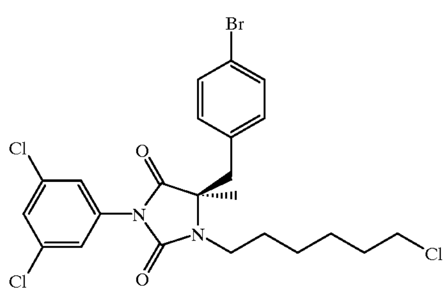 | | Cl(CH₂)₆Br | 104–5 |

TABLE 9-continued

Examples of Compounds Synthesized by Method I

| EX. | STRUCTURE | STARTING HYDANTOIN | STARTING ALKYLATING AGENT | M.P. (° C.) |
|-----|-----------|--------------------|---------------------------|-------------|
| 121 | 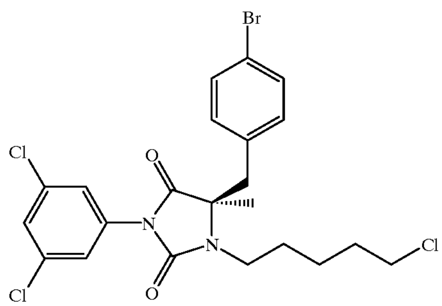 | | Cl(CH$_2$)$_5$Br | 141–2 |
| 122 | 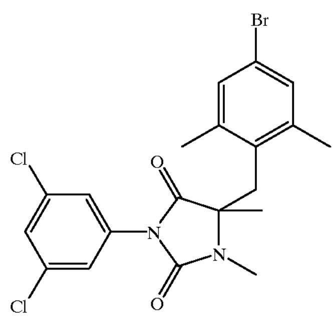 | | CH$_3$I | 128–32 |
| 123 | 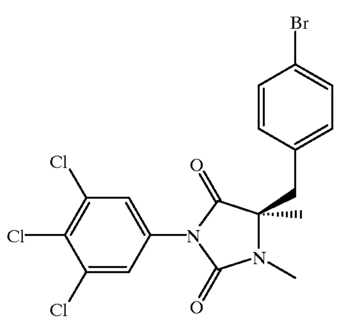 | | CH$_3$I | 54–5 |
| 124 | 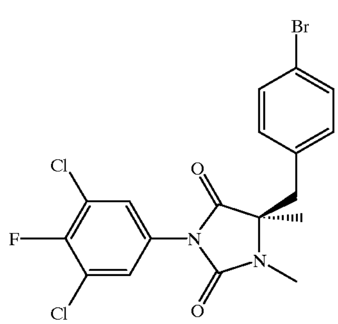 | | CH$_3$I | 71–5 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 125 | 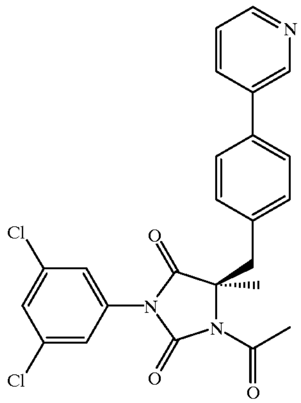 | | CH₃COCl | 57–59 |
| 126 | 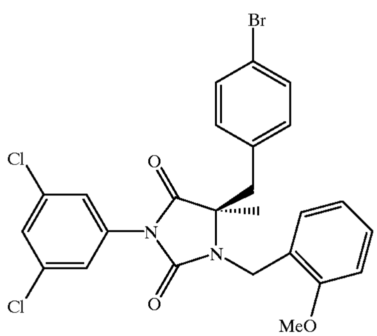 | | | |
| 127 | 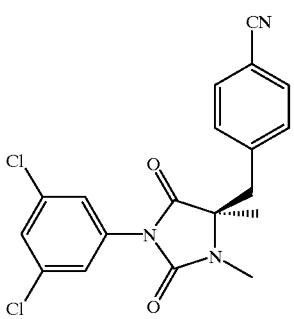 | | CH₃I | 114–5 |
| 128 | 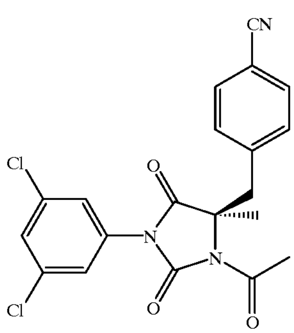 | | CH₃COCl | 153–4 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 129 | 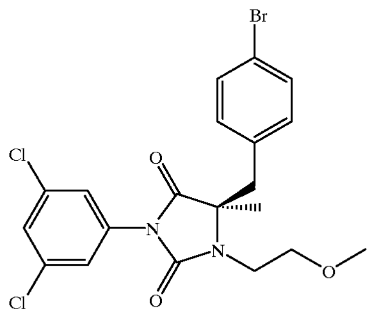 | | Cl(CH$_2$)$_2$OCH$_3$ | oil |
| 130 | 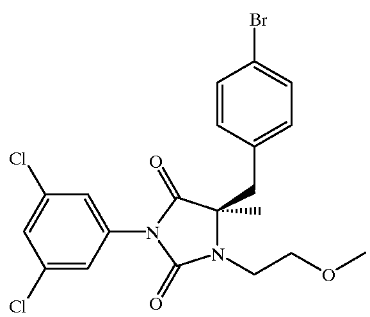 | | | 56–7 |
| 131 | 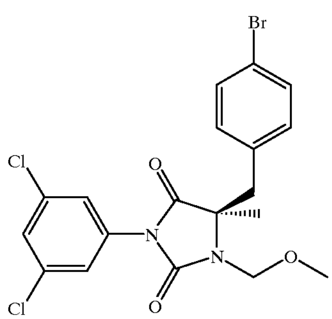 | | ClCH$_2$OCH$_3$ | oil |
| 132 | 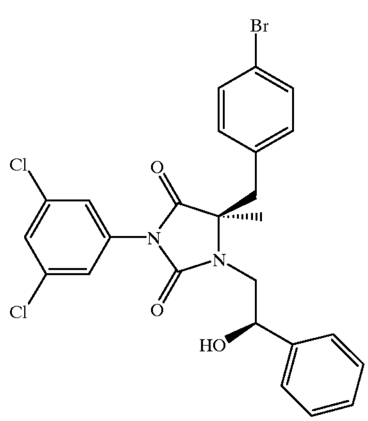 | | | 76–78 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 133 | 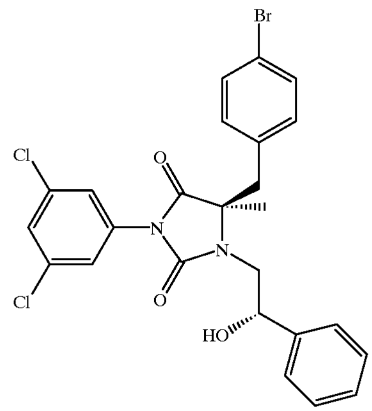 | | (S)-styrene oxide | 76–78 |
| 134 | 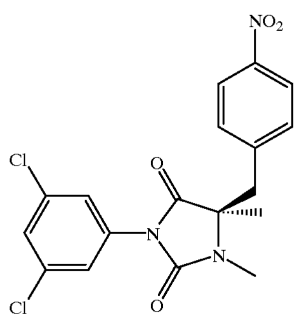 | | $CH_3I$ | oil |
| 135 | 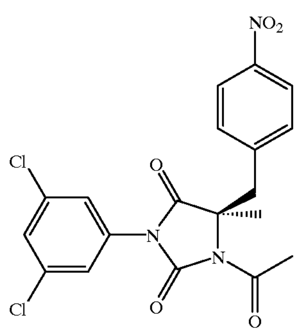 | | $CH_3COCl$ | 105–7 |
| 136 | 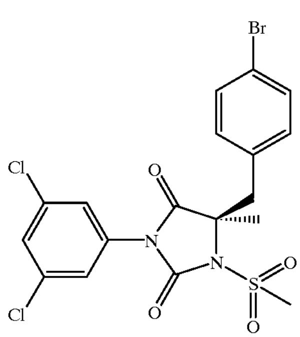 | | $CH_3SO_2Cl$ | 141–3 |

TABLE 9-continued

Examples of Compounds Synthesized by Method I

| EX. | STRUCTURE | STARTING HYDANTOIN | STARTING ALKYLATING AGENT | M.P. (° C.) |
|---|---|---|---|---|
| 137 | (structure) | (structure) | CH₃I | 53–5 |

Method I is exemplified by the synthesis of the compound of Example 97 (see Table 9), which was carried out by dissolving the starting material (0.21 g, 0.5 mmol) in DMF (5 mL) and treating the solution sequentially a solution of 1 M NAHMDS (0.5 mL, 0.5 mmol) and EtI (0.04 mL, 0.5 mmol). After 1 h, the reaction mixture was partitioned between EtOAc and water, and the organic phase washed with water and dried over MgSO$_4$. Column chromatography over silica gel produced 0.17 g (72%) of the desired product.

Method J. C-Alkylation of a Heterocycle.

An appropriate heterocycle is dissolved in an aprotic solvent (such as DMF, TBF or DMSO) and treated with one equivalent of a base, (such as Et$_3$N, LDA, KHMDS, LiH-MDS or NaHMDS) at between about −78° C. and room temperature. After about 10 min to 2 h an appropriate alkylating agent is added and the mixture stirred at between about 0 and 90° C. for up to about 24 h. (Progress of the reaction can be monitored using TLC). The solution is then cooled and diluted with an organic solvent (such as, for example, EtOAc). The organic phase is washed sequentially with dilute aqueous acid (such as 1 NHCl), and with water, dried (for example, over MgSO$_4$) and concentrated. The desired hydantoin is purified, as by silica gel chromatography or by recrystallization.

Compounds listed in Table 10 were produced via this general method.

TABLE 10

Examples of Compounds Synthesized by Method J.

| EX. | STRUCTURE | STARTING HYDANTOIN | STARTING ALKYLATING AGENT | M.P. (° C.) |
|---|---|---|---|---|
| 138 | (structure) | (structure) | CH₃I | not determined |

TABLE 10-continued
Examples of Compounds Synthesized by Method J.
| EX. | STRUCTURE | STARTING HYDANTOIN | STARTING ALKYLATING AGENT | M.P. (° C.) |
|---|---|---|---|---|
| 139 | 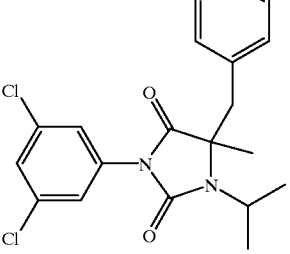 | 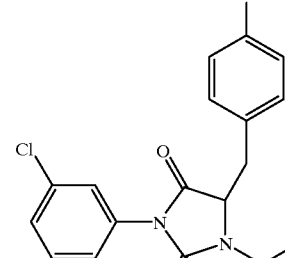 | CH₃I | oil |
| 140 | 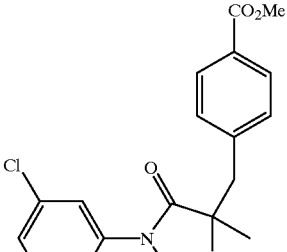 | 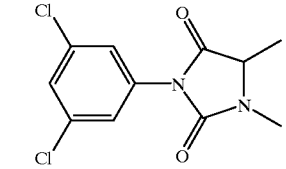 | 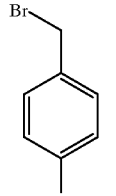 | 48–50 |
| 141 | 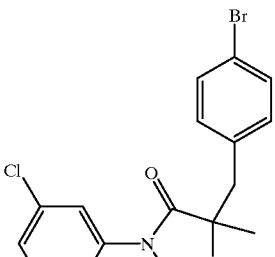 | 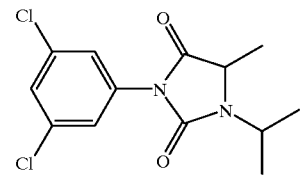 | 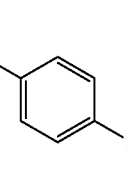 | 125–7 |
| 142 | 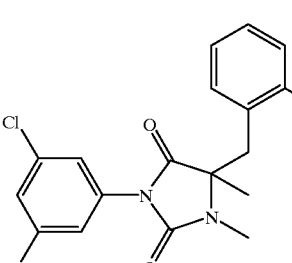 | 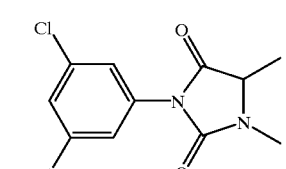 | 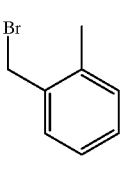 | 95–6 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 143 | 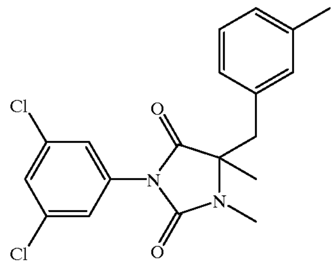 | | | 97–8 |
| 144 | 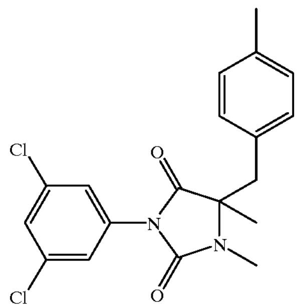 | | | 106–7 |
| 145 | 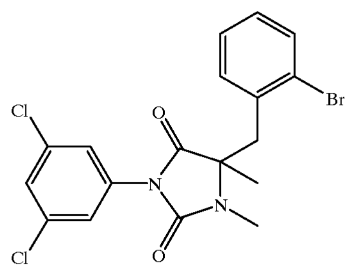 | | | 105–6 |
| 146 | 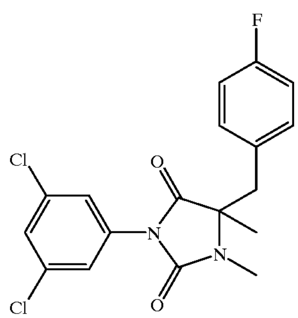 | | | 110–2 |
| 147 | 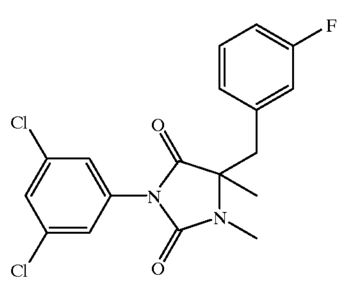 | | | 106–8 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 148 | 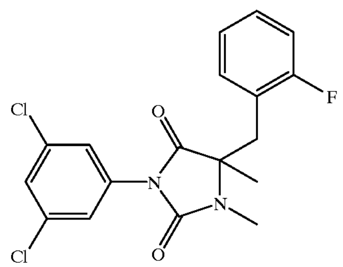 | | | 82–3 |
| 149 | 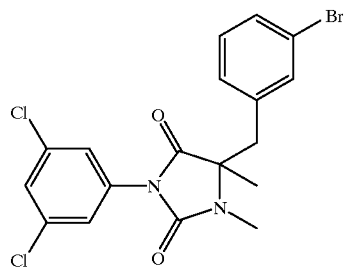 | | | 124–6 |
| 150 | 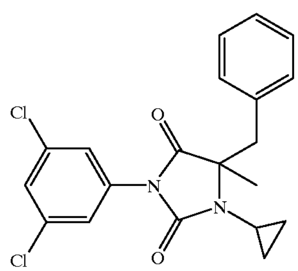 | | | oil |
| 151 | 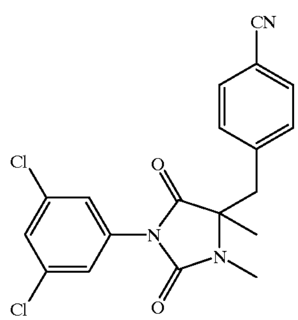 | | | 166–8 |
| 152 | 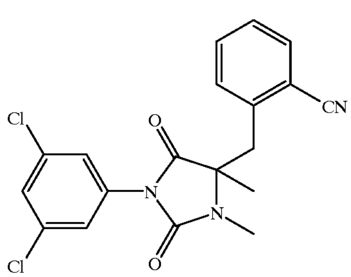 | | | 62–4 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 153 | 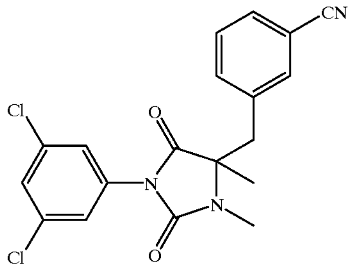 | | | 124–6 |
| 154 | 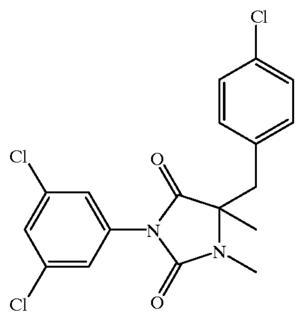 | | | 96–8 |
| 155 | 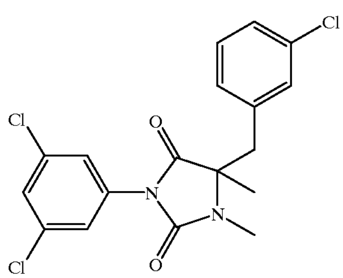 | | | 105–7 |
| 156 | 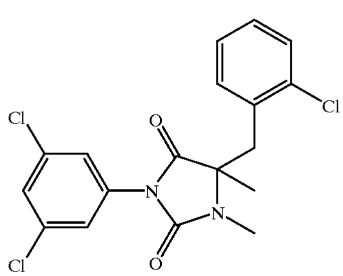 | | | 106–8 |
| 157 | 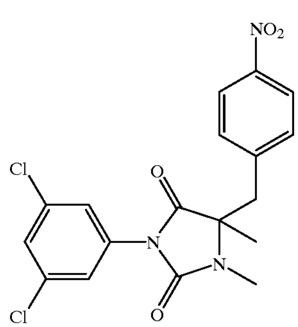 | | | 50–2 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 158 | 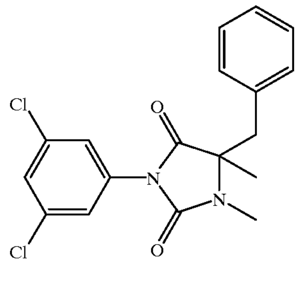 | | $CH_3I$ | not determ. |
| 159 | 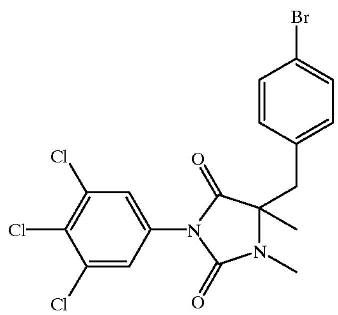 | | | 160–1 |
| 160 | 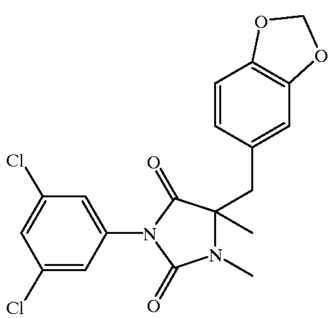 | | | 166–7 |
| 161 | 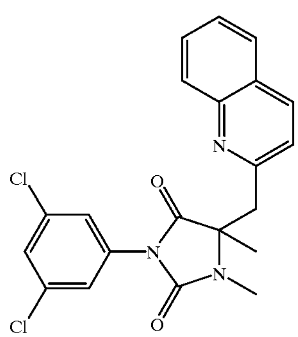 | | | 65–66 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 162 | 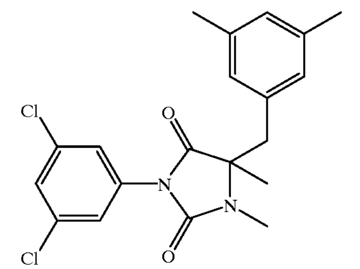 | | | 143–4 |
| 163 | 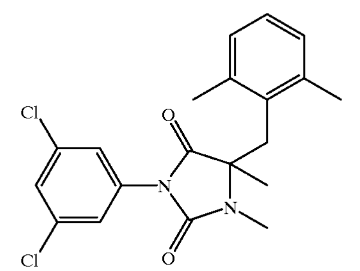 | | | not determined |
| 164 | 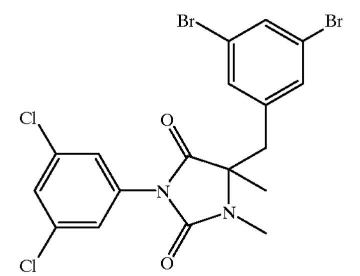 | | | 138–9 |
| 165 | 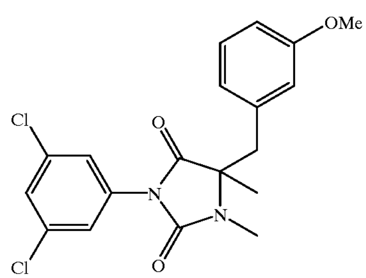 | | | 114–5 |
| 166 | 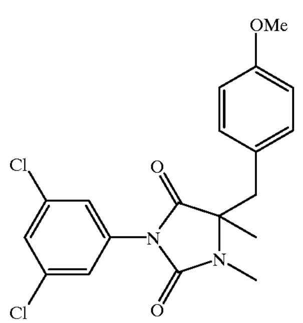 | | | 125–6 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 167 | 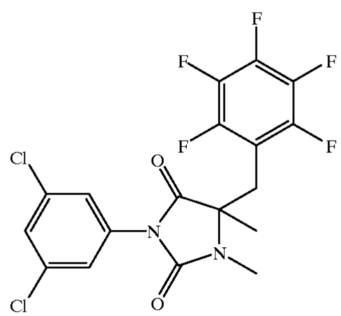 | | | 37–9 |
| 168 | 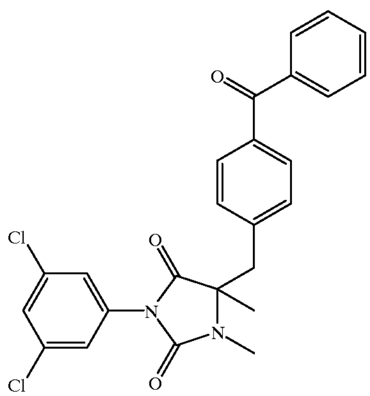 | | CH₃I | 53–5 |
| 169 | 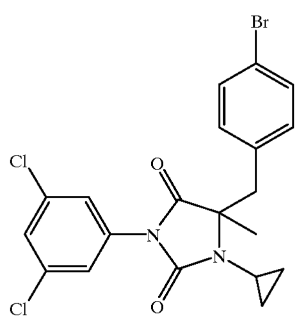 | | | 98–100 |
| 170 | 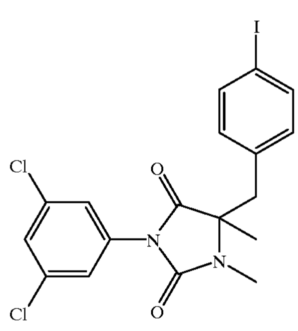 | | | 65–66 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 171 | 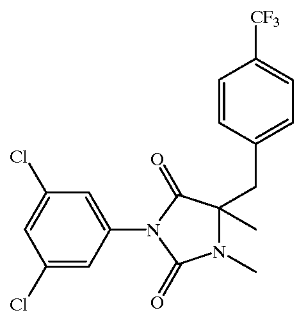 | | | 120–1 |
| 172 | 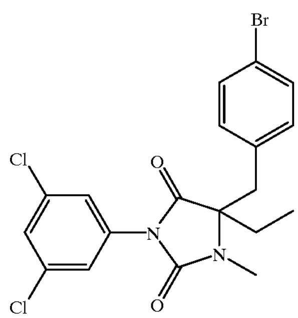 | | $CH_3CH_2I$ | 55–6 |
| 173 | 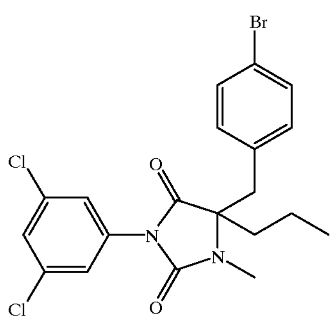 | | $CH_3CH_2CH_2Br$ | 51–3 |
| 174 | 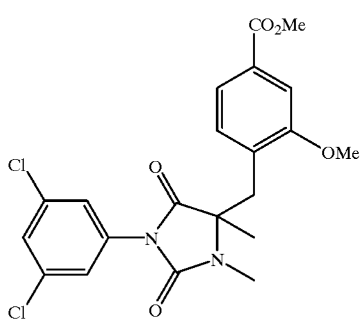 | | | 127–8 |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 175 | 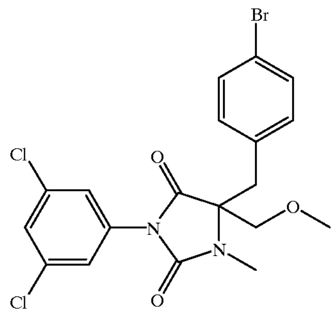 | | ClCH$_2$OCH$_3$ | 54–5 |
| 176 | 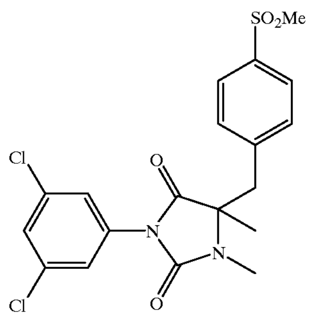 | | | 159–60 |
| 177 | 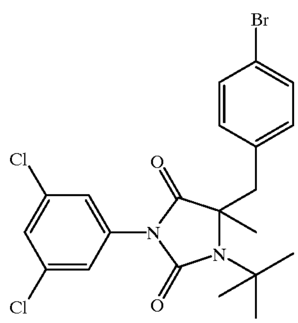 | | | 77–9 |
| 178 | 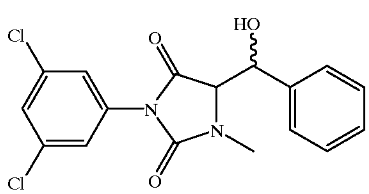 | | | 77–9 |
| 179 | 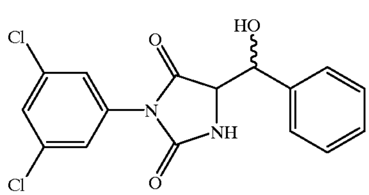 | | | oil |

TABLE 10-continued

Examples of Compounds Synthesized by Method J.

| EX. | STRUCTURE | STARTING HYDANTOIN | STARTING ALKYLATING AGENT | M.P. (° C.) |
|---|---|---|---|---|
| 180 | [structure] | [structure] | [structure] | 120–1 |

Method J is exemplified by the synthesis of the compound of Example 148 (see Table 10), which was carried out is as follows. The starting material (0.11 g, 0.40 mmol) was dissolved in THF (5.0 mL) and cooled in a dry-ice/acetone bath (approximately −78° C.). Lithium bis(trimethylsilyl) amide (LiHMDS, 405.0 µL, 0.40 mmol) was added dropwise. The resultant yellow solution was stirred in the cold bath for 15 minutes, at which point 2-fluorobenzyl bromide was added to it. The mixture was stirred at this temperature for an additional 30 minutes and then at 0° C. for 30 minutes. The reaction mixture was next poured into 1 N HCl (40 mL) and extracted into EtOAc (50 mL). The organic layer was washed with saturated aqueous NaCl (35 mL), dried ($Na_2SO_4$), filtered, and concentrated in vacuo to afford 0.16 g of crude product. This material was purified by flash chromatography over silica gel (1:3 EtOAc/Hexanes) to afford 0.87 g (57.0%) of the compound of example 148.

Method K. C-Alkylation of Hydantoins using Methyl Magnesium Carbonate

As reported by Finkbeiner (J. Org. Chem. 1965, 30, 3414), hydantoins can be C-alkylated with alkyl halides using magnesium methyl carbonate (MMC). A solution of MMC in an organic solvent (such as DMF) is saturated at about 80° C. with $CO_2$ over a period of about 1 h. An appropriate hydantoin is then added and heated with the MMC for about 1 to 2 h, at which point an appropriate alkyl halide is added. The reaction mixture is then warmed to about 110° C. for between about 2 to 3 h, then cooled to about room temperature. The mixture is then poured into concentrated aqueous acid (such as HCl) over ice and cooled. The solid formed is collected by filtration and purified by silica gel chromatography and/or via recrystallization to afford the desired product.

The compound listed in the Table 11 was produced via this method.

TABLE 11

Example of Compound Synthesized by Method K.

| EX. | STRUCTURE | STARTING MATERIAL | MELTING POINT (° C.) |
|---|---|---|---|
| 181 | [structure] | [structure] | 213–4 |

Method K is exemplified by the synthesis of the compound of Example 181 (see Table 11), which was carried out as follows: A dry two-necked round bottom-flask was evacuated and charged with a $CO_2$ atmosphere. Magnesium methyl carbonate in DMF (860 µL 2.0 M) was added to the flask and the solution was heated to 80° C. $CO_2$ was introduced from a dry-ice vessel via a cannula connected to the reaction vessel and was bubbled through the solution for 1.0 h at which point an argon line was attached and the cannula was removed. The starting material (0.21 g, 0.86 mmol) in DMF (4.0 mL) was added and the reaction mixture was heated at 80° C. for 1.5 h. A solution of 3-picolyl chloride (0.12 g, 0.94 mmol-HCl salt was first free-based with NaOH) in DMF (1.0 mL) was then added dropwise. The temperature of the oil bath was increased to 110° C. and the mixture was heated at this temperature for 4.0 h. Upon cooling to room temperature the mixture was poured into a mixture 5 mL concentrated HCl and 10 g ice, then stored in a refrigerator overnight. The solution was next neutralized to pH 7–8 with 6 N NaOH and the resulting solid collected by suction filtration and washed with ice-water. Drying of the compound at 50° C. in vacuo afforded 0.20 g of crude product. This was purified by flash chromatography (5%

MeOH/CH$_2$Cl$_2$) to afford 0.06 g of a material which was further purified by recrystallization with EtOH afforded 0.04 g (14.9%) of the compound of example 181.

Method L. Synthesis of Compounds using Pd Catalyzed Cross Coupling

An appropriately substituted arylboronic acid or arylstanane is mixed with an aryl halide or aryl triflate and a catalytic amount of tetrakis(triphenylphosphine)palladium in an appropriate solvent system (such as benzene containing ethanol and aqueous Na$_2$CO$_3$, DMF, NMP or THF) under an inert atmosphere. Other components such as, for example LiCl and triethylamine, may be added as necessary. The mixture is heated at between about 50 and 150° C. for between about 2 and 48 h. The mixture is next cooled and diluted with an organic solvent (such as EtOAc). The organic phase was washed successively with water and saturated aqueous NaCl, dried (as with Na$_2$SO$_4$) and concentrated to give an impure mixture from which the desired material is isolated using silica gel chromatography.

The compounds listed in Table 12 were produced via this method.

TABLE 12

Example of Compound Synthesized by Method L

| EX. | STRUCTURE | STARTING MATERIAL | COUPLING PARTNER | MP (° C.) |
|---|---|---|---|---|
| 182 | 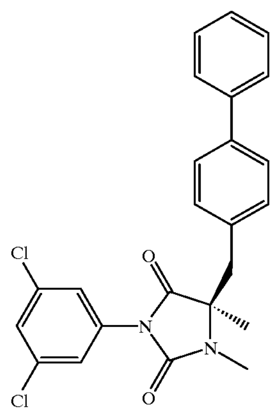 | | | 57–8 |
| 183 | 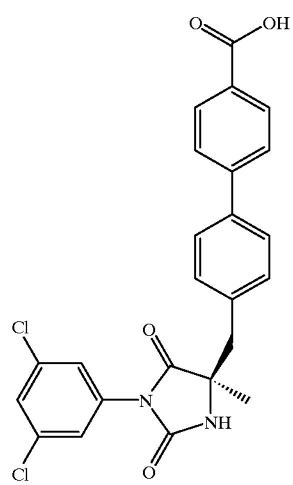 | | | 150–1 |

TABLE 12-continued

Example of Compound Synthesized by Method L

| EX. | STRUCTURE | STARTING MATERIAL | COUPLING PARTNER | MP (° C.) |
|-----|-----------|-------------------|------------------|-----------|
| 184 | 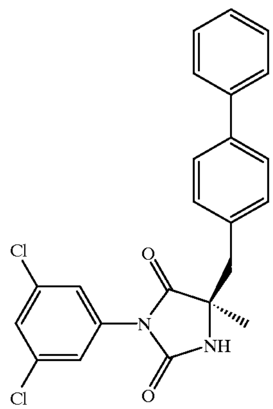 | | | 82–4 |
| 185 | 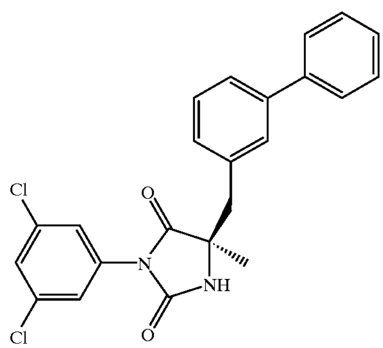 | | | 53–4 |
| 186 | 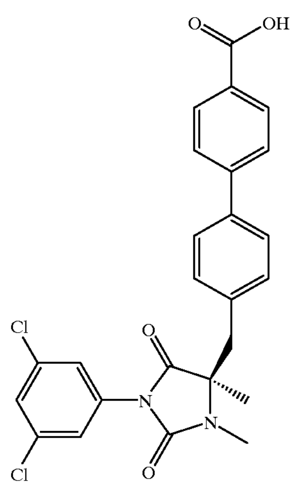 | | | 136–8 |

TABLE 12-continued

Example of Compound Synthesized by Method L

| EX. | STRUCTURE | STARTING MATERIAL | COUPLING PARTNER | MP (° C.) |
|---|---|---|---|---|
| 187 | 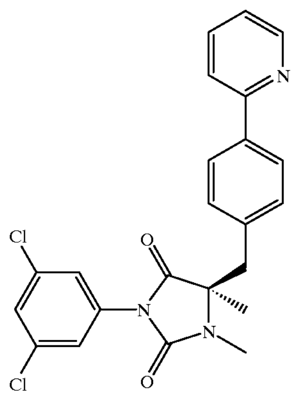 | | | 89–90 |
| 188 | 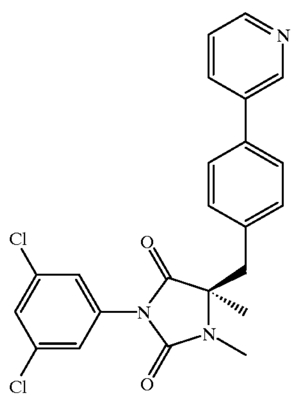 | | | 56–57 |
| 189 | 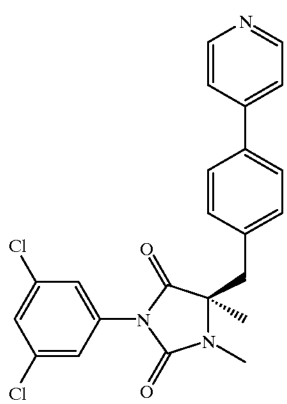 | | | 69–70 |

TABLE 12-continued

Example of Compound Synthesized by Method L

| EX. | STRUCTURE | STARTING MATERIAL | COUPLING PARTNER | MP (° C.) |
|-----|-----------|-------------------|------------------|-----------|
| 190 | (3-pyridyl-phenyl hydantoin with 3,5-dichlorophenyl, methyl) | 4-bromobenzyl hydantoin | 3-pyridyl-SnBu₃ | 77–9 |
| 191 | (2-chlorobiphenyl hydantoin with 3,5-dichlorophenyl, methyl) | 4-iodobenzyl hydantoin | 2-chlorophenyl B(OH)₂ | 76–8 |
| 192 | (4-methyl-3-nitrobiphenyl hydantoin with 3,5-dichlorophenyl, methyl) | 4-iodobenzyl hydantoin | 4-methyl-3-nitrophenyl B(OH)₂ | 201–2 |

TABLE 12-continued

Example of Compound Synthesized by Method L

| EX. | STRUCTURE | STARTING MATERIAL | COUPLING PARTNER | MP (° C.) |
|---|---|---|---|---|
| 193 | 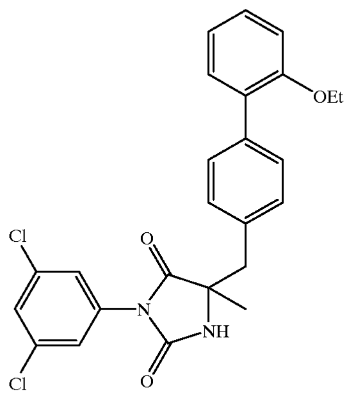 | | | 70–3 |
| 194 | 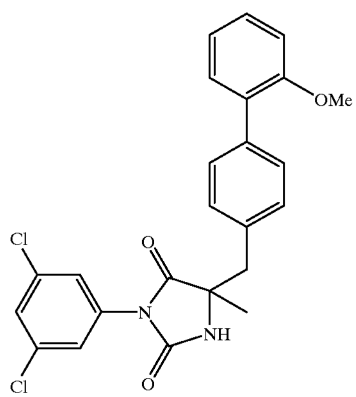 | | | 77–80 |
| 195 | 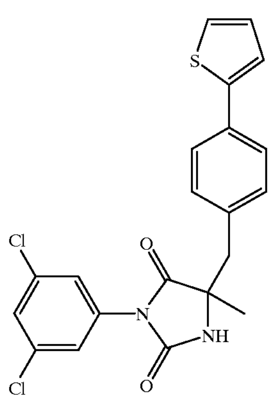 | | | 74–7 |

TABLE 12-continued

Example of Compound Synthesized by Method L

| EX. | STRUCTURE | STARTING MATERIAL | COUPLING PARTNER | MP (° C.) |
|---|---|---|---|---|
| 196 | 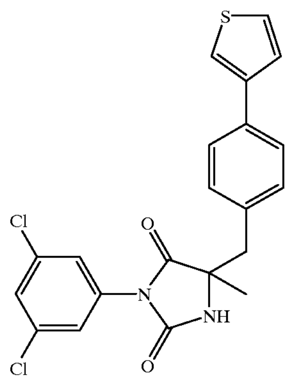 | | | 73–5 |
| 197 | 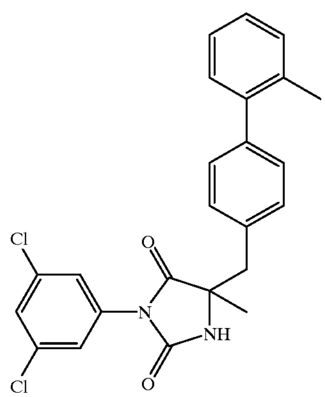 | | | 148–9 |
| 198 | 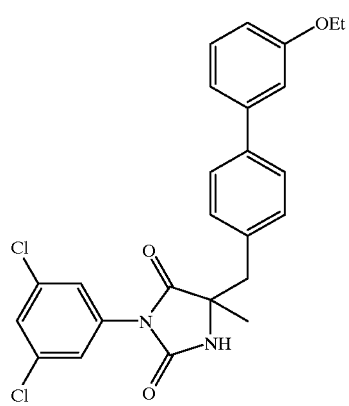 | | | 65–8 |

TABLE 12-continued
Example of Compound Synthesized by Method L
| EX. | STRUCTURE | STARTING MATERIAL | COUPLING PARTNER | MP (° C.) |
|---|---|---|---|---|
| 199 | 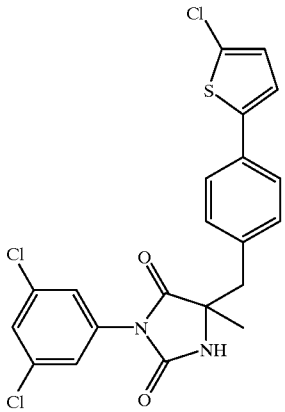 | 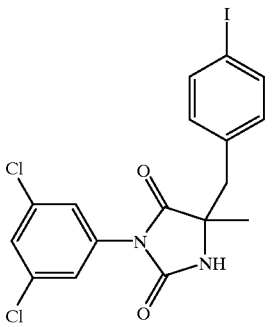 | 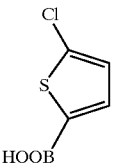 | 143–4 |
| 200 | 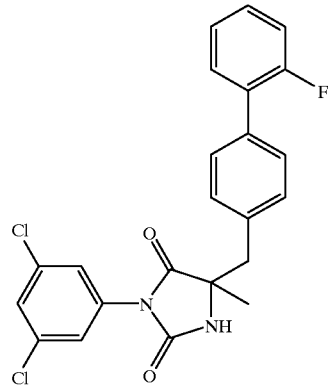 | 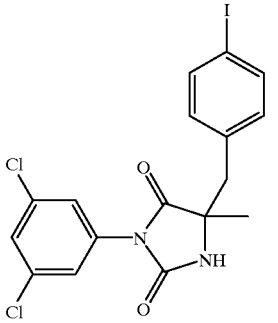 | 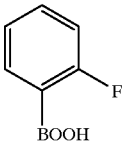 | 69–70 |
| 201 | 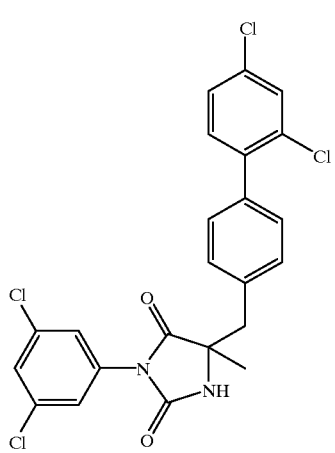 | 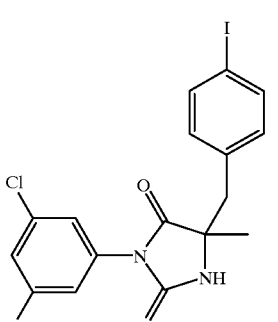 | 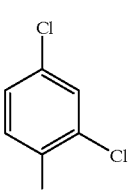 | 97–99 |

TABLE 12-continued

Example of Compound Synthesized by Method L

| EX. | STRUCTURE | STARTING MATERIAL | COUPLING PARTNER | MP (° C.) |
|---|---|---|---|---|
| 202 | 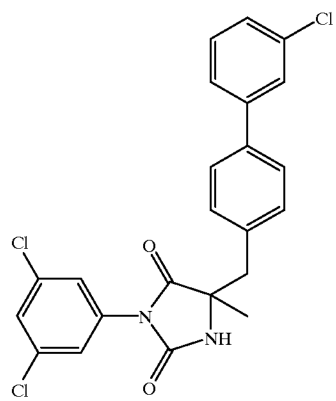 | | | 165–6 |
| 203 | 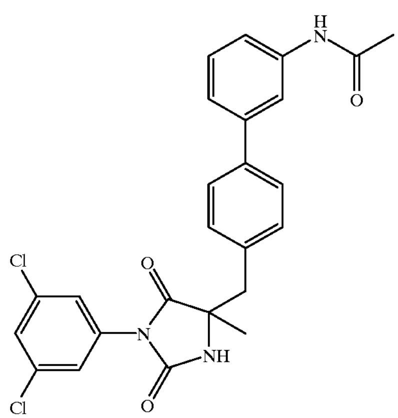 | | | 119–20 |
| 204 | 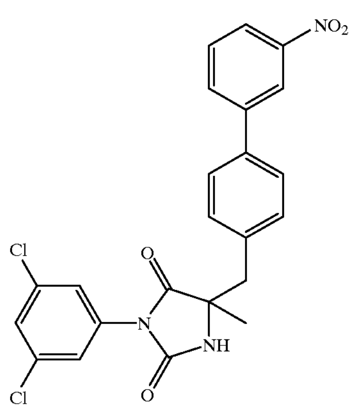 | | | 199–201 |

TABLE 12-continued

Example of Compound Synthesized by Method L

| EX. | STRUCTURE | STARTING MATERIAL | COUPLING PARTNER | MP (° C.) |
|---|---|---|---|---|
| 205 | 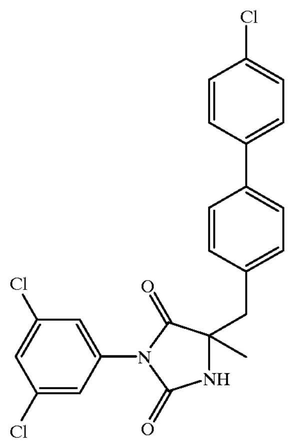 | | | 168–170 |
| 206 | 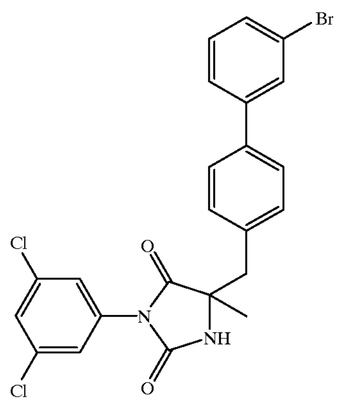 | | | 69–70 |
| 207 | 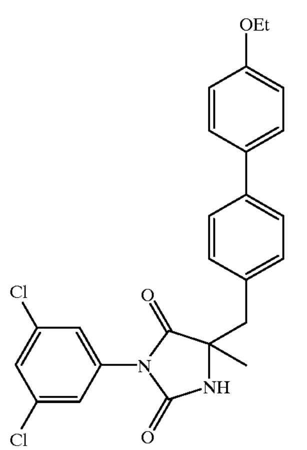 | | | 70–2 |

TABLE 12-continued
Example of Compound Synthesized by Method L
| EX. | STRUCTURE | STARTING MATERIAL | COUPLING PARTNER | MP (° C.) |
|---|---|---|---|---|
| 208 | 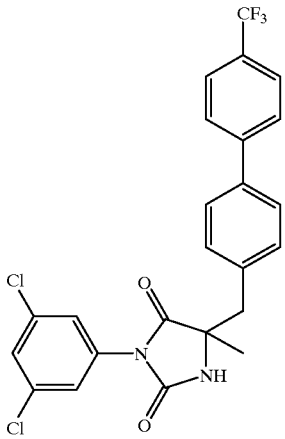 | 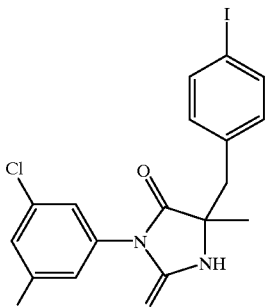 | 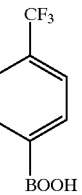 | 163–4 |
| 209 | 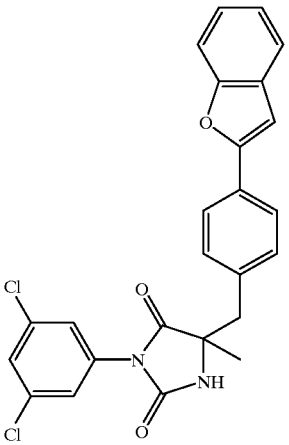 | 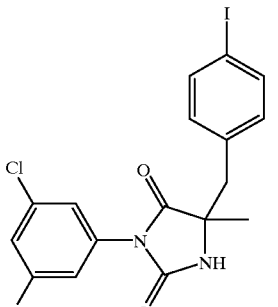 | 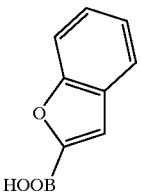 | 110–111 |
| 210 | 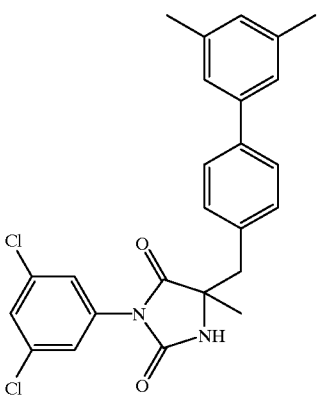 | 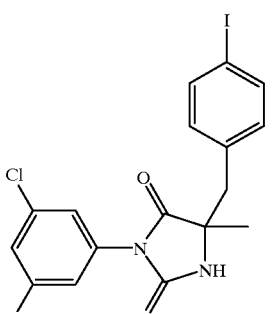 | 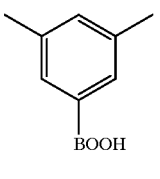 | 75–76 |

TABLE 12-continued

Example of Compound Synthesized by Method L

| EX. | STRUCTURE | STARTING MATERIAL | COUPLING PARTNER | MP (° C.) |
|---|---|---|---|---|
| 211 | 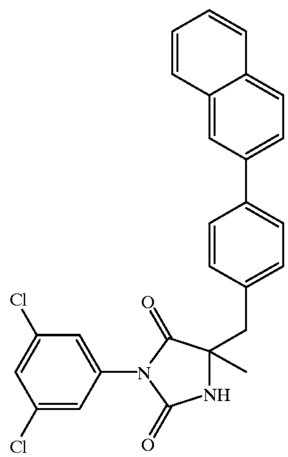 | | naphthalen-2-yl-BOOH | 80–1 |
| 212 | 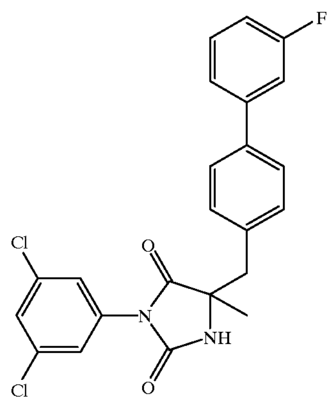 | | 3-F-C6H4-BOOH | 66–68 |
| 213 | 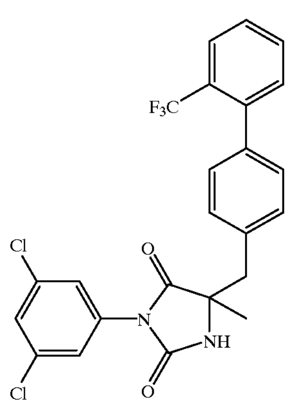 | | 2-(F3C)-C6H4-COOH | 180–3 |

TABLE 12-continued

Example of Compound Synthesized by Method L

| EX. | STRUCTURE | STARTING MATERIAL | COUPLING PARTNER | MP (° C.) |
|---|---|---|---|---|
| 214 | (structure) | (structure) | (structure) MeO-phenyl-BOOH | 71–3 |

Method L s exemplified by the synthesis of the compound of Example 182 (see Table 12) which was carried out as follows: In the manner taught by Miyaura, M; Yanagi, T; Suzuki, A. *Synth. Commun.* 1981, 11, 513, the starting material (0.24 g, 0.54 mmol) was mixed with phenylboric acid (0.73 g, 0.60 mmol), tetrakis-(triphenylphosphine) palladium(0) (0.31 g, 0.03 mmol), sodium carbonate (0.19 g, 1.79 mmol), benzene (3.0 mL), water (1.0 mL), and ethanol (1.0 mL) and stirred under reflux for 12 h. The reaction mixture was then poured into EtOAc (70 mL) and washed successively with water and saturated aqueous NaCl. The organic layer was dried ($Na_2SO_4$), filtered and concentrated in vacuo to afford 0.25 g of crude product. This material was purified by two successive silica gel chromatography columns (1:3 then 1:1 EtOAc/Hexanes) to produce 0.11 g (48%) of the compound of example 183.

Method M. Synthesis of Compounds using Carbonylative Pd Catalyzed Cross Coupling An appropriately substituted arylboronic acid or arylstanane is mixed with an aryl halide or aryl triflate and a catalytic amount of tetrakis(triphenylphosphine) palladium in an appropriate solvent system (such as benzene containing ethanol and aqueous $Na_2CO_3$, DMF, NMP or THF) under an atmosphere of carbon monoxide. Other components such as, for example LiCl and triethylamine, may be added as necessary. The mixture is heated at between about 50 and 150° C. for between about 2 and 48 h. The mixture is next cooled and diluted with an organic solvent (such as EtOAc). The organic phase was washed successively with water and saturated aqueous NaCl, dried (as with $Na_2SO_4$) and concentrated to give an impure mixture from which the desired material is isolated using silica gel chromatography.

The compounds listed in Table 13 were produced via this method.

TABLE 13

Example of Compounds Synthesized by Method K

| EX. | STRUCTURE | STARTING MATERIAL | COUPLING PARTNER | MP (° C.) |
|---|---|---|---|---|
| 215 | (structure) | (structure) | $SnBu_3$-phenyl | 60–2 |

TABLE 13-continued

Example of Compounds Synthesized by Method K

| EX. | STRUCTURE | STARTING MATERIAL | COUPLING PARTNER | MP (° C.) |
|---|---|---|---|---|
| 216 | 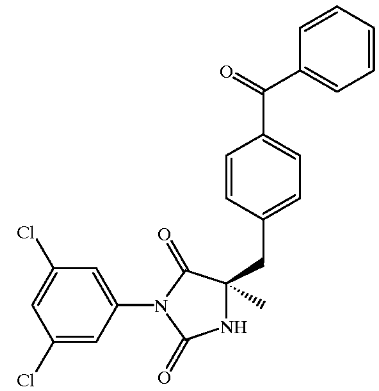 | | | 99–100 |

Method M is exemplified by the synthesis of the compound of Example 215 (see Table 13) which was carried out as follows: the starting material (0.23 g, 0.53 mmol) was mixed with phenyltributylstannane (0.86 mL, 2.64 mmol), bis-triphenylphosphine-palladium(II) chloride (0.037 g, 0.05 mmol), DMF (10.0 mL), and LiCl (5.1 mg, 1.6 mmol), the reaction mixture was then purged with argon, charged with CO and stirred at 115° C. for 12 h. The reaction mixture was then poured into 1 M tetrabutylammonium fluoride (10 mL), then diluted with 95 mL of EtOAc and washed successively with water and saturated aqueous NaCl. The organic layer was dried ($Na_2SO_4$), filtered and concentrated in vacuo to afford 1.2 g of crude product. This material was purified by silica gel chromatography (1:3 EtOAc/Hexanes) to produce 0.14 g (48%) of the compound of example 215.

Method N. Electrophilic Aromatic Substitution

Compounds containing aromatic rings can be modified by numerous reagents via electrophilic aromatic substitution. These include techniques for acylation, nitration, sulfonation and halogenation of these rings.

The compound listed in Table 14 was produced via this method.

The compound of Example 217 is one such case and was prepared by the following procedure. A solution of the starting material (0.4 g, 1.1 mmol) in 1 mL of HOAc and 0.1 mL of $H_2S_4$ was treated with $NaIO_3$ (0.05 g, 0.2 mmol) and $I_2$ (0.06 g, 0.5 mmol). The mixture was then heated to 70° C. for 19 h after which point it was cooled to ambient temperature, extracted several times into EtOAc. The EtOAc was concentrated and the product was isolated after purification by silica gel chromatography. Yield: 33 mg (30%).

Method O. Deprotection of Compounds Protected with Acid-abile Groups

Compounds having acid-labile protecting groups may be deprotected by treatment under acidic conditions, in a known per se manner. Generally this involves treating the substrate with TFA, cation exchange resin (H+), HCl or HBr in AcOH with or without heating. The compound thus formed is collected by filtration or extraction and purified, as by silica gel chromatography or recrystallization, to afford the desired product.

Compounds listed in Table 15 were produced via this general method.

TABLE 14

Example of Compound Synthesized by Method N

| EXAMPLE | STRUCTURE | STARTING MATERIAL | MELTING POINT (° C.) |
|---|---|---|---|
| 217 | 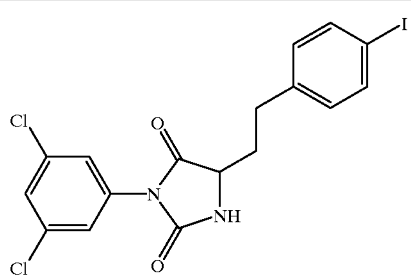 | | 160–1 |

TABLE 15

Examples of Compounds Synthesized by Method O

| EXAMPLE | STRUCTURE | STARTING MATERIAL | MELTING POINT (° C.) |
|---|---|---|---|
| 218 | 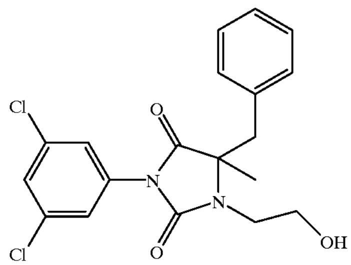 | | 195–6 |
| 219 | 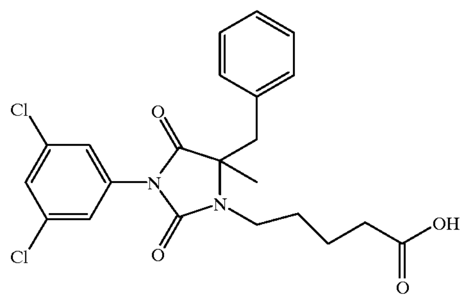 | | 139–40 |
| 220 | 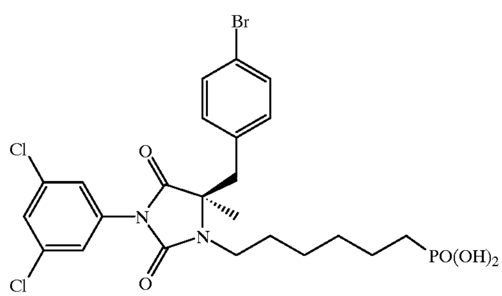 | | oil |
| 221 | 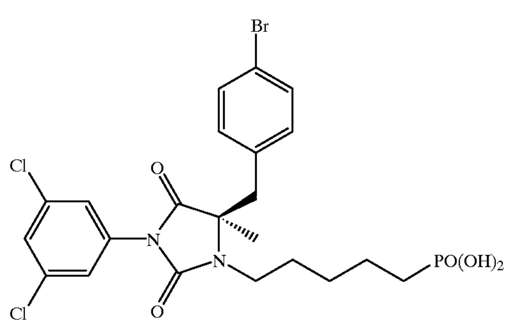 | | oil |

TABLE 15-continued

Examples of Compounds Synthesized by Method O

| EXAMPLE | STRUCTURE | STARTING MATERIAL | MELTING POINT (° C.) |
|---|---|---|---|
| 222 | 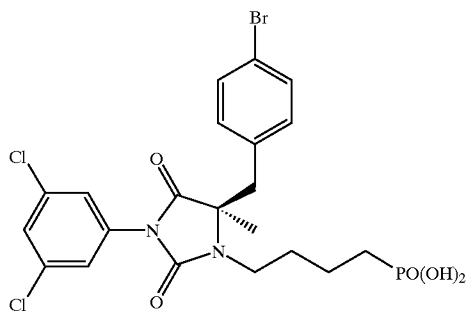 | | oil |
| 223 | 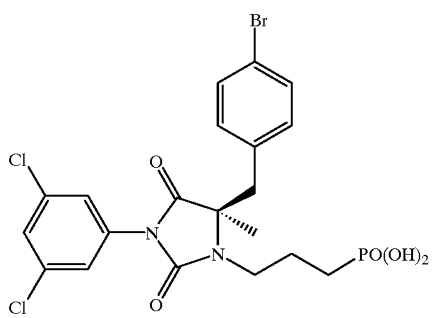 | | 84–5 |
| 224 | 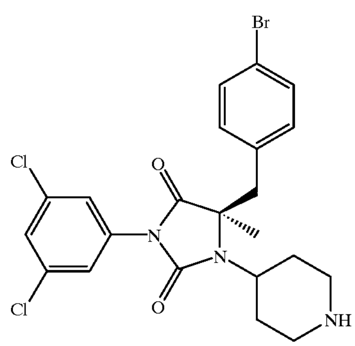 | | 101–3 |
| 225 | 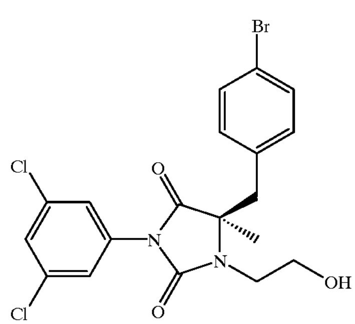 | | 76–7 |

TABLE 15-continued

Examples of Compounds Synthesized by Method O

| EXAMPLE | STRUCTURE | STARTING MATERIAL | MELTING POINT (° C.) |
|---|---|---|---|
| 226 | 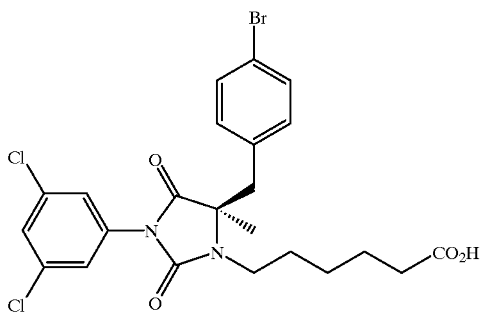 | | 75–7 |
| 227 | 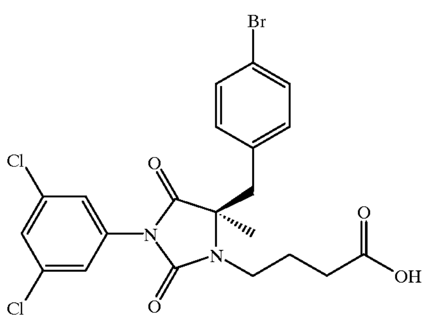 | | 75–7 |
| 228 | 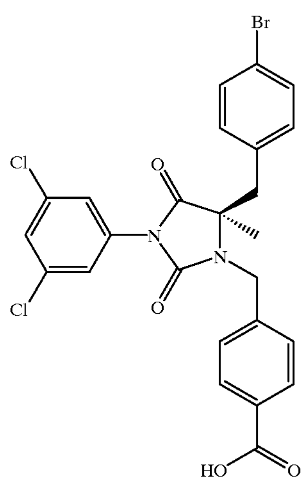 | | 148–9 |

TABLE 15-continued

Examples of Compounds Synthesized by Method O

| EXAMPLE | STRUCTURE | STARTING MATERIAL | MELTING POINT (° C.) |
|---|---|---|---|
| 229 | 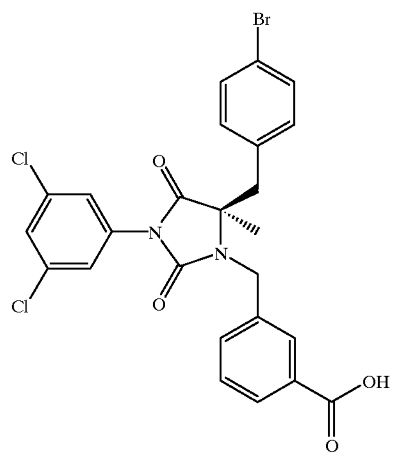 | | 174–5 |
| 230 | 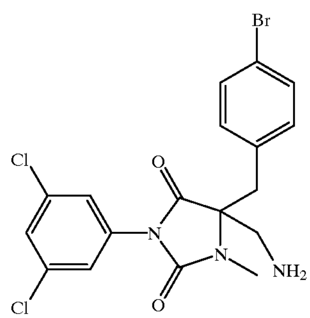 | | 207–8 |
| 231 | 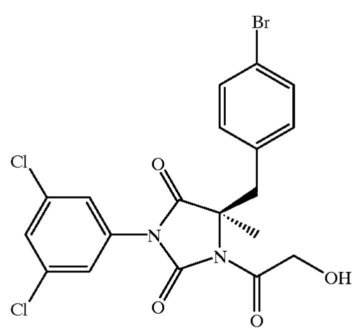 | | 88–9 |

TABLE 15-continued

Examples of Compounds Synthesized by Method O

| EXAMPLE | STRUCTURE | STARTING MATERIAL | MELTING POINT (° C.) |
|---|---|---|---|
| 232 | 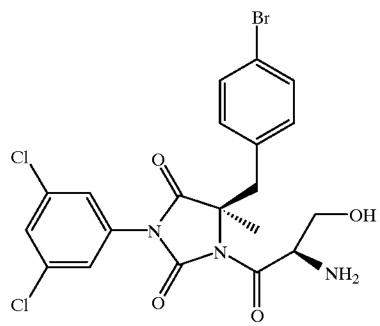 | | 196–7 |
| 233 | 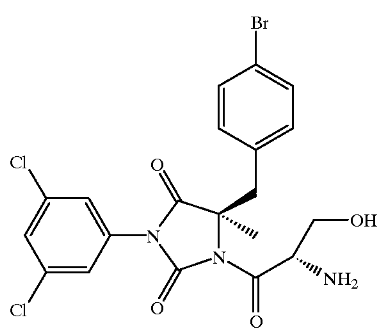 | | 209–10 |
| 234 | 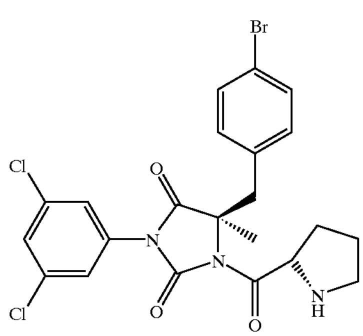 | | 133–4 |

TABLE 15-continued

Examples of Compounds Synthesized by Method O

| EXAMPLE | STRUCTURE | STARTING MATERIAL | MELTING POINT (° C.) |
|---|---|---|---|
| 235 | 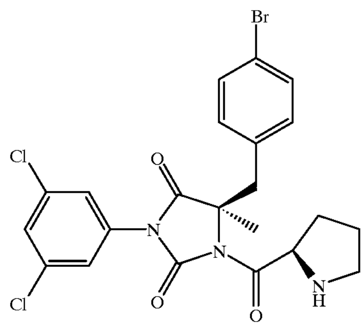 | | 168–70 |
| 236 | 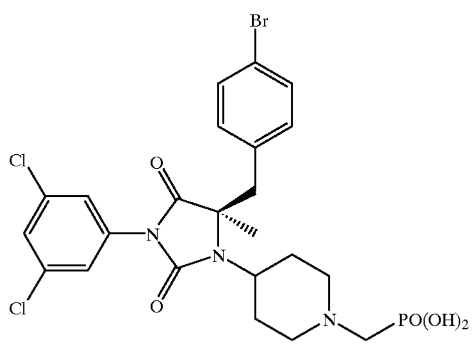 | | oil |
| 237 | 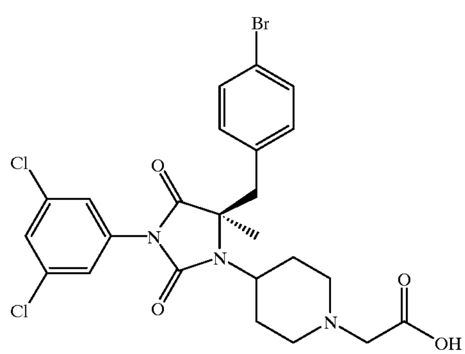 | | not determined |

TABLE 15-continued

Examples of Compounds Synthesized by Method O

| EXAMPLE | STRUCTURE | STARTING MATERIAL | MELTING POINT (° C.) |
|---|---|---|---|
| 238 | (structure with 3,5-dichlorophenyl hydantoin, 4-bromobenzyl, and N-CH₂-O-C(O)-CH(CH₂OH)₂ group) | (structure with 3,5-dichlorophenyl hydantoin, 4-bromobenzyl, and N-CH₂-O-C(O)- linked to 2-phenyl-1,3-dioxane) | 50–4 |

Method O is exemplified by the synthesis of the compound of Example 219, which was carried out as follows: A stirred solution of the starting material (0.10 g, 0.19 mmol) in 10 mL of methylene chloride was chilled to 0° C. before adding 2.0 mL of trifluoroacetic acid. Stirring at 0° C. was continued for 20 min and then the solution was allowed to warm slowly to ambient temperature. The solution was stirred for an additional 6 h at which point it was concentrated yielding an off-white solid which was further dried under vacuum for 16 h. The crude solid was next triturated with 10 mL of boiling hexanes and the mixture was allowed to cool to ambient temperature. The resulting white precipitate was collected via filtration, washed with 5 mL of hexanes and dried under high vacuum for 4 h to afford 0.06 g (68% yield) of the compound from example 219.

Method P. Saponification of Esters to Acids with Hydroxide

Certain compounds having carboxylic esters may be converted to carboxylic acids by treatment with saponifying reagents, in a known per se manner. Generally this involves treating the substrate with NaOH, KOH or LiOH in a solvent such as $H_2O$ sometimes containing a solubilizing agent such as THF. Purification generally involves extracting the unreacted starting material with an organic solvent such as EtOAc or $CH_2Cl_2$, acidification of the aqueous layer and purification of the acid by filtration or extraction into an organic solvent such as EtOAc or $CH_2Cl_2$. Further purification can be performed using recrystallization, silica gel chromatography or reverse-phase HPLC, to afford the desired product.

The compound listed in Table 16 was produced via this general method.

TABLE 16

Examples of Compounds Synthesized by Method P.

| EXAMPLE | STRUCTURE | STARTING MATERIAL | MELTING POINT (° C.) |
|---|---|---|---|
| 239 | (structure with 3,5-dichlorophenyl hydantoin, 4-bromobenzyl, and N-CH₂-(2-HO₂C-phenyl)) | (structure with 3,5-dichlorophenyl hydantoin, 4-bromobenzyl, and N-CH₂-(2-MeO₂C-phenyl)) | 138–40 |

Example 239 (table 16) was prepared by dissolving the starting material (0.38 g, 0.65 mmol) in 4 mL of H2O and 8 mL of MeOH containing LiOH (0.08 g, 1.95 mmol) and heating the mixture at 60° C. for 2.5 h. The MeOH was removed by concentration and the aqueous residue treated with 1 N HCl. The product was extracted into EtOAc from which it crystallized upon cooling. Yield 262 mg (72%).

Method Q. Cleavage of Pthalimide Protecting Group

Primary amines can be protected as their pthalimide derivatives. These derivatives are rapidly synthesized via method U using the potasium salt of pthalimide as the nucleophile. The amine can be liberated from the pthalimide protecting group using nucleophilic reagents such as hydrazine or methyl amine in a solvent such as EtOH. Purification generally involves acidification of the aqueous layer and extracting the unreacted starting material with an organic solvent such as EtOAc or $CH_2Cl_2$ Basification of the aqueous layer produces the free base of the amine which is purified by filtration or extraction into an organic solvent such as EtOAc or $CH_2Cl_2$. Further purification can be performed using recrystallization, silica gel chromatography or reverse-phase HPLC, to afford the desired product.

Compounds listed in Table 17 were produced via this general method.

The compound of Example 240 was prepared by dissolving the starting material (prepare via method U, 0.72 g, 1.2 mmol) in 73 mL of EtOH and treating it with 19.5 mL of a 33% solution of $MeNH_2$ in EtOH. The mixture was heated under reflux for 2.5 h and then cooled to ambient temperature. The reaction mixture was concentrated and the residue was dissolved in $CH_2Cl_2$ which was further washed with $H_2O$ and saturated aqueous NaCl. The organic layer was dried ($Na_2SO_4$) and concentrated. The yellow oil was dissolved in EtOH and treated with HCl gas. The amine hydrochloride of the compound of Example 240 was obtained in 69% yield (0.49g).

Method R. Conversion of Nitriles into Amidines

Aromatic nitrites can be converted into amidine groups by several methods. Generally this conversion requires a two step process wherein the first step involves treatment with acid (such as, for example HCl) and an alcohol (such as, for example MeOH or EtOH) to generate an intermediate imino ether. This derivative is then converted to the amidine via treatment with an amine. Purification is usually by way of recrystallization of a derivative salt of the amidine. Further purification can be performed using recrystallization, silica gel chromatography or reverse-phase HPLC, to afford the desired product.

Compounds listed in Table 18 were produced via this general method.

TABLE 17

Examples of Compounds Synthesized by Method Q.

| EXAMPLE | STRUCTURE | STARTING MATERIAL | MELTING POINT (° C.) |
|---|---|---|---|
| 240 | 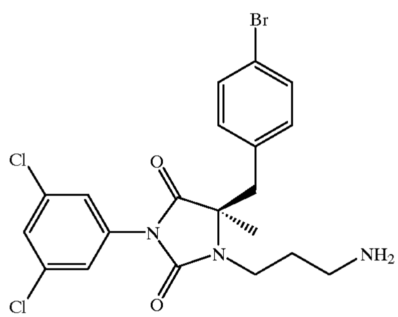 | | 184–5 |
| 241 | 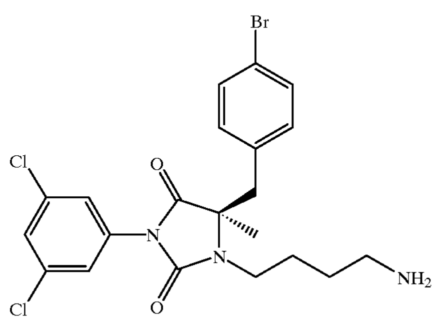 | | 208–9 |

TABLE 18

Examples of Compounds Synthesized by Method R.

| EXAMPLE | STRUCTURE | STARTING MATERIAL | MELTING POINT (° C.) |
|---|---|---|---|
| 242 | [structure] | [structure] | 210–2 |
| 243 | [structure] | [structure] | 180–1 |

The compound of example 243 was prepared by dissolving the starting material (0.2 g, 0.4 mmol) in 7 mL of EtOH, cooling the mixture in an ice bath, and treating the mixture with dry HCl gas for 15 min. The mixture was stirred at room temperature for 1 h and concentrated to yield the crude imino ether hydrochloride. The intermediate was dissolved s in EtOH (10 mL), cooled in an ice bath and treated with anhydrous NH3 gas for 20 min. After 5 h, the reaction mixture was concentrated to provide the crude amidine hydrochloride. This material was purified via silica gel chromatography (1:9 MeOH:CH$_2$Cl$_2$) to yield 0.08 g (38%) of the product.

Method S. Reduction of Carboxylic Acids to Alcohols

Certain compounds having carboxylic acids may be converted to alcohols by treatment with reducing reagents, in a known per se manner. Generally this involves treating the substrate with LiAlH$_4$ or a BH$_3$-based reagent in a solvent such as THF or ether. After careful quenching with an aqueous system, purification generally involves extracting the product into organic solvent such as EtOAc or CH$_2$Cl$_2$ and purification using recrystallization, silica gel chromatography or reverse-phase HPLC, to afford the desired product.

The compounds listed in Table 19 was produced via this general method.

TABLE 19

Examples of Compound Synthesized by Method S.

| EXAMPLE | STRUCTURE | STARTING MATERIAL | MELTING POINT (° C.) |
|---|---|---|---|
| 244 | [structure] | [structure] | 172–3 |

The compound of example 244 was prepared by dissolving the starting material (prepare via methods J and O, 0.16 g, 0.32 mmol) in 1 mL of THF, cooling the mixture in an ice bath and treating it with 0.65 mL of a 1 M BH$_3$-THF solution (0.65 mmol). The mixture was allowed to warm to ambient temperature and stir for 15 h. The reaction mixture was quenched by the slow and careful addition of water and the organic components were extracted into EtOAc. The EtOAc layer was washed with water, saturated aqueous NaCl and dried over Na$_2$SO$_4$. Concentration and silica gel chromatography (1:1 EtOAc:Hexanes) produced the desired compound (0.06 g, 42%).

Method T. Deprotection of Compounds with Nucleophilic Reagents

Certain compounds having methoxy protecting groups may be deprotected to the hydroxy derivative by treatment with certain nucleophilic reagents, in a known per se manner. Generally this involves treating the substrate with BBr$_3$ or TMSI in a solvent such as CH$_2$Cl$_2$, generally cooled in an ice bath and followed with or without heating. After between about 10 min and 8 h the reaction is quenched with a weak base such as aqueous NaHCO$_3$ and the organic component extracted into a solvent such as EtOAc and purified after concentration, as by silica gel chromatography or recrystallization, to afford the desired product.

Compounds listed in Table 20 were produced via this general method.

TABLE 20

Examples of Compounds Synthesized by Method T.

| EXAMPLE | STRUCTURE | STARTING MATERIAL | MELTING POINT (° C.) |
|---|---|---|---|
| 245 | 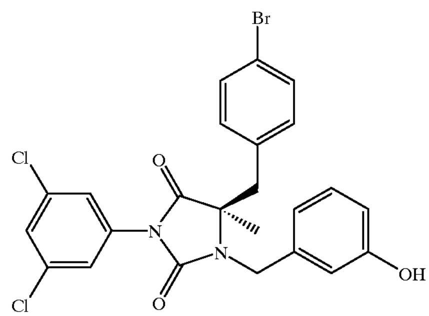 | | 94–7 |
| 246 | 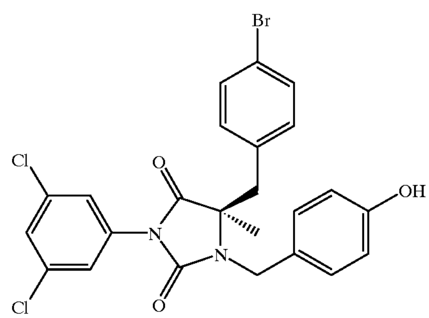 | | 118–120 |
| 247 | 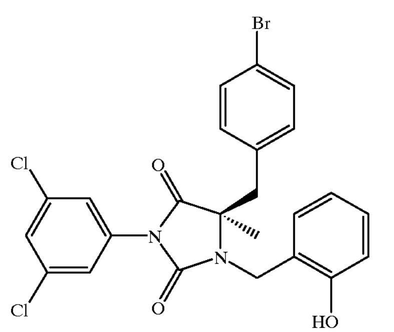 | | 94–96 |

TABLE 20-continued

Examples of Compounds Synthesized by Method T.

| EXAMPLE | STRUCTURE | STARTING MATERIAL | MELTING POINT (° C.) |
|---|---|---|---|
| 248 | 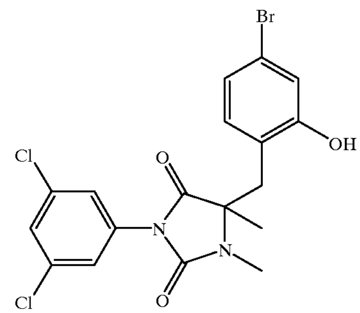 | | not determined |

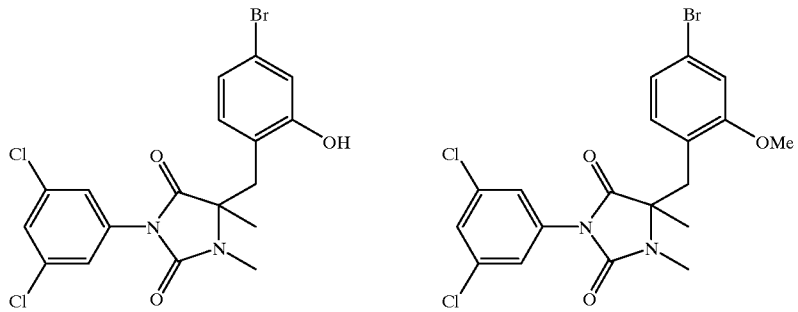

Method T is exemplified by the synthesis of the compound of Example 246, which was carried out as follows: A stirred solution of the starting material (0.35 g, 0.64 mmol) in 9 mL of $CH_2Cl_2$ was chilled to 0° C. before adding 1.0 mL of $BBr_3$ (1.07 mmol, 1 M $CH_2Cl_2$). Stirring was continued and then the solution was allowed to warm slowly to ambient temperature. The solution was stirred for an additional 4 h at which point it saturated aqueous $NaHCO_3$ was added, the organic layer was removed and concentrated yielding the crude product. Purification was performed by silica gel chromatography (1:4 EtOAc: Hexanes) yielding 0.16 g (48% yield) of the desired compound.

Method U. Nucleophilic Displacement.

An appropriate electrophilic agent is dissolved in an aprotic solvent (such as DMF, THF or DMSO) and treated with one to three equivalents of a nucleophile (such as $Me_3N$, Na salt of imidazole, $Na2SO_3$, NaCN, $P(OEt)_3$, or the K salt of Pthalimide at between about room temperature and 100° C. The mixture stirred at between about 0 and 100° C. for up to about 24 h. (Progress of the reaction can be monitored using TLC). The solution is then cooled and diluted with an organic solvent (such as, for example, EtOAc). The organic phase is washed sequentially with dilute aqueous acid (such as 1 N HCl), and with water, dried (for example, over $MgSO_4$) and concentrated. The desired compound is purified, as by silica gel chromatography, reverse-phase HPLC or by recrystallization.

Compounds listed in Table 21 were produced via this general method.

TABLE 21

Examples of Compounds Synthesized by Method U.

| EX. | STRUCTURE | STARTING ELECTROPHILE | STARTING NUCLEOPHILE | M.P. (° C.) |
|---|---|---|---|---|
| 249 | 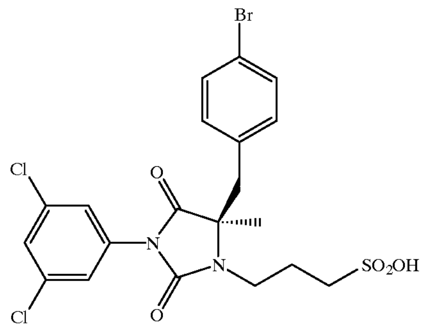 | | $Na_2SO_3$ | 200–2 |
| 250 | 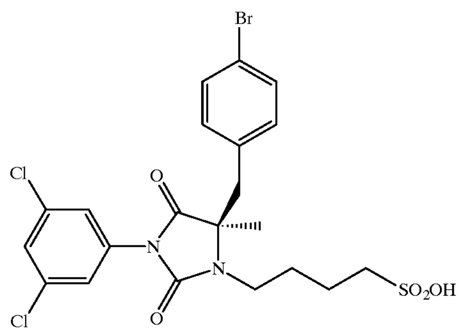 | | $Na_2SO_3$ | 193–4 |

TABLE 21-continued

Examples of Compounds Synthesized by Method U.

| EX. | STRUCTURE | STARTING ELECTROPHILE | STARTING NUCLEOPHILE | M.P. (° C.) |
|---|---|---|---|---|
| 251 | 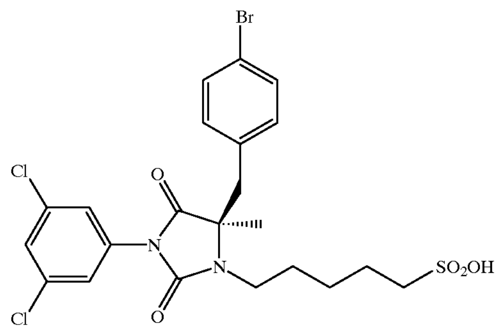 | | Na₂SO₃ | >260 |
| 252 | 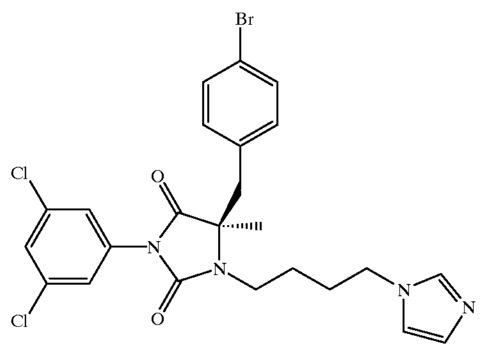 | | imidazole-Na | 195–6 |

TABLE 21-continued

Examples of Compounds Synthesized by Method U.

| EX. | STRUCTURE | STARTING ELECTROPHILE | STARTING NUCLEOPHILE | M.P. (° C.) |
|---|---|---|---|---|
| 253 | 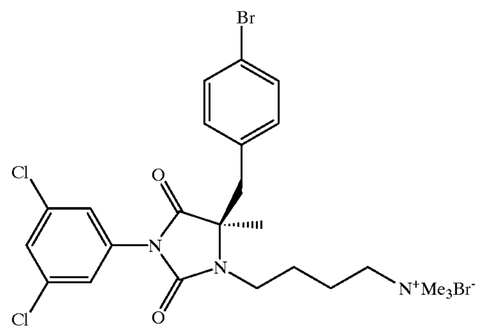 | | Me₃N | 55–6 |
| 254 | 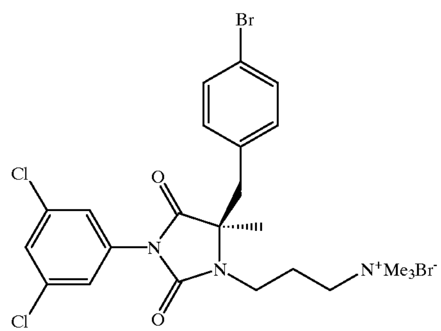 | | Me₃N | 54(d) |

TABLE 21-continued

Examples of Compounds Synthesized by Method U.

| EX. | STRUCTURE | STARTING ELECTROPHILE | STARTING NUCLEOPHILE | M.P. (° C.) |
|---|---|---|---|---|
| 255 | 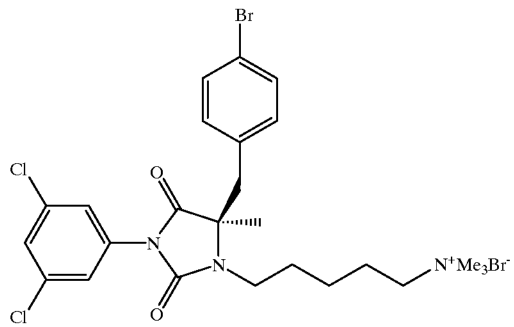 | | Me₃N | 42–3 |
| 256 | 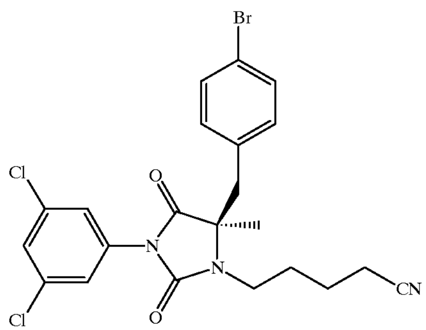 | | NaCN | 152–3 |

TABLE 21-continued

Examples of Compounds Synthesized by Method U.

| EX. | STRUCTURE | STARTING ELECTROPHILE | STARTING NUCLEOPHILE | M.P. (° C.) |
|---|---|---|---|---|
| 257 | 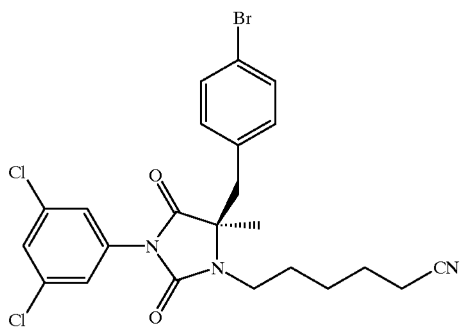 | | NaCN | 149–50 |
| 258 | 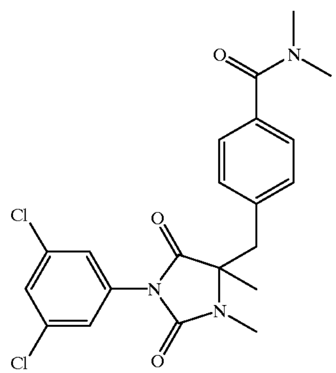 | | (CH$_3$)$_2$NH | 68–70 |

TABLE 21-continued

Examples of Compounds Synthesized by Method U.

| EX. | STRUCTURE | STARTING ELECTROPHILE | STARTING NUCLEOPHILE | M.P. (° C.) |
|---|---|---|---|---|
| 259 | 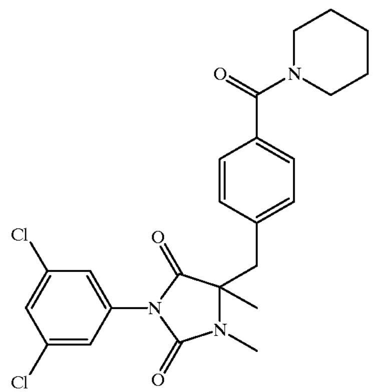 | | | 65–6 |
| 260 | 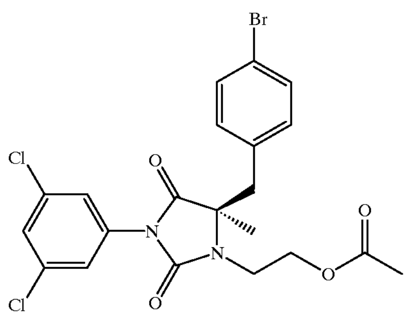 | $CH_3COCl$ | | oil |

TABLE 21-continued

Examples of Compounds Synthesized by Method U.

| EX. | STRUCTURE | STARTING ELECTROPHILE | STARTING NUCLEOPHILE | M.P. (° C.) |
|---|---|---|---|---|
| 261 | 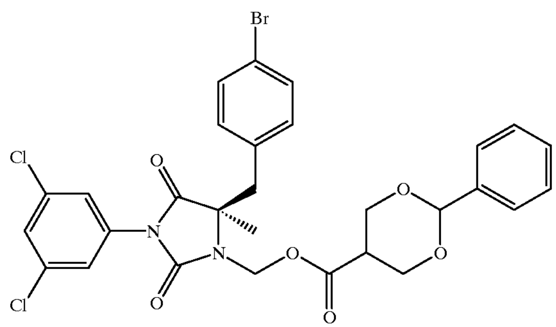 | | | not determined |
| 262 | 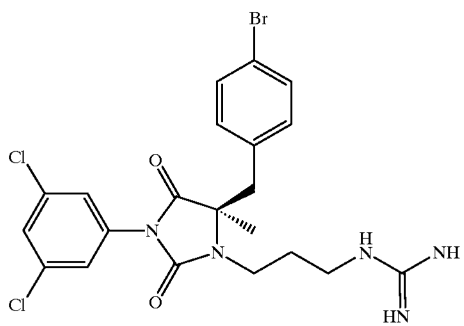 | | | 188–90 |

TABLE 21-continued

Examples of Compounds Synthesized by Method U.

| EX. | STRUCTURE | STARTING ELECTROPHILE | STARTING NUCLEOPHILE | M.P. (° C.) |
|---|---|---|---|---|
| 263 | 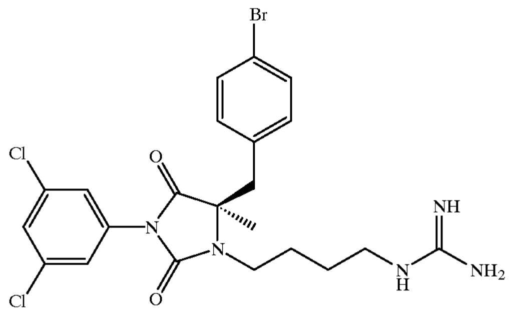 | | | 118–21 |
| 264 | 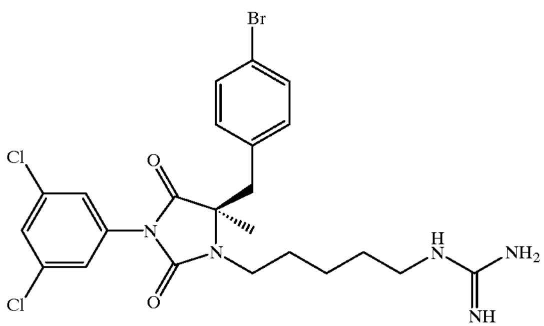 | | | 113–5 |

Method U is exemplified by the synthesis of the compound of Example 262, which was carried out as follows: To the starting material (0.28 g, 0.54 mmol) was added 1-H-pyrazolecarboxamidine (0.08 g, 0.54 mmol) followed by 7 mL of DMF and 0.2 mL of N,N-diisopropyl-ethylamine. The resulting mixture was then stirred 15 h at room temperature. Next was added ether which caused the mixture to become turbid. As no crystals were forming, MeOH was added to re-dissolve the reaction components and the product was precipitated as its HCl salt by the addition of 1 N HCl. The solid was collected and washed with ether to yield 0.11 g (20%) of the guanidine hydrochloride.

Method V. Resolution of a Mixture of Enantiomers.

There are several ways to resolve the compounds of the invention into their enantiomerically pure forms. One such method is chiral HPLC. An exemplary column packing is Chiracel-OD (Diacel Chemistry Industries). An exemplary solvent system is 9:1 hexanes: iso-propyl alcohol. In general, the R-enantiomer is eluted first, but this should not be used as the sole criterion for the assignment of stereochemistry.

The compounds listed in Table 22 were resolved via this method.

TABLE 22

Examples of Compounds Obtained by Method V.

| EXAMPLE | STRUCTURE | STARTING RACEMATE | MELTING POINT (° C.) |
| --- | --- | --- | --- |
| 265 | 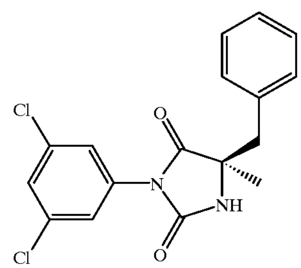 | | not determined |
| 266 | 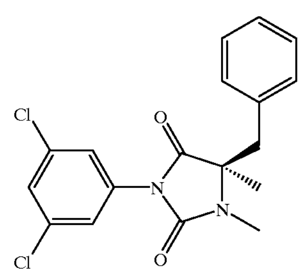 | | not determined |
| 267 | 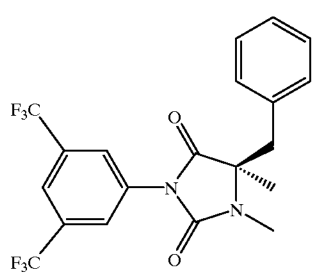 | | oil |
| 268 | 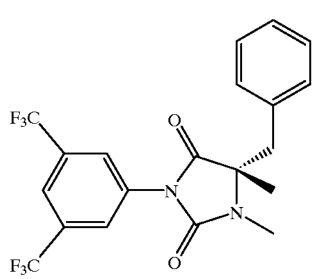 | | oil |

TABLE 22-continued

Examples of Compounds Obtained by Method V.

| EXAMPLE | STRUCTURE | STARTING RACEMATE | MELTING POINT (° C.) |
|---|---|---|---|
| 269 | 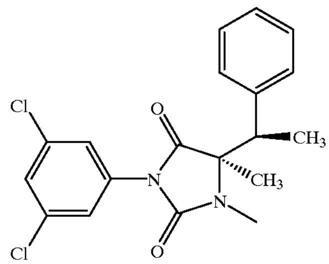 | (Racemic) | oil |
| 270 | 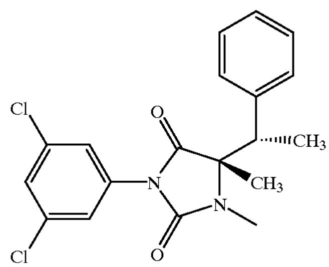 | (Racemic) | oil |
| 271 | 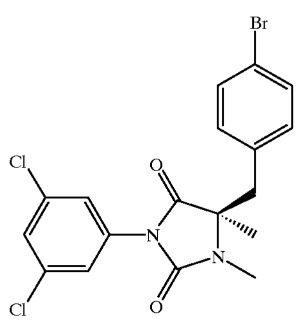 | | 52–54 |
| 272 | 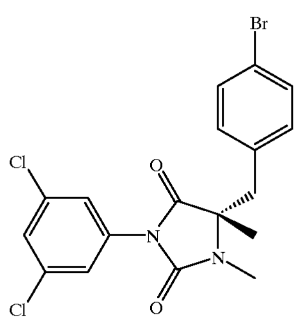 | | 136–7 |

TABLE 22-continued

Examples of Compounds Obtained by Method V.

| EXAMPLE | STRUCTURE | STARTING RACEMATE | MELTING POINT (° C.) |
|---|---|---|---|
| 273 | 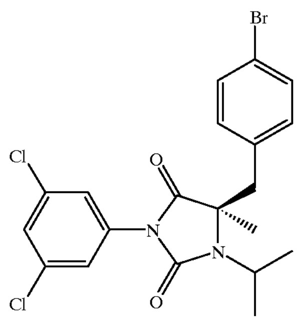 | | not determined |
| 274 | 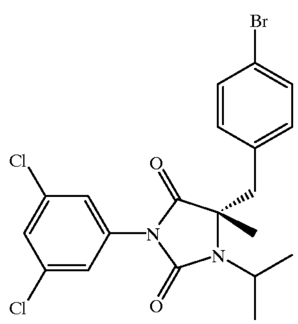 | | not determined |
| 275 | 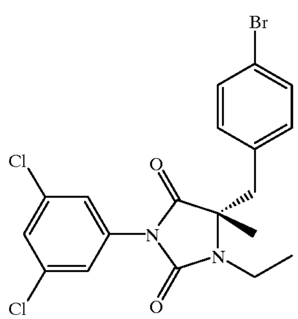 | | oil |
| 276 | 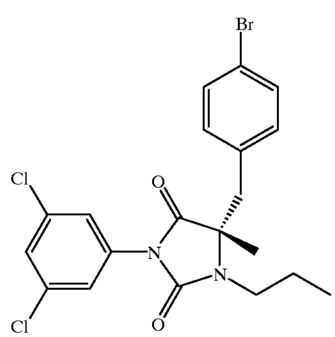 | | oil |

TABLE 22-continued

Examples of Compounds Obtained by Method V.

| EXAMPLE | STRUCTURE | STARTING RACEMATE | MELTING POINT (° C.) |
|---|---|---|---|
| 277 | 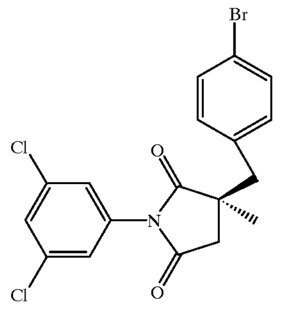 | | not determined |
| 278 | 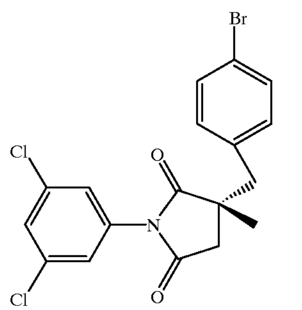 | | not determined |

Description of Biological Properties

The biological properties of representative compounds of the formula I were investigated by way of the experimental protocols described below. The results of such testing are reported in Table 23, which appears below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol: LFA-1 is immunopurified using the TS2/4 antibody from a 20 g pellet of human JY or SKW3 cells, utilizing a protocol previously described (Dustin, M. J.; et al., *J. Immunol.* 1992, 148, 2654–2660). The LFA-1 is purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature*, 1990, 344, 70–72 and see Arruda, A.; et al., *Antimicrob. Agents Chemother.* 1992, 36, 1186–1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 μg/mL in Dulbecco's phosphate buffered saline with calcium and magnesium, additional 2 mM $MgCl_2$ and 0.1 mM PMSF (Diluting Buffer) in a 96-well plate for 30 amin at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37 ° C. , wells are washed as above and the substrate for the horse radish peroxidase is added to each well to develop a quantitative colorimetric signal proportional to the amount of LFA-1 bound to sICAM-1. Soluble ICAM-1 (60 μg/mL) is used as a positive control for inhibition of the LFA-1/ICAM-1 interaction. The lack of the addition of LFA-1 to the binding assay is used as a background control for all samples. A dose-response curve is obtained for all test compounds.

Results of these tests are reported as $K_d$'s in $\mu M$.

MMT Assay to Determine Cytotoxicity

Purpose of Assay:

In order to obtain meaningful data from cellular assays, compounds must first be first tested in an assay to measure cellular toxicity. The MTT assay can be used for this purpose.

Description of Assay Protocol:

MTT, (3-(4,5-dimethylthiazol-2-yl)-2,5-diphenyl-2H-tetrazolium bromide), is a yellow substrate that is cleaved by cells with active mitochondria to yield a dark blue/purple formazan product. This precipitate can be solublized and the amount of material quantitatified via spectrophotometric procedures (Gerlier, D.; Thomasset, N. *J. Immunol. Methods*, 1986, 94, 57–63). The amount of color is proportional to the number of viable cells. This assay system is used to assess the effect of test compounds on cell viability in vitro.

SKW3 cells, which express LFA-1, are used. Cells used in each assay were adjusted to 1.25×106 cells/mL and 100 $\mu L$ of this stock is dispersed into each well of a 96 well, flat bottom microtiter plate. For each condition in a particular experiment, triplicate wells are set up. Serial dilutions of each test compound or vehicle alone are added to each well. Cells are incubated with compound for 4–24 h at 37° C. before cell viability is assessed. Next, 10 $\mu L$ of filter sterilized MTT is added to each well. The MTT stock is made in phosphate buffered saline at a concentration of 5 mg/mL. Plates are then incubated for 1 h at 37° C., 5% $CO_2$ atmosphere. Periodically, the plates are examined for formazan crystal development.

At the end of the incubation period, formazan crystals are dissolved by the addition of 100 $\mu L$ of 0.04 N HCl in iso-propyl alcohol to each well. Each well is thoroughly mixed by repeated pipetting with a multichannel pipetter. The plates are allowed to sit at room temperature for 15–20 minutes and are then read with a spectrophotometer. Absorbance is measured at the test wavelength of 570 nm. Data are reported as the concentration range (in $\mu M$) wherein 50% of the cells are no longer viable.

Assay to Determine Inhibition of SKW3 cell binding to ICAM-1 vs. Binding to Fibronectin Purpose of Assay:

This assay is used to test the selective ability of a test compound to antagonize the interaction of a cell bound form of LFA-1 with ICAM-1. The assay uses a human T cell line, SKW3 cells which express CD18, CD11a and other integrins not related to CD18, CD11a and which can be "activated" by phorbol esters. Phorbol esters enhance the affinity of CD18, CD11a for ICAM-1.

This same lymphocyte line, SKW3, also adheres to fibronectin in the presence of phorbol esters. This adhesion is mediated by membrane proteins independent of the LFA-1/ICAM-1 interaction. The SKW3 cells express another integrin, VLA4, which is the receptor for fibronectin. Therefore, as a preliminary indication of the selectivity of a test compounds to interfere with Leukointegrin/CAM interactions but not other integrin-ligand binding events, a compound can be tested for its ability to antagonize cell bound fibronectin receptor in its interaction with purified fibronectin. Compounds that inhibit this fibronectin adhesion are not specific antagonists of the CD18, CD11a/ICAM-1 binding.

Description of Assay Protocol:

Ninety-six well plates are coated with either sICAM-1(40 $\mu g/mL$) or fibronectin (100 $\mu g/mL$) in Diluting buffer for 1 h at room temperature. Added to the wells are 100 $\mu L$ of the appropriately diluted test compound or 100 $\mu L$ of RPMI with 15% fetal bovine serum as a control. SKW3 cells, which express CD18, CD11a and VLA4 (Dustin, M.; et al., *J. Exp. Med.* 1987, 165, 672–692) are washed and suspended to a concentration of $10^6$ cells/mL in RPMI with 15% fetal bovine serum. Immediately before adding the cells to the wells, cells are stimulated with the phorbol ester 12-myristate 13-acetate (PMA) for a final concentration of 100 $\mu g/mL$. 100 $\mu L$ of cells are then added to the wells resulting in a final concentration of 50 $\mu g/mL$ PMA and 2 cells/well. The plates are incubated for 2 h at 37° C. Unbound or loosely bound cells are gently washed away with RPMI. Cells remaining and hence bound to ICAM-1 or to fibronectin are quantitated by the same reagent used above for the MTT experiment.

Data are reported as the concentration or concentration range (in $\mu M$) at which 50% of binding is inhibited.

Compounds Inhibit JY Cell Aggregation

Purpose of Assay:

This is an in vitro cell to cell adhesion assay which can be used to test the ability of a test compound to directly inhibit LFA-1 dependent aggregation at the cellular level.

Many Epstein-Barr virus-transformed cells exhibit aggregation. This aggregation can be enhanced by the addition of phorbol esters. Such homotypic aggregation (i.e., aggregation involving only one cell type) was found to be blocked by anti-LFA-1 antibodies (Rothlein, R. R.; et al., *J. Exp. Med.* 1986, 163, 1132–1149). Thus, the extent of LFA-1-dependent binding may be determined by assessing the extent of spontaneous or phorbol ester-dependent aggregate formation.

An agent which interferes with LFA-1 -dependent aggregation can be identified through the use of an assay capable of determining whether the agent interferes with either spontaneous, or phorbol ester-dependent aggregation of Epstein-Barr virus transformed cells. It is preferable to employ cells of the JY cell line (Terhost, L; et aL, *Proc. Natl. Acad. Sci.* USA, 1976, 73, 910) for the homotypic aggregation assay. This assay, capable of measuring LFA-1 dependent aggregation, may be employed to identify agents which act as antagonists to the LFA-1 dependent aggregation. Such agents may act by impairing the ability of either LFA-1 or ICAM-1 to mediate aggregation. Thus, agents may be examined to directly determine if they are antagonists of LFA-1 aggregation.

Description of Assay Protocol:

JY cells are cultured in RPMI 1640 culture medium supplemented with 10% fetal calf serum and 50 $\mu g/mL$ gentamycin. The cells are cultured at 37° C. in an atmosphere of 5% $CO_2$ at a relative humidity of 95%. JY cells used in this assay are washed two times with RPMI 1640 medium containing 5 mM HEPES buffer and resuspended to a concentration of $2\times10^6$ cells/mL. Added to flat-bottomed, 96-well microtiter plates are 50 $\mu L$ of test compound diluted in complete medium, 50 $\mu L$ of complete medium with or without purified monoclonal antibodies (negative and positive controls for inhibition, respectively), 50 $\mu L$ of complete medium containing 200 ng/mL of the phorbol ester phorbol myristate acetate (PMA) and 100 $\mu L$ of cells at a concentration of $2\times10^6$ cells/mL in complete medium. This yields a final concentration of 50 ng/nL PMA and $2\times10^5$ cells/well. Cells are allowed to settle spontaneously, and the degree of aggregation is scored at various time points. Scores range from 0 to 4 where 0 indicates that essentially no cells are in clusters; 1 indicates that <25% of the cells are in clusters; 2 indicates that <50% of the cells are in clusters; 3 indicates that <75% of the cells are in clusters and 4 indicates that 100% of the cells are aggregated. This procedure has been described by Rothlein, R. R.; et al., *J. Exp. Med.* 1986, 163, 1132–1149. This paper also reported that antibody to LFA-1 is capable of inhibiting the formation of aggregates. Whereas 100% of the cells form aggregates in the absence of LFA-1 antibody, less than 20% of the cells were found to be in aggregates when anti-LFA-1 antibody was added in the same paper.

Data are reported as the concentration or concentration range (in $\mu$M) at which 50% of binding is inhibited.

Assay to Determine Inhibition the Mixed Lymphocyte Reaction

Purpose of Assay:

As discussed above, ICAM-1 is necessary for effective cellular interactions during an immune response mediated through LFA-1-dependent cell adhesion. When lymphocytes from two unrelated individuals are cultured together, blast transformation and cell proliferation of the lymphocytes are observed. This response is known as a mixed lymphocyte reaction (MLR) and is analogous to the response of lymphocytes to the 10 addition of antigens or mitogens (Immunology: *The Science of Self-Nonself Discrimination*; Klein, J., Ed.; John Wiley & Sons: NY, 1982, pp 453–458). Monoclonal antibodies directed against ICAM-1 and LFA-1 were used as controls to demonstrate inhibition of cell adhesion-dependent lymphocyte stimulation and proliferation.

This assay protocol is used to to determine the effect of a test compound on the human MLR. The ability of a test compound to inhibit the MLR and antigen-specific mononuclear cell responses shows that it has therapeutic utility in acute graft rejection., as well as in related immune mediated disorders dependent on CD18, CD11a/ICAM interactions.

Description of Assay Protocol:

Peripheral blood is obtained from normal, healthy donors by venipuncture. The blood is collected in heparinized tubes and diluted 1:1 at room temperature with Puck's G (GIBCO) balanced salt solution (BSS). The blood mixture (20 mL) is layered over 15 mL of a Ficoll/Hypaque density gradient (Pharmacia, density=1.078, room temperature) and centrifuged at 1000×g for 20 minutes. The interface is then collected and washed 3 times in Puck's G. The cells are counted on a hemocytometer and resuspended in RPMI 1640 culture medium (GIBCO) containing 0.5% of gentamicin, 1 mM L-glutamine (GICO) and 5% heat inactivated (56° C., 30 min) human AB sera (Flow Laboratories) (hereafter referred to as RPMI-culture medium).

Peripheral blood mononuclear cells (PBMC) are cultured in medium at $6.25 \times 10^5$ cells/mL in a Linbro round-bottomed microtiter plate. Stimulator cells (cells that have been treated with irradiation so that they are unable to proliferate) from a separate donor are cultured with the responder cells at the same concentration. Test compound is added to wells at various concentrations. The total volume per culture is 0.2 mL. Controls include compound vehicle alone (DMSO), responder cells alone, and stimulator cells alone. The culture plates are incubated at 37° C. in a 5% $CO_2$-humidified air atmosphere for 5 days.

The wells are pulsed with 0.5 $\mu$Ci of tritiated thymidine ($^3$HT) (New England Nuclear) for the last 18 h of culture. In some cases a two-way MLR can be performed. The protocol is the same except that the second donor's cells are not inactivated by irradiation.

The cells are harvested onto glass fiber filters using an automated multiple sample harvester (Skatron, Norway), and rinsed with water and methanol. The filters are oven dried and counted in Aquasol in a Beckman (LS-3801) liquid scintillation counter.

Data are reported as "+" or "−" at a given concentration (in $\mu$M).

In vivo: Allogeneic Cell Transplant Model

Purpose of Assay:

The ability of cells to recognize other cells from self or from another genetically different individual (non-self) is an important property in maintaining the integrity of tissue and organ structure. The allogeneic cell transplant response is an important model for studies of transplant rejection and immunocompetence. This T-cell-mediated immune response can be induced in adult mice by the injection of lymphocytes from a histoincompatible mouse strain into the footpad. This response is characterized by T-cell proliferation which is limited to the popliteal lymph node that receives drainage from the injected footpad area. No in vitro system can completely duplicate this in vivo response. Thus, this animal model can be used to assess the ability of a test compound to suppress transplant rejection.

Description of Assay Protocol:

Experiments are conducted using male or female mice (20–26 grams). Any histoincompatible mouse strains suffice for donor and recipient populations. Typically DBA mice are used as donors and C57 1/6 mice are used as recipients. A minimum of 1 week stabilization and conditioning period is required before use during which time the animals are maintained in accordance with the Animal Resource Center S.O.P. Each study utilizes 36 recipient mice divided into groups of 6. The tests last approximately four days. Donor mice are sacrificed by $CO_2$ asphyxiation and spleens are removed and made into a cell suspension. The cells ($1.0 \times 10^7$/metatarsal in 0.05 mL) are injected intra dermal (according to standard protocol) into the dorsal metatarsal skin of recipient mice. Four days later, the animals are sacrificed by $CO_2$ asphyxiation and the popliteal nodes are removed and weighed. Groups of mice receiving putative immunosuppressive agents are dosed subcutaneously, intraperitoneally or orally one hour prior to cell injection and daily thereafter according to standard protocol. Student's T-test was used to determine significant differences between popliteal lymph nodes of groups of untreated mice and those mice treated with putative immunosuppressive agents (see: Kroczek, R. A.; Black, C. D. V.; Barbet, J.; Shevach, E. M., *J. Immunology*, 1987, 139, 3597).

Data are reported as the dose at which 50% inhibition is observed and the manner in which the compound was administered. In Table 23, the following legends are applicable: [a]nd=not determined. [b]percent inhibition at 160 $\mu$g/mL. [c]no inhibition observed up to highest dose. Exact quantification not always possible due to intrinsic toxicity of compound (see MTT result). [d]percent inhibition (concentration in $\mu$M ). [e]approximated from incomplete dose-response curve. [f]not determined; compound is a synthesis intermediate.

TABLE 23

Results of Biological Testing.[a]

| Cmpd. Of Ex. | LFA-1/ICAM Binding Assay $K_d$ ($\mu M$) | Cellular Toxicity Assay MTT $LD_{50}$ ($\mu M$) | Assay to Detect SKW3 Cells Binding to: ICAM $IC_{50}$ ($\mu M$) | Assay to Detect SKW3 Cells Binding to: FIBRONECTIN $IC_{50}$ ($\mu M$) | JY Cell Aggregation Assay JY Cell IC50 ($\mu M$) | Mixed Lymphocyte Reaction MLR +/− ($\mu M$) | Allogeneic Cell Transplatation Assay ACT $ED_{50}$ (mg/kg) |
|---|---|---|---|---|---|---|---|
| 1 | 1.64 | nd | nd | nd | nd | nd | nd |
| 2 | 14.4 | 125–250 | >100[c] | >100[c] | nd | nd | nd |
| 3 | 3.00 | 125–250 | nd | nd | nd | nd | nd |
| 4 | 9.32 | 250–500 | nd | nd | nd | nd | nd |
| 5 | 15.4 | 250–500 | nd | nd | nd | nd | nd |
| 6 | 12.8 | 250–500 | nd | nd | nd | nd | nd |
| 7 | 1.33 | 250–500 | 50–100 | No inh[c] | nd | nd | nd |
| 8 | 2.86 | 125–250 | nd | nd | nd | nd | nd |
| 9 | 7.87 | 250–500 | nd | nd | nd | nd | nd |
| 10 | 0.19 | >500 | 50 | No inh[c] | 6.3 | nd | nd |
| 11 | 6.30 | nd | nd | nd | nd | nd | nd |
| 12 | 1.75 | 125–250 | nd | nd | nd | nd | nd |
| 13 | 1.96 | nd | nd | nd | nd | nd | nd |
| 14 | 12.7 | 125–250 | 63–125 | >125[c] | nd | nd | nd |
| 15 | 2.3 | 125–250 | 31–63 | No Inh[c] | 25–50 | — | nd |
| 16 | 0.85 | 63–125 | 19–38 | >75[c] | nd | nd | nd |
| 17 | 3.01 | 125 | >63[c] | No inh[c] | nd | nd | nd |
| 18 | 0.76 | 125–250 | 32–63 | >125[c] | 6 | — | nd |
| 19 | 0.76 | nd | nd | nd | nd | nd | nd |
| 20 | 1.76 | 125–250 | 16 | 63–125 | nd | nd | nd |
| 21 | 0.69 | 125–250 | <16 | 125–250 | nd | — | nd |
| 22 | 0.40 | 125–250 | <16 | No inh[c] | nd | — | nd |
| 23 | 0.77 | 50–100 | 25–50 | >100[c] | 13 | nd | nd |
| 24 | 0.85 | >400 | >60 | No inh[c] | nd | nd | nd |
| 25 | 3.08 | nd | nd | nd | nd | nd | nd |
| 26 | 2.75 | nd | nd | nd | nd | nd | nd |
| 27 | 52[e] | nd | nd | nd | nd | nd | nd |
| 28 | 2.59 | 100–200 | 100–200[c] | No inh[c] | nd | nd | nd |
| 29 | 0.06 | 63–125 | 8 | No inh[c] | 0.1 | +(50) | ~60 (per os) |
| 30 | 1.48 | nd | nd | nd | nd | nd | nd |
| 31 | 1.36 | nd | nd | nd | nd | nd | nd |
| 32 | 12.1 | nd | nd | nd | nd | nd | nd |
| 33 | 0.94 | nd | nd | nd | nd | nd | nd |
| 34 | 0.13 | 200–400 | 6 | No inh[c] | 1.8 | nd | nd |
| 35 | 0.10 | 38–46 | 5–10 | No inh[c] | 0.8 | nd | nd |
| 36 | 4.05 | nd | nd | nd | nd | nd | nd |
| 37 | 0.16 | <13 | 5–10 | >19 | 1.6 | nd | nd |
| 38 | 1.15 | nd | nd | nd | nd | nd | nd |
| 39 | 0.18 | nd | nd | nd | nd | nd | nd |
| 40 | 0.48 | 50–100 | 50–100 | 50–100 | 25 | nd | nd |
| 41 | 0.16 | nd | nd | nd | nd | nd | nd |
| 42 | 0.60 | nd | nd | nd | nd | nd | nd |
| 43 | 0.17 | 25–50 | 3–6 | No inh[c] | 1.8 | nd | nd |
| 44 | 0.42 | 63–125 | 6–12 | No inh[c] | 0.3 | nd | nd |
| 45 | nd[f] | nd | nd | nd | nd | nd | nd |
| 46 | 2.26 | nd | nd | nd | nd | nd | nd |
| 47 | 4.31 | nd | nd | nd | nd | nd | nd |
| 48 | 1.75 | nd | nd | nd | nd | nd | nd |
| 49 | 0.26 | nd | nd | nd | nd | nd | nd |
| 50 | 17[e] | nd | nd | nd | nd | nd | nd |
| 51 | 0.43 | nd | nd | nd | nd | nd | nd |
| 52 | 1.59 | nd | nd | nd | nd | nd | nd |
| 53 | 1.47 | nd | nd | nd | nd | nd | nd |
| 54 | 0.42 | nd | nd | nd | nd | nd | nd |
| 55 | 0.20 | nd | nd | nd | nd | nd | nd |
| 56 | 0.48 | nd | nd | nd | nd | nd | nd |
| 57 | 0.36 | nd | nd | nd | nd | nd | nd |
| 58 | 2.85 | nd | nd | nd | nd | nd | nd |
| 59 | 0.33 | nd | nd | nd | nd | nd | nd |
| 60 | 0.23 | nd | nd | nd | nd | nd | nd |
| 61 | 2.35 | nd | nd | nd | nd | nd | nd |
| 62 | 0.16 | nd | nd | nd | nd | nd | nd |
| 63 | 3[e] | nd | nd | nd | nd | nd | nd |
| 64 | 1.45 | nd | nd | nd | nd | nd | nd |
| 65 | 1.32 | nd | nd | nd | nd | nd | nd |
| 66 | 2.85 | nd | nd | nd | nd | nd | nd |
| 67 | 3.54 | nd | nd | nd | nd | nd | nd |
| 68 | 2.58 | nd | nd | nd | nd | nd | nd |
| 69 | 70[e] | nd | nd | nd | nd | nd | nd |
| 70 | 1.89 | nd | nd | nd | nd | nd | nd |

TABLE 23-continued

Results of Biological Testing.[a]

| Cmpd. Of Ex. | LFA-1/ICAM Binding Assay $K_d$ ($\mu M$) | Cellular Toxicity Assay MTT $LD_{50}$ ($\mu M$) | Assay to Detect SKW3 Cells Binding to: ICAM $IC_{50}$ ($\mu M$) | FIBRONECTIN $IC_{50}$ ($\mu M$) | JY Cell Aggregation Assay JY Cell IC50 ($\mu M$) | Mixed Lymphocyte Reaction MLR +/− ($\mu M$) | Allogeneic Cell Transplantation Assay ACT $ED_{50}$ (mg/kg) |
|---|---|---|---|---|---|---|---|
| 71 | 4.38 | nd | nd | nd | nd | nd | nd |
| 72 | 0.06 | >363 | 20–40 | No inh[c] | 1.4 | +(25) | nd |
| 73 | 0.34 | nd | nd | nd | nd | nd | nd |
| 74 | 0.67 | nd | nd | nd | nd | nd | nd |
| 75 | 0.29 | nd | nd | nd | nd | nd | nd |
| 76 | 2.34 | >500 | 150–300 | >300[c] | nd | nd | nd |
| 77 | nd[f] | nd | nd | nd | nd | nd | nd |
| 78 | 0.34 | nd | nd | nd | nd | nd | nd |
| 79 | 0.43 | nd | nd | nd | nd | nd | nd |
| 80 | 0.19 | >400 | 5 | No inh[c] | 3.2 | nd | nd |
| 81 | 0.08 | 25–50 | 1–3 | No inh[c] | 6.3 | nd | nd |
| 82 | 2.1 | 250–500 | 63–125 | >250[c] | nd | nd | nd |
| 83 | 0.30 | 250–500 | 13–25 | >200[c] | 6 | +(50) | nd |
| 84 | 0.42 | nd | nd | nd | nd | nd | nd |
| 85 | 0.72 | >500 | 19–38 | >75[c] | nd | nd | nd |
| 86 | 0.53 | >500 | 19–38 | >75[c] | nd | nd | nd |
| 87 | 2.00 | >500 | 50–100 | >100[c] | 50 | nd | nd |
| 88 | 0.41 | 250–500 | 19–38 | >75[c] | nd | nd | nd |
| 89 | 0.29 | 500 | 50 | No inh[c] | nd | nd | nd |
| 90 | 0.73 | >500 | 50–100 | No inh[c] | nd | nd | nd |
| 91 | 0.43 | nd | nd | nd | nd | nd | nd |
| 92 | 0.12 | 63–125 | 13–25 | No inh[c] | 3.1 | +(25) | nd |
| 93 | 1.27 | 100–200 | >100[c] | No inh[c] | 13 | nd | nd |
| 94 | 0.74 | 200 | 50–100 | No inh[c] | 25 | nd | nd |
| 95 | 0.26 | nd | nd | nd | nd | nd | nd |
| 96 | 0.46 | 100–200 | 50 | No inh[c] | nd | nd | nd |
| 97 | 0.023 | >350 | 5–10 | No inh[c] | 2 | +(25–50) | nd |
| 98 | 0.055 | >340 | 5–10 | No inh[c] | 3 | +(50) | nd |
| 99 | 0.52 | nd | nd | nd | nd | nd | nd |
| 100 | 0.19 | >400 | 8–15 | >60 | 0.7 | nd | nd |
| 101 | 0.68 | nd | nd | nd | nd | nd | nd |
| 102 | 0.06 | >400 | 25–50 | >200 | 1.3 | +(25) | ~25 per os |
| 103 | 0.10 | 25–50 | 25 | >25 | 0.13 | nd | nd |
| 104 | 0.27 | nd | nd | nd | nd | nd | nd |
| 105 | 0.12 | nd | nd | nd | nd | nd | nd |
| 106 | 0.14 | nd | nd | nd | nd | nd | nd |
| 107 | 0.49 | nd | nd | nd | nd | nd | nd |
| 108 | 0.41 | nd | nd | nd | nd | nd | nd |
| 109 | 0.03 | 100–200 | 3–6 | No inh[c] | 0.4 | nd | nd |
| 110 | 0.15 | 200–400 | 25 | No inh[c] | 9 | nd | nd |
| 111 | 0.19 | 36 | 3 | No inh[c] | 75 | nd | nd |
| 112 | 0.39 | nd | nd | nd | nd | nd | nd |
| 113 | 1.91 | nd | nd | nd | nd | nd | nd |
| 114 | 0.26 | nd | nd | nd | nd | nd | nd |
| 115 | 0.24 | nd | nd | nd | nd | nd | nd |
| 116 | 0.19 | nd | nd | nd | nd | nd | nd |
| 117 | 1.09 | 12 | 12 | 12 | 2.2 | nd | nd |
| 118 | 0.46 | 200–400 | >100 | >100 | 3.4 | nd | nd |
| 119 | 0.02 | >400 | <3 | No inh[c] | 0.05 | nd | nd |
| 120 | 0.48 | nd | nd | nd | nd | nd | nd |
| 121 | 0.21 | <11 | 0.8–2 | No inh[c] | 25 | nd | nd |
| 122 | 0.13 | 200–400 | 12–25 | No inh[c] | 1.8 | nd | nd |
| 123 | 0.10 | 50–100 | 12–25 | >25 | 0.6 | +(50) | nd |
| 124 | 0.03 | 100–200 | 1.5 | No inh[c] | 0.1 | nd | nd |
| 125 | 0.11 | >400 | 1–3 | No inh[c] | 0.4 | nd | ~90 per os |
| 126 | 0.81 | nd | nd | nd | nd | nd | nd |
| 127 | 0.05 | 125–250 | 0.8–1.6 | No inh[c] | 0.1 | nd | nd |
| 128 | 0.16 | 125–250 | 1.5 | No inh[c] | 0.1 | nd | nd |
| 129 | 0.10 | nd | nd | nd | nd | nd | nd |
| 130 | 0.33 | nd | nd | nd | nd | nd | nd |
| 131 | 0.20 | >400 | 3–5 | No inh[c] | 1.1 | nd | nd |
| 132 | 0.22 | 200–400 | 5 | No inh[c] | 2.4 | nd | nd |
| 133 | 0.15 | >400 | 5–10 | No inh[c] | 0.4 | nd | nd |
| 134 | 0.05 | >250 | 1.5 | No inh[c] | 0.1 | nd | nd |
| 135 | 0.20 | >400 | 25 | No inh[c] | 1.7 | nd | nd |
| 136 | 0.19 | 150–300 | 0.6–1 | No inh[c] | nd | nd | nd |
| 137 | 0.04 | 200–400 | 1–3 | No inh[c] | 0.4 | nd | nd |
| 138 | 0.04 | 250–500 | 6 | No inh[c] | nd | +(25–50) | nd |
| 139 | 0.79 | nd | nd | nd | nd | nd | nd |
| 140 | 0.11 | 180–360 | 1.2 | >10 | 0.2 | nd | nd |

TABLE 23-continued

Results of Biological Testing.[a]

| Cmpd. Of Ex. | LFA-1/ICAM Binding Assay $K_d$ ($\mu M$) | Cellular Toxicity Assay MTT $LD_{50}$ ($\mu M$) | Assay to Detect SKW3 Cells Binding to: | | JY Cell Aggregation Assay JY Cell $IC_{50}$ ($\mu M$) | Mixed Lymphocyte Reaction MLR +/- ($\mu M$) | Allogeneic Cell Transplantation Assay ACT $ED_{50}$ (mg/kg) |
|---|---|---|---|---|---|---|---|
| | | | ICAM $IC_{50}$ ($\mu M$) | FIBRONECTIN $IC_{50}$ ($\mu M$) | | | |
| 141 | 0.22 | 300 | 15 | >15 | 0.1 | — | nd |
| 142 | 0.43 | nd | nd | nd | nd | nd | nd |
| 143 | 1.20 | nd | nd | nd | nd | nd | nd |
| 144 | 0.35 | nd | nd | nd | nd | nd | nd |
| 145 | 1.05 | nd | nd | nd | nd | nd | nd |
| 146 | 0.13 | 100 | 13–25 | No inh[c] | 0.4 | +(50) | nd |
| 147 | 0.34 | nd | nd | nd | nd | nd | nd |
| 148 | 0.50 | nd | nd | nd | nd | nd | nd |
| 149 | 0.20 | 170–340 | 10 | >10 | 2.9 | nd | nd |
| 150 | 0.51 | nd | nd | nd | nd | nd | nd |
| 151 | 0.046 | >410 | 5–10 | No inh[c] | 0.2 | +(25) | nd |
| 152 | 2.66 | nd | nd | nd | nd | nd | nd |
| 153 | 2.19 | nd | nd | nd | nd | nd | nd |
| 154 | 0.094 | 200 | 5–10 | No inh[c] | 0.4 | nd | nd |
| 155 | 0.51 | nd | nd | nd | nd | nd | nd |
| 156 | 0.69 | nd | nd | nd | nd | nd | nd |
| 157 | 0.037 | >390 | 5–10 | No inh[c] | 0.4 | +(25) | nd |
| 158 | 0.69 | nd | nd | nd | nd | nd | nd |
| 159 | 0.11 | 50–100 | 10–20 | No inh[c] | 2 | nd | nd |
| 160 | 0.64 | nd | nd | nd | nd | nd | nd |
| 161 | 4.56 | nd | nd | nd | nd | nd | nd |
| 162 | 1.05 | nd | nd | nd | nd | nd | nd |
| 163 | 0.16 | 200–400 | 9–19 | >75[c] | 2.4 | nd | nd |
| 164 | 0.28 | 100–200 | >100[c] | No inh[c] | 25 | nd | nd |
| 165 | 1.07 | nd | nd | nd | nd | nd | nd |
| 166 | 0.28 | nd | nd | nd | nd | nd | nd |
| 167 | 0.60 | nd | nd | nd | nd | nd | nd |
| 168 | 0.41 | nd | nd | nd | nd | nd | nd |
| 169 | 0.05 | 160–230 | 12–25 | No inh[c] | 1.5 | +(25) | nd |
| 170 | 0.02 | nd | nd | nd | nd | nd | nd |
| 171 | 0.18 | 100–200 | 102 | No inh[c] | 0.2 | nd | nd |
| 172 | 0.17 | 165 | 1.8 | No inh[c] | 0.7 | nd | nd |
| 173 | 0.17 | 200–400 | 4.8 | No inh[c] | 2.2 | nd | nd |
| 174 | 0.71 | nd | nd | nd | nd | nd | nd |
| 175 | 0.23 | nd | nd | nd | nd | nd | nd |
| 176 | 3.96 | nd | nd | nd | nd | nd | nd |
| 177 | 0.25 | 155–310 | 7–14 | No inh[c] | 3.7 | nd | nd |
| 178 | 1.17 | nd | nd | nd | nd | nd | nd |
| 179 | 3.84 | nd | nd | nd | nd | nd | nd |
| 180 | 0.19 | 200–400 | 1.5–3 | No inh[c] | 1.3 | nd | nd |
| 181 | 47%[b] | nd | nd | nd | nd | nd | nd |
| 182 | 0.05 | 200–400 | 3–6 | No inh[c] | 0.02 | +(25) | nd |
| 183 | 0.94 | nd | nd | nd | nd | nd | nd |
| 184 | 0.37 | 50–100 | 0.8–1.5 | No inh[c] | 0.3 | nd | nd |
| 185 | 0.25 | nd | nd | nd | nd | nd | nd |
| 186 | 1.11 | nd | nd | nd | nd | nd | nd |
| 187 | 0.29 | 171 | 0.6 | No inh[c] | 0.6 | nd | nd |
| 188 | 0.04 | 56–112 | 0.3–1 | No inh[c] | 0.03 | nd | nd |
| 189 | 0.19 | 63 | 0.6–1.2 | No inh[c] | nd | nd | nd |
| 190 | 0.43 | 50–100 | 6–12 | No inh[c] | 1.4 | nd | nd |
| 191 | 0.14 | nd | nd | nd | nd | nd | ACT |
| 192 | 1[e] | nd | nd | nd | nd | nd | nd |
| 193 | 0.29 | nd | nd | nd | nd | nd | nd |
| 194 | 0.27 | nd | nd | nd | nd | nd | nd |
| 195 | 0.30 | nd | nd | nd | nd | nd | nd |
| 196 | 0.09 | nd | nd | nd | nd | nd | nd |
| 197 | 0.19 | nd | nd | nd | nd | nd | nd |
| 198 | 0.14 | nd | nd | nd | nd | nd | nd |
| 199 | 0.27 | nd | nd | nd | nd | nd | nd |
| 200 | 0.09 | nd | nd | nd | nd | nd | nd |
| 201 | 0.68 | nd | nd | nd | nd | nd | nd |
| 202 | 0.23 | nd | nd | nd | nd | nd | nd |
| 203 | 0.34 | nd | nd | nd | nd | nd | nd |
| 204 | 0.50 | nd | nd | nd | nd | nd | nd |
| 205 | 0.56 | nd | nd | nd | nd | nd | nd |
| 206 | 0.73 | nd | nd | nd | nd | nd | nd |
| 207 | 1.28 | nd | nd | nd | nd | nd | nd |
| 208 | 0.65 | nd | nd | nd | nd | nd | nd |
| 209 | 0.94 | nd | nd | nd | nd | nd | nd |
| 210 | 0.54 | nd | nd | nd | nd | nd | nd |

TABLE 23-continued

Results of Biological Testing.[a]

| Cmpd. Of Ex. | LFA-1/ICAM Binding Assay $K_d$ ($\mu$M) | Cellular Toxicity Assay MTT LD$_{50}$ ($\mu$M) | Assay to Detect SKW3 Cells Binding to: | | JY Cell Aggregation Assay JY Cell IC50 ($\mu$M) | Mixed Lymphocyte Reaction MLR +/− ($\mu$M) | Allogeneic Cell Transplantation Assay ACT ED$_{50}$ (mg/kg) |
|---|---|---|---|---|---|---|---|
| | | | ICAM IC$_{50}$ ($\mu$M) | FIBRONECTIN IC$_{50}$ ($\mu$M) | | | |
| 211 | 2[e] | nd | nd | nd | nd | nd | nd |
| 212 | 0.07 | nd | nd | nd | nd | nd | nd |
| 213 | 2[e] | nd | nd | nd | nd | nd | nd |
| 214 | 0.09 | nd | nd | nd | nd | nd | nd |
| 215 | 0.20 | 100–200 | 50–100 | >100 | 3.1 | +(50) | nd |
| 216 | 0.50 | nd | nd | nd | nd | nd | nd |
| 217 | 1.78 | nd | nd | nd | nd | nd | nd |
| 218 | 0.80 | nd | nd | nd | nd | nd | nd |
| 219 | 1.03 | nd | nd | nd | nd | nd | nd |
| 220 | 0.27 | nd | nd | nd | nd | nd | nd |
| 221 | 0.14 | nd | nd | nd | nd | nd | nd |
| 222 | 0.06 | nd | nd | nd | nd | nd | nd |
| 223 | 0.15 | 200–400 | 2–4 | No inh[c] | 0.2 | nd | nd |
| 224 | 0.28 | <25 | 5–10 | No inh[c] | 3.1 | nd | nd |
| 225 | 0.63 | 50–100 | 3–4 | No inh[c] | 0.2 | +(25) | nd |
| 226 | 0.07 | 100 | 3–6 | No inh[c] | 1.6 | +(25) | nd |
| 227 | 0.18 | 200–400 | 25 | No inh[c] | 3.1 | +(50) | nd |
| 228 | 0.41 | 50–100 | 12–25 | No inh[c] | 1.6 | nd | nd |
| 229 | 0.30 | 50–100 | 6–13 | No inh[c] | 3.1 | +(50) | nd |
| 230 | 2.20 | nd | nd | nd | nd | nd | nd |
| 231 | 0.27 | 40–80 | 2–5 | No inh[c] | nd | nd | nd |
| 232 | 1.24 | nd | nd | nd | nd | nd | nd |
| 233 | 1.79 | nd | nd | nd | nd | nd | nd |
| 234 | 0.41 | 100–200 | 5–10 | No inh[c] | 1.6 | nd | nd |
| 235 | 0.33 | 100–200 | 9 | No inh[c] | 1.6 | nd | nd |
| 236 | 0.33 | nd | nd | nd | nd | nd | nd |
| 237 | 0.13 | 50–100 | 1–2 | No inh[c] | 0.1 | nd | nd |
| 238 | 0.08 | nd | nd | nd | nd | nd | nd |
| 239 | 0.28 | nd | nd | nd | nd | nd | nd |
| 240 | 0.11 | 11–23 | 1–3 | 13.4 | 6.3 | nd | nd |
| 241 | 0.10 | 9–18 | 0.8–1.6 | 13 | nd | nd | nd |
| 242 | 0.40 | 16–32 | 10–25 | No inh[c] | 2.8 | nd | nd |
| 243 | 0.11 | 10–20 | 5–6 | No inh[c] | 3.1 | nd | nd |
| 244 | 3.98 | 200–400 | 4–8 | No inh[c] | 2.2 | nd | nd |
| 245 | 0.21 | 25–50 | 1–3 | No inh[c] | 0.7 | nd | nd |
| 246 | 0.25 | nd | nd | nd | nd | nd | nd |
| 247 | 0.23 | 40–80 | 1.5–3 | No inh[c] | 2.3 | nd | nd |
| 248 | 0.37 | 50–100 | 9–18 | No inh[c] | 0.7 | nd | nd |
| 249 | 0.16 | 200–400 | <1 | No inh[c] | 0.4 | nd | nd |
| 250 | 0.04 | 100–200 | <1 | No inh[c] | 0.1 | nd | nd |
| 251 | 0.06 | 100–200 | <0.5 | No inh[c] | nd | nd | nd |
| 252 | 0.11 | 17–20 | 0.4–0.8 | No inh[c] | 0.3 | nd | nd |
| 253 | 0.05 | 100–200 | 1–2 | No inh[c] | 0.2 | nd | nd |
| 254 | 0.08 | 100–200 | 1–2 | No inh[c] | 0.4 | nd | nd |
| 255 | 0.14 | 100–200 | 1 | No inh[c] | 0.2 | nd | nd |
| 256 | 0.12 | 150–300 | 0.8–2 | No inh[c] | 0.4 | nd | nd |
| 257 | 0.08 | 300 | 1.6 | No inh[c] | 0.6 | nd | nd |
| 258 | 1.66 | nd | nd | nd | nd | nd | nd |
| 259 | 3.54 | nd | nd | nd | nd | nd | nd |
| 260 | 0.07 | 200–400 | 19–38 | No inh[c] | 1.1 | nd | nd |
| 261 | nd[f] | nd | nd | nd | nd | nd | nd |
| 262 | 0.08 | 25–75 | 1–2 | No inh[c] | 0.4 | nd | nd |
| 263 | 0.09 | 20–40 | 0.8–1.6 | No inh[c] | 0.8 | nd | nd |
| 264 | 0.12 | 12–24 | 2–5 | No inh[c] | 0.4 | nd | nd |
| 265 | 0.28 | 130–250 | 19–38 | >75[c] | 3 | nd | nd |
| 266 | 0.14 | >500 | 25–50 | >50[c] | 3 | +(25–50) | nd |
| 267 | 0.40 | 250 | nd | nd | nd | nd | nd |
| 268 | 1.59 | 250–500 | nd | nd | nd | nd | nd |
| 269 | 0.29 | 250–500 | 25 | No inh[c] | nd | nd | nd |
| 270 | 0.65 | 250–500 | nd | nd | nd | nd | nd |
| 271 | 0.02 | 250–500 | 3 | No inh[c] | 0.1 | +(13–25) | ~20 (per os) |
| 272 | 0.56 | 250–500 | 50–100 | No inh[c] | nd | nd | nd |
| 273 | 0.19 | 150–300 | 38 | >75[c] | 2 | — | nd |
| 274 | 0.14 | 200–300 | 25–50 | >100[c] | 3 | — | nd |
| 275 | 2.00 | nd | nd | nd | nd | nd | nd |
| 276 | 1.11 | 375 | 10 | No inh[c] | 0.5 | +(25) | nd |
| 277 | 0.07 | nd | nd | nd | nd | nd | nd |
| 278 | 1.09 | nd | nd | nd | nd | nd | nd |

Description of Therapeutic Use

The novel and known small molecules utilized in the method according to the invention inhibit the ICAM-1/LFA-1 dependent homotypic aggregation of human lymphocytes, human lymphocyte adherence to ICAM-1 and human lymphocyte responses to antigens. These compounds have therapeutic utility in the modulation of immune cell activation/proliferation, e.g., as competitive inhibitors of intercellular ligand/receptor binding reactions involving CAMs and Leukointegrins. Inflammatory conditions which may be treated with the compounds comprehended by the invention include conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). In accordance with the invention, these novel and known compounds may also be used in treating asthma or as an adjunct to minimize toxicity with cytokine therapy in the treatment of cancers. In general these compounds may be employed in the treatment of those diseases currently treatable through steroid therapy.

In accordance with the method provided by the invention, these novel and known compounds may be administered for either a "prophylactic" or "therapeutic" purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel and known compounds of the formula I may, in accordance with the invention, be administered in single or divided doses by the oral, parenteral or topical routes. A suitable oral dosage for a compound of formula I would be in the range of about 0.5 mg to 1 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

Formulations

Compounds of the formula I can be formulated for therapeutic administration in a number of ways. Descriptions of several exemplary formulations are given below.

Example A

Capsules or Tablets

| Example A-1 | | Example A-2 | |
|---|---|---|---|
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

Parenteral Solutions

| Ingredients | Quantity |
|---|---|
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

Suspension

| Ingredients | Quantity |
|---|---|
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

What is claimed is:

1. A compound of the formula I

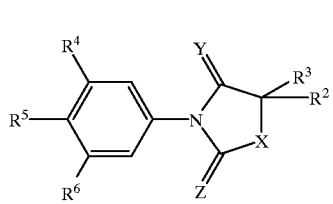

wherein:

Y is an oxygen atom;

Z is an oxygen atom;

X is a divalent group of the formula $>CHR^1$ or $>NR^1$, wherein $R^1$ is:
  (A) a hydrogen atom,
  (B) branched or unbranched alkyl of 1 to 6 carbon atoms or cycloalkyl of 3 to 6 carbon atoms, which alkyl or cycloakyl group is unsubstituted or mono-substituted with:
    (i) oxo,
    (ii) aryl selected from the class consisting of phenyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl and triazinyl,
    wherein one or more hydrogen atoms of said aryl group are or are not independently replaced with:
    (a) alkyl of 1 to 3 carbon atoms,
    (b) —COOH,
    (c) —SO$_2$OH,
    (d) —PO(OH)$_2$,
    (e) a group of the formula —COOR$^7$, wherein R$^7$ is straight or branched alkyl of 1 to 5 carbon atoms or cycloalkyl of 3 to 5 carbon atoms,
    (f) a group of the formula —NH$_2$,
    (g) a group of the formula —CONH$_2$,
    (h) a group of the formula —OR$^{12a}$, wherein R$^{12a}$ is a hydrogen atom or a methyl,
    (i) an amidino group of the formula

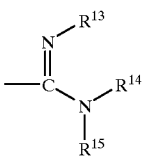

wherein R$^{13}$, R$^{14}$ and R$^{15}$ are each hydrogen atoms,
    (iii) a group of the formula —COOR$^{16}$, wherein R$^{16}$ is straight or branched alkyl of 1 to 7 carbon atoms or cycloalkyl of 3 to 6 carbon atoms, (iv) a group of the formula OR$^{19}$, wherein R$^{19}$ is a hydrogen atom, or an alkyl or acyl group of 1 to 7 carbon atoms, or
(v) a quaternary group of the formula

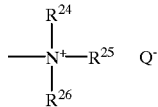

wherein R$^{24}$, R$^{25}$ and R$^{26}$ are each methyl and Q$^-$ is a chlorine, bromine or iodine counterion,
(C) a group of the formula —COOH connected via a branched or unbranched alkyl group of 2 to 5 carbon atoms,
(D) a group of the formula —PO(OH)$_2$ connected via a branched or unbranched alkyl group of 2 to 6 carbon atoms,
(E) a group of the formula —SO$_2$OH connected via a branched or unbranched alkyl group of 2 to 6 carbon atoms,
(F) an amidino group of the formula

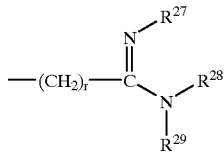

wherein r is 2, 3, 4, 5 or 6, and
R$^{27}$, R$^{28}$ and R$^{29}$ are each hydrogen atoms,
(G) an guanidino group of the formula

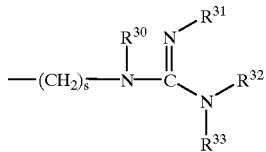

wherein s is 2, 3, 4, 5 or 6,
R$^{30}$, R$^{31}$, R$^{32}$ and R$^{33}$ are each hydrogen atoms, or
(H) piperidyl, wherein the nitrogen atom of said group is unsubtituted or substituted with:
(i) alkyl of 1 to 3 carbon atoms,
(ii) a group of the formula —COO(C$_{1-6}$alkyl),
(iii) a group of the formula —COOH connected via an alkyl group of 1 to 4 carbon atoms,
(iv) a group of the formula —PO(OH)$_2$ connected via an alkyl group of 1 to 6 carbon atoms, or
(v) a group of the formula —SO$_2$OH connected via an alkyl group of 1 to 6 carbon atoms;
R$^2$ is:
(A) a hydrogen atom, or
(B) methyl;
R$^3$ is a group of the formula —CH$_2$R$^{41}$, wherein R$^{41}$ is
aryl selected from the class consisting of phenyl, thiophenyl, pyridyl, pyrimidinyl, furyl, oxazolyl, thiazolyl, isoxazolyl, isothiazolyl, oxadiazolyl, thiadiazolyl, pyridazinyl, and pyrazinyl,
wherein one or more of the hydrogen atoms of said aryl group are necessarily and independently replaced with:

(A) R$^{62}$, which is aryl selected from the class consisting of phenyl, thiophenyl, pyridyl, pyrimidinyl, furyl, oxazolyl, thiazolyl, isoxazolyl, isothiazolyl, oxadiazolyl, thiadiazolyl, pyridazinyl, and pyrazinyl,
wherein one or more of the hydrogen atoms of said aryl group are or are not independently replaced with:
(i) methyl,
(ii) —COOH,
(iii) a group of the formula —COOR$^{63}$, wherein R$^{63}$ is methyl,
(iv) a group of the formula —OR$^{68}$, wherein R$^{68}$ is a hydrogen atom or methyl, or
(v) halogen,
(B) methyl, which is unsubstituted or mono- or polysubstituted with fluorine atoms or which is unsubstituted or monosubstituted with R$^{62}$,
(C) branched or unbranched alkyl of 2 to 6 carbon atoms or cycloalkyl of 3 to 6 carbon atoms, which alkyl or cycloakyl group is unsubstituted or mono- or polysubstituted with halogen or oxo,
(D) a group of the formula —COOR$^{73}$, wherein R$^{73}$ is methyl,
(E) a group of the formula —CONR$^{76}$R$^{77}$, wherein R$^{76}$ and R$^{77}$ are each methyl, and wherein one of R$^{76}$ and R$^{77}$ is methyl and the other is the group R$^{62}$,
(F) a group of the formula —COR$^{78}$, wherein R$^{78}$ is a hydrogen atom, methyl or R$^{62}$,
(G) a group of the formula —OR$^{79}$, wherein R$^{79}$ is a hydrogen atom, methyl or R$^{62}$,
(H) cyano,
(I) nitro, or
(J) halogen;
R$^4$ is Cl or trifluoromethyl;
R$^5$ is a hydrogen atom; and,
R$^6$ is Cl, or trifluoromethyl;
or a pharmaceutically acceptable salt thereof.

2. A compound of the formula I, in accordance with claim 1, wherein:
Y is an oxygen atom;
Z is an oxygen atom;
X is a divalent group of the formula >CHR$^1$ or >NR$^1$, wherein R$^1$ is:
(A) a hydrogen atom,
(B) branched or unbranched alkyl of 1 to 6 carbon atoms or cycloalkyl of 3 to 6 carbon atoms, which alkyl or cycloalkyl group is unsubstituted or monosubstituted with:
(i) oxo,
(ii) aryl selected from the class consisting of phenyl or pyridyl,
wherein one or more hydrogen atoms of said aryl group are or are not independently replaced with:
(a) alkyl of 1 to 3 carbon atoms,
(b) —COOH,
(c) —SO$_2$OH,
(d) —PO(OH)$_2$, (e) a group of the formula —OR$^{12a}$, wherein R$^{12a}$ is a hydrogen atom or a methyl,
(f) an amidino group of the formula

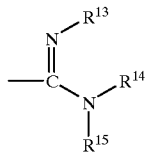

wherein R$^{13}$, R$^{14}$ and R$^{15}$ are each hydrogen atoms,
(iii) a group of the formula —OR$^{19}$, wherein R$^{19}$ is a hydrogen atom, or an alkyl or acyl group of 1 to 7 carbon atoms, or
(iv) a quaternary group of the formula

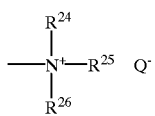

wherein R$^{24}$, R$^{25}$ and R$^{26}$ are each methyl and Q$^-$ is a chlorine, bromine or iodine counterion,
(C) a group of the formula —COOH connected via a branched or unbranched alkyl group of 2 to 5 carbon atoms,
(D) a group of the formula —PO(OH)$_2$ connected via a branched or unbranched alkyl group of 2 to 6 carbon atoms,
(E) a group of the formula —SO$_2$OH connected via a branched or unbranched alkyl group of 2 to 6 carbon atoms,
(F) an amidino group of the formula

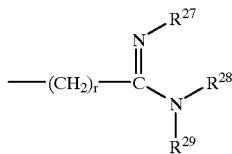

wherein r is 2, 3, 4, 5 or 6, and R$^{27}$, R$^{28}$ and R$^{29}$ are each hydrogen atoms,
(G) an guanidino group of the formula

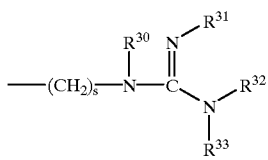

wherein s is 2, 3, 4, 5 or 6, R$^{30}$, R$^{31}$, R$^{32}$ and R$^{33}$ are each hydrogen atoms, or
(H) piperidyl, wherein the nitrogen atom of said group is unsubstituted or substituted with:
(i) alkyl of 1 to 3 carbon atoms,
(ii) a group of the formula —COO(C$_{1-6}$alkyl),
(iii) a group of the formula —COOH connected via an alkyl group of 1 to 4 carbon atoms,
(iv) a group of the formula —PO(OH)$_2$ connected via an alkyl group of 1 to 6 carbon atoms, or
(v) a group of the formula —SO$_2$OH connected via an alkyl group of 1 to 6 carbon atoms;

R$^2$ is:
(A) a hydrogen atom, or
(B) methyl;
R$^3$ is a group of the formula —CH$_2$R$^{41}$, wherein R$^{41}$ is
aryl selected from the class consisting of phenyl or pyridyl,
wherein one or more of the hydrogen atoms of said aryl group are necessarily and independently replaced with:
(A) R$^{62}$, which is aryl selected from the class consisting of phenyl, or pyridyl,
wherein one or more of the hydrogen atoms of said aryl group are or are not independently replaced with:
(i) methyl,
(ii) —COOH
(iii) a group of the formula —COOR$^{63}$, wherein R$^{63}$ is methyl,
(iv) a group of the formula —OR$^{68}$, wherein R$^{68}$ is a hydrogen atom or methyl, or
(v) halogen,
(B) methyl, which is unsubstituted or mono- or polysubstituted with fluorine atoms or which is unsubstituted or monosubstituted with R$^{62}$,
(C) branched or unbranched alkyl of 2 to 6 carbon atoms or cycloalkyl of 3 to 6 carbon atoms, which alkyl or cycloakyl group is unsubstituted or mono- or polysubstituted with fluorine or oxo,
(D) a group of the formula —COOR$^{73}$, wherein R$^{73}$ is methyl,
(E) a group of the formula —CONR$^{76}$R$^{77}$, wherein R$^{76}$ and R$^{77}$ are each methyl, and wherein one of R$^{76}$ and R$^{77}$ is methyl and the other is the group R$^{62}$,
(F) a group of the formula —COR$^{78}$, wherein R$^{78}$ is a hydrogen atom, methyl or R$^{62}$,
(G) a group of the formula —OR$^{79}$, wherein R$^{79}$ is a hydrogen atom, methyl or R$^{62}$,
(H) cyano,
(I) nitro, or
(J) halogen;
R$^4$ is a chlorine atom or trifluoromethyl;
R$^5$ is a hydrogen atom; and,
R$^6$ is a chlorine atom, or trifluoromethyl;
or a pharmaceutically acceptable salt thereof.

3. A compound of the formula I, in accordance with claim 2, wherein:
Y is an oxygen atom;
Z is an oxygen atom;
X is a divalent group of the formula >CHR$^1$ or >NR$^1$, wherein R$^1$ is:
(A) a hydrogen atom,
(B) alkyl of 1 to 2 carbon atoms which is unsubstituted or monosubstituted with:
(i) oxo,
(ii) aryl selected from the class consisting of phenyl or pyridyl,
wherein one hydrogen atom of said aryl group is or is not replaced with:
(a) alkyl of 1 to 3 carbon atoms,
(b) —COOH,
(c) —SO$_2$OH,
(d) —PO(OH)$_2$, (e) a group of the formula —OR$^{12a}$, wherein R$^{12a}$ is a hydrogen atom or a methyl, or
(f) an amidino group of the formula

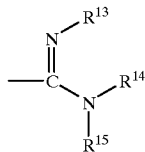

wherein R$^{13}$, R$^{14}$ and R$^{15}$ are each hydrogen atoms, or
(iii) a group of the formula —OR$^{19}$, wherein R$^{19}$ is a hydrogen atom or methyl,
a group of the formula —COOH connected via a branched or unbranched alkyl group of 2 to 5 carbon atoms,
(D) a group of the formula —PO(OH)$_2$ connected via a branched or unbranched alkyl group of 2 to 6 carbon atoms,
(E) a group of the formula —SO$_2$OH connected via a branched or unbranched alkyl group of 2 to 6 carbon atoms,
(F) an amidino group of the formula

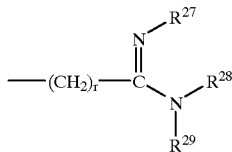

wherein r is 2, 3, 4, 5 or 6, and R$^{27}$, R$^{28}$ and R$^{29}$ are each hydrogen atoms, or
(G) an guanidino group of the formula

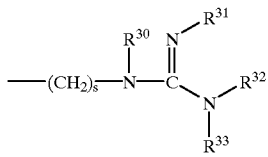

wherein s is 2, 3, 4, 5 or 6,
R$^{30}$, R$^{31}$, R$^{32}$ and R$^{33}$ are each hydrogen atoms,
R$^2$ is:
(A) a hydrogen atom, or
(B) methyl;
R$^3$ is a group of the formula —CH$_2$R$^{41}$, wherein R$^{41}$ is
phenyl
wherein one or more of the hydrogen atoms of said phenyl group are necessarily and independently replaced with:
(A) R$^{62}$, which is aryl selected from the class consisting of phenyl, or pyridyl,
wherein one or more of the hydrogen atoms of said aryl group are or are not independently replaced with:
(i) methyl,
(ii) a group of the formula —COOR$^{63}$, wherein R$^{63}$ is methyl,
(iii) a group of the formula —OR$^{68}$, wherein R$^{68}$ is a hydrogen atom or methyl, or
(iv) halogen,
(B) methyl, which is unsubstituted or mono- or polysubstituted with fluorine atoms or which is unsubstituted or monosubstituted with R$^{62}$,
(C) a group of the formula —COOR$^{73}$, wherein R$^{73}$ is methyl,
(D) a group of the formula —COR$^{78}$, wherein R$^{78}$ is methyl or R$^{62}$,
(E) a group of the formula —OR$^{79}$, wherein R$^{79}$ is a hydrogen atom, methyl or R$^{62}$,
(F) cyano,
(G) nitro, or
(H) halogen;
R$^4$ is a chlorine atom or trifluoromethyl;
R$^5$ is a hydrogen atom; and,
R$^6$ is a chlorine atom, or trifluoromethyl;
or a pharmaceutically acceptable salt thereof.
4. A compound of the formula I, in accordance with claims 3, wherein:
Y is an oxygen atom;
Z is an oxygen atom;
X is a divalent group of the formula >NR$^1$, wherein R$^1$ is:
(A) a hydrogen atom,
(B) methyl or ethyl, or
(C) —COCH$_3$
R$^2$ is:
(A) a hydrogen atom, or
(B) methyl;
R$^3$ is a group of the formula —CH$_2$R$^{41}$, wherein R$^{41}$ is:
phenyl,
wherein one or more of the hydrogen atoms of said phenyl group are necessarily and independently replaced with:
(A) R$^{62}$, which is aryl selected from the class consisting of phenyl, or pyridyl,
wherein one or more of the hydrogen atoms of said aryl group are or are not independently replaced with:
(i) methyl,
(ii) a group of the formula —COOR$^{63}$, wherein R$^{63}$ is methyl,
(iii) a group of the formula —OR$^{68}$, wherein R$^{68}$ is a hydrogen atom or methyl, or
(iv) halogen,
(B) methyl, which is unsubstituted or mono- or polysubstituted with fluorine atoms or which is unsubstituted or monosubstituted with R$^{62}$,
(C) a group of the formula —COOR$^{73}$, wherein R$^{73}$ is methyl,
(D) a group of the formula —COR$^{78}$, wherein R$^{78}$ is methyl or R$^{62}$,
(E) a group of the formula —OR$^{79}$, wherein R$^{79}$ is a hydrogen atom, methyl or R$^{62}$,
(F) cyano,
(G) nitro, or
(H) halogen;
R$^4$ is a chlorine atom or trifluoromethyl;
R$^5$ is a hydrogen atom; and,
R$^6$ is a chlorine atom, or trifluoromethyl;
or a pharmaceutically acceptable salt thereof.
5. A compound of the formula I, in accordance with claims 4, wherein:
Y is an oxygen atom;
Z is an oxygen atom;

X is a divalent group of the formula >NR¹,
  wherein R¹ is:
    (A) a hydrogen atom,
    (B) methyl or ethyl, or
    (C) —COCH₃
  R² is:
    (A) a hydrogen atom, or
    (B) methyl;
  R³ is a group of the formula —CH₂R⁴¹, wherein
    R⁴¹ is
      phenyl
        wherein one or more of the hydrogen atoms of said phenyl group are necessarily and independently replaced with:
          (A) R⁶², which is aryl selected from the class consisting of phenyl, or pyridyl,
            wherein one or more of the hydrogen atoms of said aryl group are or are not independently replaced with:
              (i) methyl, or
              (ii) halogen,
          (B) methyl, which is unsubstituted or mono- or polysubstituted with fluorine atoms,
          (C) a group of the formula —COR⁷⁸, wherein R⁷⁸ is methyl or R⁶²,
          (D) halogen;
  R⁴ is a chlorine atom;
  R⁵ is a hydrogen atom; and,
  R⁶ is a chlorine atom;

or a pharmaceutically acceptable salt thereof.

6. A compound selected from the group consisting of:

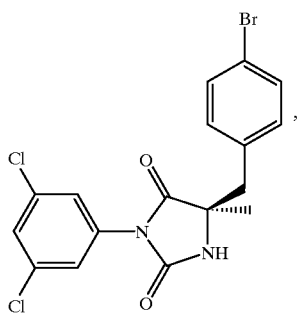

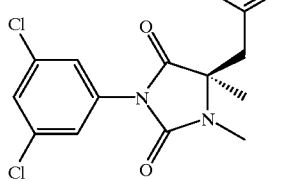

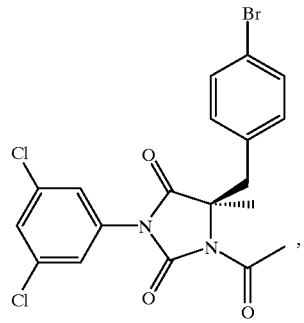

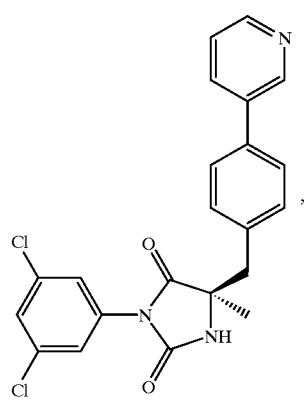

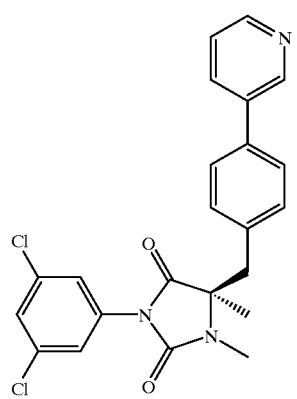

and

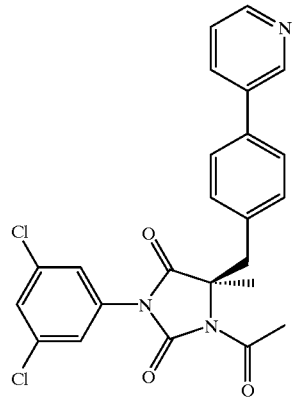

and pharmaceutically acceptable salts thereof.

7. A method for treating an inflammatory, immune cell-mediated disease or condition which comprises administering a prophylactic or therapeutic amount of a compound in accordance with claim 1, 2, 3, 4, 5 or 6.

8. The method of claim 7 wherein the disease or condition is selected from the group consisting of adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome.

9. The method of claim 1 or 7 wherein the disease or condition is selected from the group consisting of psoriasis, organ/tissue transplant rejection, graft vs. host reactions and autoimmune diseases.

10. The method of claim 7 wherein the disease or condition is asthma.

11. The method of claim 7 wherein the condition is toxicity associated with cytokine therapy.

12. A pharmaceutical composition comprising a pharmaceutically acceptable carrier and a compound in accordance with claim 1, 2, 3, 4, 5 or 6.

* * * * *